(12) United States Patent
Takenaka et al.

(10) Patent No.: US 8,778,236 B2
(45) Date of Patent: Jul. 15, 2014

(54) CHROMENE COMPOUND

(75) Inventors: Junji Takenaka, Shunan (JP); Junji Momoda, Shunan (JP); Kazuhiro Teranishi, Shunan (JP); Toshiaki Takahashi, Shunan (JP); Mitsuyoshi Sando, Shunan (JP); Shinobu Izumi, Shunan (JP)

(73) Assignee: Tokuyama Corporation, Shunan-Shi (JP)

( * ) Notice: Subject to any disclaimer, the term of this patent is extended or adjusted under 35 U.S.C. 154(b) by 0 days.

(21) Appl. No.: 14/003,666

(22) PCT Filed: Mar. 7, 2012

(86) PCT No.: PCT/JP2012/056491
§ 371 (c)(1),
(2), (4) Date: Nov. 14, 2013

(87) PCT Pub. No.: WO2012/121414
PCT Pub. Date: Sep. 13, 2012

(65) Prior Publication Data
US 2014/0054520 A1   Feb. 27, 2014

(30) Foreign Application Priority Data

Mar. 8, 2011 (JP) ................. 2011-050730
Jun. 9, 2011 (JP) ................. 2011-128852
Sep. 29, 2011 (JP) ................. 2011-214010

(51) Int. Cl.
G02B 5/23        (2006.01)
F21V 9/00        (2006.01)
G02B 5/02        (2006.01)
G02C 7/10        (2006.01)
G02F 1/361       (2006.01)
G03B 11/00       (2006.01)
G02F 1/03        (2006.01)
G02F 1/07        (2006.01)

(52) U.S. Cl.
USPC .......... 252/586; 252/582; 359/241; 544/79; 544/129; 544/141; 544/143; 544/150; 544/154; 546/15; 548/407; 549/330; 549/382; 549/406; 549/502; 564/114; 564/426; 568/325; 568/633

(58) Field of Classification Search
USPC .......... 252/582, 586; 359/241; 544/79, 129, 544/141, 143, 150, 154; 546/15; 548/407; 549/330, 382, 406, 502; 564/114, 426; 568/325, 633
See application file for complete search history.

(56) References Cited

U.S. PATENT DOCUMENTS 6,146,554 A   11/2000 Melzig et al.
6,296,785 B1  10/2001 Nelson et al.
6,723,859 B2   4/2004 Kawabata et al.
7,008,568 B2   3/2006 Qin
7,521,004 B2   4/2009 Momoda et al.
8,147,726 B2   4/2012 Kasai et al.
8,308,996 B2  11/2012 Takahashi et al.
2012/0121934 A1   5/2012 Takahashi et al.
2012/0161089 A1   6/2012 Takahashi et al.
2012/0270071 A1  10/2012 Takahashi et al.

FOREIGN PATENT DOCUMENTS

| JP | 2009-120536 A | 6/2009 |
| WO | WO 99/15518 A1 | 4/1999 |
| WO | WO 01/19813 A1 | 3/2001 |
| WO | WO 01/60811 A1 | 8/2001 |
| WO | WO 03/044022 A2 | 5/2003 |
| WO | WO 2005/028465 A1 | 3/2005 |
| WO | WO 2009/136668 A1 | 11/2009 |
| WO | WO 2011/010744 A1 | 1/2011 |
| WO | WO 2011/016582 A1 | 2/2011 |
| WO | WO 2011/025056 A1 | 3/2011 |

OTHER PUBLICATIONS

International Preliminary Examination Report mailed Sep. 19, 2013 (Forms PCT/IB/338, PCT/IB/373 and PCT/ISA/237).

(Continued)

*Primary Examiner* — Bijan Ahvazi
(74) *Attorney, Agent, or Firm* — Birch, Stewart, Kolasch & Birch, LLP.

(57) ABSTRACT

A novel photochromic compound which develops a color of a neutral tint and has high color optical density, high fading speed and excellent durability. The present invention is a chromene compound having an indeno(2,1-f)naphtho(1,2-b) pyran structure as the basic skeleton in which a hetero ring having two hetero atoms including at least one sulfur atom is directly bonded to the 6-position and the 7-position of the indeno(2,1-f)naphtho(1,2-b)pyran structure via the hetero atom like the compound represented by the following formula (18).

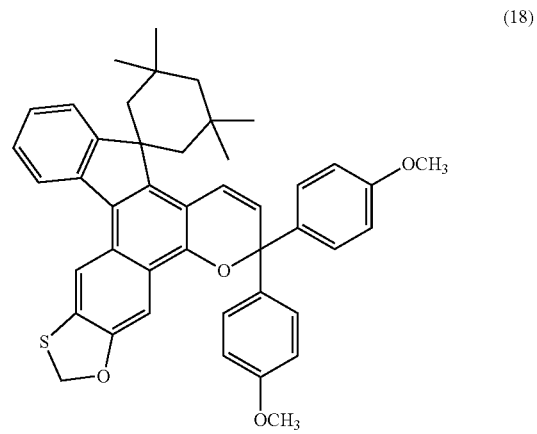

(18)

16 Claims, No Drawings

(56) References Cited

OTHER PUBLICATIONS

Christos G. Gourdoupis et al.; A Direct and Versatile Synthesis of . . . ; Synthetic Communications, 23(16); pp. 2241-2249; 1993.

Derrick Clive et al.—Formal Radical Cyclization onto Benzene Rings: A General Method and Its Use in the Synthesis of ent-Nocardione A; Journal of Organic Chemistry; 69; No. 10; pp. 3282-3293; 2004.

Maria Grazia Cabiddu et al.; A re-examination of the methylenation reaction; Tetrahedron; 59(24); pp. 4383-4387 (2003).

PCT/ISA/210—International Search Report mailed on Apr. 17, 2012, issued in PCT/JP2012/056491.

CHROMENE COMPOUND

TECHNICAL FIELD

The present invention relates to a novel chromene compound which is useful as a photochromic compound for photochromic spectacle lenses.

BACKGROUND ART

Photochromism is the reversible function of a certain compound that it changes its color swiftly upon exposure to light including ultraviolet light such as sunlight or light from a mercury lamp and returns to its original color when it is put in the dark by stopping its exposure to light. A compound having this property is called "photochromic compound" and used as a material for photochromic plastic lenses.

For the photochromic compound used for this purpose, the following properties are required: (I) the degree of coloration at a visible light range before ultraviolet light is applied (to be referred to as "initial coloration" hereinafter) should be low, (II) the degree of coloration upon exposure to ultraviolet light (to be referred to as "color optical density" hereinafter) should be high, (III) the speed from the time when the application of ultraviolet light is started to the time when the color optical density reaches saturation (to be referred to as "color development sensitivity" hereinafter) should be high; (IV) the speed from the stoppage of the application of ultraviolet light to the time when the compound returns to its original state (to be referred to as "fading speed" hereinafter) should be high, (V) the repeat durability of this reversible function should be high, and (VI) the solubility in a monomer composition which will become a host material after curing of the photochromic compound should be high so that its dispersibility in the host material in use becomes high.

As the photochromic compound which can satisfy these requirements, there are known chromene compounds having an indeno(2,1-f)naphtho(1,2-b)pyran structure as the basic skeleton (refer to a pamphlet of International Laid-Open WO99/15518 and a pamphlet of International Laid-Open WO2001/60811).

It is preferred that a photochromic plastic lens comprising the photochromic compound should develop a color of a neutral tint such as gray or brown. A color of a neutral tint is obtained by mixing together several different kinds of photochromic compounds which develop different colors. More specifically, it can be obtained by mixing together a yellow to red photochromic compound (yellow compound) having a maximum absorption at 430 to 530 nm and a purple to blue photochromic compound (blue compound) having a maximum absorption at 550 to 650 nm.

However, when color control is carried out by this method, various problems occur due to the difference in photochromic properties between the compounds which have been mixed together. For example, when the repeat durability of the yellow compound is lower than that of the blue compound and the photochromic plastic lens is used for a long time, there occurs a problem that the developed color gradually changes to a color of a strong blue tint.

Further, when the color development sensitivity and fading speed of the yellow compound are lower than those of the blue compound, there arises a problem that color during development has a strong blue tint and color during fading has a strong yellow tint.

It is considered that this problem can be solved by using a single compound which has two or more absorption maximums at the time of exposure and develops a color of a neutral tint (double peak compound). It is known that the yellow compound is generally inferior to the blue compound in durability. Therefore, a compound having higher yellow color optical density (having a maximum absorption wavelength at 430 to 530 nm) than blue color optical density (having a maximum absorption wavelength at 550 to 650 nm) is desired as the double peak compound (the ratio of the yellow color optical density to the blue color optical density in the double peak compound may be referred to as "double peak characteristic" hereinafter).

As the photochromic compound having two or more absorption maximums at the time of color development (double peak compound), there are known compounds represented by the following formulas (A) to (D).

However, these compounds have room for the improvement of the following points. That is, a chromene compound represented by the following formula (A) (refer to a pamphlet of International Laid-Open WO2001/19813) has low fading speed and low repeat durability though its double peak characteristic is high.

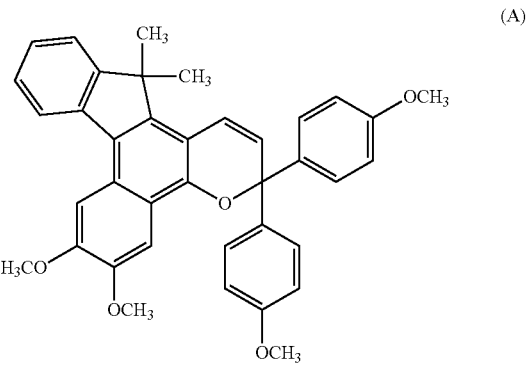 [SMILES: COc1ccc(C2(c3ccc(OC)cc3)C=Cc3c4c(c5cc(OC)c(OC)cc5c3O2)-c2ccccc2C4(C)C)cc1]

(A)

A chromene compound represented by the following formula (B) (refer to a pamphlet of International Laid-Open WO2003/044022) has low double peak characteristic with a smaller absorption at 430 to 530 nm than an absorption at 550 to 650 nm.

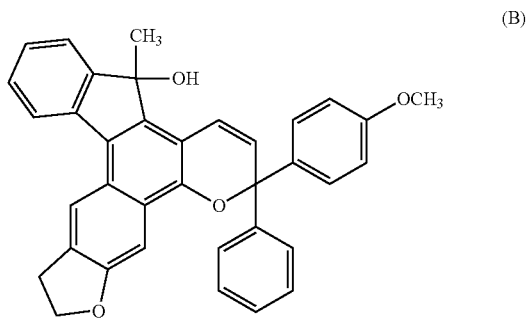 [SMILES: COc1ccc(C2(c3ccccc3)C=Cc3c4c(c5cc6c(cc5c3O2)OCC6)-c2ccccc2C4(C)O)cc1]

(B)

A chromene compound represented by the following formula (C) (refer to a pamphlet of International Laid-Open WO2005/028465) has slightly strong initial coloration as the end of its absorption spectrum (to be referred to as "absorption end" hereinafter) goes beyond 420 nm into the visible range though it has excellent double peak characteristic and practical levels of color optical density and fading speed. Therefore, this chromene compound has room for the improvement of this point.

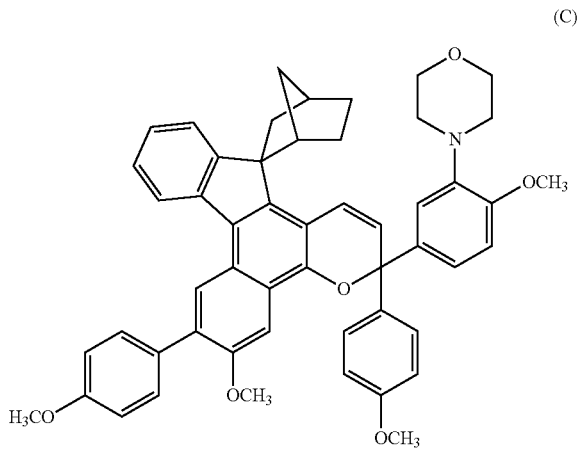 [SMILES: COc1ccc(-c2cc3c4c(c5c(c3cc2OC)OC(c2ccc(OC)cc2)(c2ccc(OC)c(N3CCOCC3)c2)C=C5)C2(CC3CCC2C3)c2ccccc2-4)cc1]

(C)

A chromene compound represented by the following formula (D) (refer to a pamphlet of International Laid-Open WO2011/016582) has excellent double peak characteristic and practical levels of color optical density and fading speed. However, characteristic properties required for photochromic compounds are becoming higher and higher. Since requirements for both of color optical density and fading speed are particularly high, the further improvement of the above chromene compounds is desired.

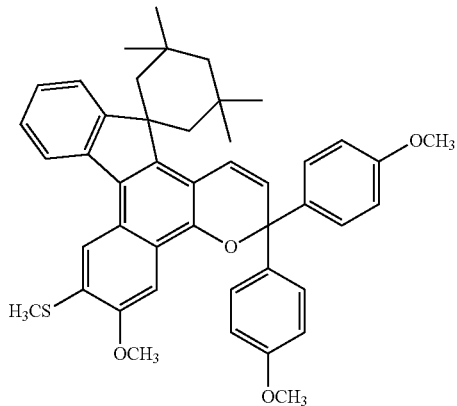

(D)

DISCLOSURE OF THE INVENTION

It is therefore an object of the present invention to provide a chromene compound which develops a color of a neutral tint and has further improved photochromic properties as compared with the above compounds.

That is, it is an object of the present invention to provide a chromene compound which has little initial coloration, high color optical density, high fading speed, is rarely colored at the time of deterioration and rarely experiences the reduction of color optical density when it is used repeatedly, that is, excellent in the durability of photochromic properties. It is another object of the present invention to provide a chromene compound which can dissolve in a monomer composition which will become a substrate for optical articles in a high concentration.

It is still another object of the present invention to provide a novel naphthol compound for the manufacture of the chromene compound of the present invention.

Other objects and advantages of the present invention will become apparent from the following description.

It is known that double peak characteristic can be improved, the absorption end can be positioned at a short wavelength range and initial coloration can be reduced by enhancing the electron donating ability of a substituent at the 6-position and/or the 7-position of an indeno(2,1-f)naphtho(1,2-b)pyran structure which is known to provide excellent photochromic properties (introduction of an electron donating group having a Harnett constant $\sigma_p$ of less than 0). Meanwhile, it is known that as the electron donating ability of the substituent at the 6-position and/or the 7-position becomes higher, the fading speed becomes lower, color development by heat at room temperature under no exposure (this color development will be referred to as "initial coloration by thermochromism" hereinafter) becomes stronger, and durability becomes lower.

The inventors of the present invention conducted intensive studies to solve the above problems and found that when a hetero ring having two hetero atoms including at least one sulfur atom is formed by two carbon atoms at the 6-position and the 7-position of the indeno(2,1-f)naphtho(1,2-b)pyran structure, a chromene compound which has high color optical density and high fading speed while retaining high double peak characteristic and also little initial coloration by thermochromism is obtained. The present invention was accomplished based on this finding.

That is, firstly, the present invention is a chromene compound having a central skeleton represented by the following formula (1).

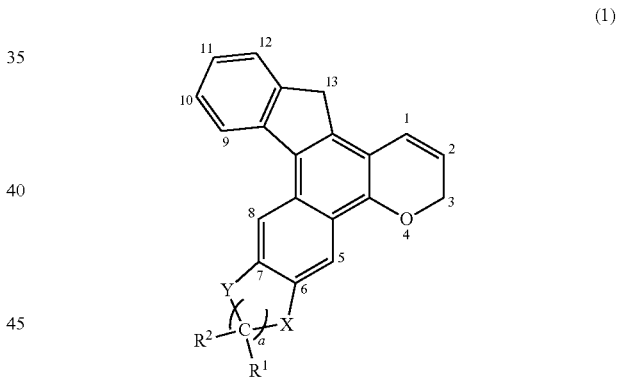

(1)

In the above formula, either one or both of X and Y are sulfur atoms, and when one of them is a sulfur atom, the other is an oxygen atom or group represented by the following formula:

($R^{12}$ is a hydrogen atom, hydroxyl group, alkyl group, haloalkyl group, cycloalkyl group, alkoxy group, halogen atom, aralkyl group, aralkoxy group, aryloxy group or aryl group),
$R^1$ and $R^2$ are each independently a hydrogen atom, hydroxyl group, alkyl group, haloalkyl group, cycloalkyl group, alkoxy group, amino group, heterocyclic group having a ring member nitrogen atom and bonded to a carbon atom bonded thereto via the nitrogen atom, cyano group, nitro group, formyl group, hydroxycarbonyl group, alkylcarbonyl group, alkoxycarbonyl group, halogen atom, aralkyl group, aralkoxy group, aryloxy group or aryl group, $R^1$ and $R^2$ may form an aliphatic ring having 3 to 20 ring member carbon atoms together with a carbon atom bonded thereto, and "a" is an integer of 1 to 3.

Secondly, the present invention is a photochromic curable composition comprising the chromene compound and polymerizable monomers.

Thirdly, the present invention is a photochromic optical article having a polymer molded product comprising the chromene compound of the present invention dispersed therein as a constituent member. In the fourth place, the present invention is an optical article having an optical substrate all or part of at least one surface of which is covered with a polymer film comprising the chromene compound of the present invention dispersed therein as a constituent member.

Finally, the present invention is a naphthol compound represented by the formula (5) which is given hereinafter.

BEST MODE FOR CARRYING OUT THE INVENTION

The chromene compound of the present invention has an indeno(2,1-f)naphtho(1,2-b)pyran structure represented by the following formula (1) as the central skeleton.

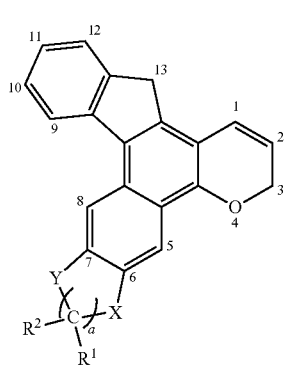

(1)

In the compound of the present invention, a hetero ring having two hetero atoms including at least one sulfur atom is condensed to the 6-position and the 7-position carbon atoms. This compound has been unknown until now. The above hetero ring introduced into the 6-position and the 7-position will be described hereinbelow.

<X and Y>

Either one or both of X and Y are sulfur atoms. When one of them is a sulfur atom, the other is an oxygen atom or group represented by the following formula.

In the above formula, $R^{12}$ is a hydrogen atom, hydroxyl group, alkyl group, haloalkyl group, cycloalkyl group, alkoxy group, halogen atom, aralkyl group, aralkoxy group, aryloxy group or aryl group.

The above alkyl group is preferably an alkyl group having 1 to 6 carbon atoms. Preferred examples of the alkyl group include methyl group, ethyl group, n-propyl group, isopropyl group, n-butyl group, sec-butyl group, tert-butyl group, pentyl group and hexyl group.

The above haloalkyl group is preferably an alkyl group having 1 to 6 carbon atoms and substituted by a fluorine atom, chlorine atom or bromine atom. Preferred examples of the haloalkyl group include trifluoromethyl group, tetrafluoroethyl group, chloromethyl group, 2-chloroethyl group and bromomethyl group.

The above cycloalkyl group is preferably a cycloalkyl group having 3 to 8 carbon atoms. Preferred examples of the cycloalkyl group include cyclopropyl group, cyclobutyl group, cyclopentyl group and cyclohexyl group.

The above alkoxy group is preferably an alkoxy group having 1 to 6 carbon atoms. Preferred examples of the alkoxy group include methoxy group, ethoxy group, n-propoxy group, isopropoxy group, n-butoxy group, sec-butoxy group and tert-butoxy group.

Examples of the above halogen atom are fluorine atom, chlorine atom, bromine atom and iodine atom.

The above aralkyl group is preferably an aralkyl group having 7 to 11 carbon atoms. Preferred examples of the aralkyl group include benzyl group, phenylethyl group, phenylpropyl group, phenylbutyl group and naphthylmethyl group.

The above aralkoxy group is preferably an aralkoxy group having 7 to 11 carbon atoms. Preferred examples of the aralkoxy group include benzyloxy group and naphthylmethoxy group.

The above aryloxy group is preferably an aryloxy group having 6 to 12 carbon atoms. Preferred examples of the aryloxy group include phenyloxy group and naphthyloxy group.

The above aryl group is preferably an aryl group having 6 to 14 carbon atoms. Preferred examples of the aryl group include phenyl group, 1-naphthyl group and 2-naphthyl group.

1 to 7 hydrogen atoms, particularly preferably 1 to 4 hydrogen atoms of the benzene or naphthalene ring of each of the aralkyl group and the aryl group may be substituted by the above hydroxyl group, alkyl group, haloalkyl group, cycloalkyl group, alkoxy group or halogen atom.

Out of these, $R^{12}$ is preferably a hydrogen atom or alkyl group as high double peak characteristic is obtained. Particularly preferred examples of $R^{12}$ include hydrogen atom, methyl group and ethyl group.

The chromene compound of the present invention has little initial coloration when X is a sulfur atom. The chromene compound of the present invention has high durability when Y is a sulfur atom.

When either one of X and Y is an oxygen atom, the chromene compound of the present invention has high fading speed. When either one of X and Y is a group represented by the following formula, the chromene compound of the present invention has high color optical density.

<$R^1$ and $R^2$>

$R^1$ and $R^2$ are each independently a hydrogen atom, hydroxyl group, alkyl group, haloalkyl group, cycloalkyl group, alkoxy group, amino group, heterocyclic group having a ring member nitrogen atom and bonded to a carbon atom bonded thereto via the nitrogen atom, cyano group, nitro group, formyl group, hydroxycarbonyl group, alkylcarbonyl group, alkoxycarbonyl group, halogen atom, aralkyl group, aralkoxy group, aryloxy group or aryl group.

The above alkyl group is preferably an alkyl group having 1 to 6 carbon atoms. Preferred examples of the alkyl group include methyl group, ethyl group, n-propyl group, isopropyl group, n-butyl group, sec-butyl group, tert-butyl group, pentyl group and hexyl group.

The above haloalkyl group is preferably an alkyl group having 1 to 6 carbon atoms and substituted by a fluorine atom, chlorine atom or bromine atom. Preferred examples of the haloalkyl group include trifluoromethyl group, tetrafluoroethyl group, chloromethyl group, 2-chloroethyl group and bromomethyl group.

The above cycloalkyl group is preferably a cycloalkyl group having 3 to 8 carbon atoms. Preferred examples of the cycloalkyl group include cyclopropyl group, cyclobutyl group, cyclopentyl group and cyclohexyl group.

The above alkoxy group is preferably an alkoxy group having 1 to 6 carbon atoms. Preferred examples of the alkoxy group include methoxy group, ethoxy group, n-propoxy group, isopropoxy group, n-butoxy group, sec-butoxy group and tert-butoxy group.

The above amino group is not limited to an amino group ($-NH_2$), and one or two hydrogen atoms of the amino group may be substituted. Examples of the substituent of the amino group include alkyl groups having 1 to 6 carbon atoms, haloalkyl groups having 1 to 6 carbon atoms, alkoxy groups having 1 to 6 carbon atoms, cycloalkyl groups having 3 to 7 carbon atoms, aryl groups having 6 to 14 carbon atoms and heteroaryl groups having 4 to 14 carbon atoms. Preferred examples of the amino group include amino group, monomethylamino group, dimethylamino group, monoethylamino group, diethylamino group, monophenylamino group and diphenylamino group.

Preferred examples of the above heterocyclic group having a ring member nitrogen atom and bonded to a carbon atom bonded thereto via the nitrogen atom include aliphatic heterocyclic groups such as morpholino group, piperidino group, pyrrolidinyl group, piperazino group and N-methylpiperazino group, and aromatic heterocyclic groups such as indolinyl group. Further, the heterocyclic group may have a substituent. A preferred example of the substituent is an alkyl group. Preferred examples of the heterocyclic group having a substituent include 2,6-dimethylmorpholino group, 2,6-dimethylpiperidino group and 2,2,6,6-tetramethylpiperidino group.

The above alkylcarbonyl group is preferably an alkylcarbonyl group having 2 to 7 carbon atoms. Preferred examples of the alkoxycarbonyl group include acetyl group and ethylcarbonyl group.

The above alkoxycarbonyl group is preferably an alkoxycarbonyl group having 2 to 7 carbon atoms. Preferred examples of the alkoxycarbonyl group include methoxycarbonyl group and ethoxycarbonyl group.

Examples of the above halogen atom are fluorine atom, chlorine atom, bromine atom and iodine atom.

The above aralkyl group is preferably an aralkyl group having 7 to 11 carbon atoms. Preferred examples of the aralkyl group include benzyl group, phenylethyl group, phenylpropyl group, phenylbutyl group and naphthylmethyl group.

The above aralkoxy group is preferably an aralkoxy group having 7 to 11 carbon atoms. Preferred examples of the aralkoxy group include benzyloxy group and naphthylmethoxy group.

The above aryloxy group is preferably an aryloxy group having 6 to 12 carbon atoms. Preferred examples of the aryloxy group include phenyloxy group and naphthyloxy group.

The above aryl group is preferably an aryl group having 6 to 14 carbon atoms. Preferred examples of the aryl group include phenyl group, 1-naphthyl group and 2-naphthyl group.

1 to 7 hydrogen atoms, particularly preferably 1 to 4 hydrogen atoms of the benzene or naphthalene ring of each of the aralkyl group, the aralkoxy group, the aryloxy group and the aryl group may be substituted by the above hydroxyl group, alkyl group, haloalkyl group, cycloalkyl group, alkoxy group, amino group, heterocyclic group, cyano group, nitro group, formyl group, hydroxycarbonyl group, alkylcarbonyl group, alkoxycarbonyl group or halogen atom.

$R^1$ and $R^2$ may form an aliphatic ring having 3 to 20 ring member carbon atoms together with the carbon atom bonded thereto. Examples of the above aliphatic ring include cyclopentane ring, cyclohexane ring, cycloheptane ring and cyclooctane ring. The aliphatic ring is particularly preferably a cyclohexane ring out of these. 1 to 6 hydrogen atoms, particularly preferably 1 to 4 hydrogen atoms of the ring may be substituted by an alkyl group having 1 to 6 carbon atoms. To improve heat resistance, the aliphatic ring is preferably substituted by an alkyl group, and preferred examples thereof include 2,2-dimethylcyclopentane ring, 2,2-dimethylcyclohexane ring and 2,2,6,6-tetramethylcyclohexane ring.

<Preferred $R^1$ and $R^2$>

$R^1$ and $R^2$ in the present invention are each preferably a hydrogen atom, alkyl group, haloalkyl group, cycloalkyl group, aryl group or group which forms a ring together with the carbon atom bonded to $R^1$ and $R^2$. $R^1$ and $R^2$ are particularly preferably the same from the viewpoint of ease of synthesis.

In order to achieve excellent photochromic properties, it is preferred that the chromene compound of the present invention should have the above preferred $R^1$ and $R^2$ as substituents. $R^1$ and $R^2$ are particularly preferably steric bulky groups in order to improve the heat resistance of an optical article containing the chromene compound of the present invention. The heat resistance of an optical article will be detailed hereinbelow.

When an optical article containing an organic compound such as a chromene compound (for example, a photochromic plastic lens) is kept at a high temperature of 100° C. or higher for a long time, it is gradually colored yellow or may change its developed color (discolor) according to the circumstances. This is considered to be because the organic compound contained in the optical article is deteriorated by oxidation. Particularly in an organic compound containing a sulfur atom, it is considered that the sulfur atom is readily oxidized to form a sulfoxide ($-SO-$) or a sulfone ($-SO_2-$). Therefore, heat resistance as used herein can be also called "oxidation resistance". When the inventors of the present invention conducted intensive studies to improve this oxidation resistance, they found that when a steric bulky substituent or a substituent which reduces electron density on a sulfur atom such as an aryl group is used as $R^1$ and $R^2$ in the present invention, the oxidation resistance of the optical article containing the chromene compound of the present invention is improved and the stability at a high temperature is greatly improved. It is considered that as the substituent is more bulky, steric hindrance becomes higher with the result that the oxidation degradation reaction of a sulfur atom hardly occurs, thereby improving oxidation resistance.

The bulkiness of the substituent can be estimated by obtaining the surface area of a sulfur atom which can be checked from a position where an oxygen atom is bonded to the sulfur atom by means of commercially available molecule drawing software. Although the surface area changes by each substituent, a substituent which reduces the surface area can improve heat resistance (oxidation resistance) effectively. For example, the surface area of a sulfur atom can be calculated by using the ChemPropStd of ChemBio3D (Version 11.0) of Cambridge Software Co., Ltd.

Further, when $R^1$ and $R^2$ are bulky substituents, double peak characteristic can also be improved in addition to the above heat resistance. Although the reason for this is unknown, when a bulky substituent such as a secondary alkyl group or tertiary alkyl group is used as $R^1$ and $R^2$, as shown in Examples, the effect of improving double peak characteristic is obtained as well.

For the above reason, $R^1$ and $R^2$ are preferably sterically bulky groups in order to improve the heat resistance of an optical article containing the chromene compound of the present invention.

The alkyl group is preferably an alkyl group having 1 to 6 carbon atoms, more preferably a branched alkyl group having 3 to 6 carbon atoms. Particularly preferred examples of the alkyl group include isopropyl group, isobutyl group and tert-butyl group.

The cycloalkyl group is preferably a cycloalkyl group having 3 to 8 carbon atoms, particularly preferably cyclopentyl group or cyclohexyl group.

The aryl group is preferably an aryl group having 6 to 20 carbon atoms. This aryl group may have a substituent, preferably an alkyl group having 1 to 6 carbon atoms. More specifically, the aryl group is preferably a naphthyl group or phenyl group and may be a naphthyl group having an alkyl group with 1 to 6 carbon atoms or a phenyl group having an alkyl group having 1 to 6 carbon atoms as a substituent. It is particularly preferably a group having an alkyl group with 1 to 6 carbon atoms at the ortho-position of a phenyl group, most preferably a 2-methylphenyl group having a methyl group at the ortho-position of a phenyl group.

When $R^1$ and $R^2$ form a ring together with the carbon atom bonded thereto, the formed ring is preferably an aliphatic ring having 3 to 6 carbon atoms. This aliphatic ring may have a substituent, preferably an alkyl group having 1 to 6 carbon atoms. Specific examples thereof include cyclopentane ring, cyclohexane ring, cyclopentane ring having a substituent with 1 to 6 carbon atoms and cyclohexane ring having a substituent with 1 to 6 carbon atoms. In the cyclohexane ring or cyclopentane ring, an alkyl group having 1 to 6 carbon atoms may be bonded to a carbon atom adjacent to the carbon atom bonded to $R^1$ and $R^2$. It is particularly preferably a ring having two alkyl groups with 1 to 6 carbon atoms bonded to the carbon atom. The alkyl group as a substituent is preferably a methyl group. Specific examples of the aliphatic ring include 2,2-dimethylcyclohexane ring, 2,2,6,6-tetramethylcyclohexane ring, 2,2-dimethylcyclopentane ring and 2,2,6,6-tetramethylcyclopentane ring.

<"a">

"a" is an integer of 1 to 3. When "a" is 2 or more, a plurality of groups represented by the following formula may be the same or different. "a" is preferably 1 or 2, particularly preferably 1 as high color optical density and high fading speed can be obtained at the same time.

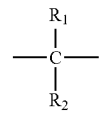

<Preferred Hetero Ring>

Particularly preferred hetero rings are enumerated below. In the following formulas, the carbon atoms at positions denoted by 6 and 7 are the 6-position and 7-position carbon atoms in the above formula (1).

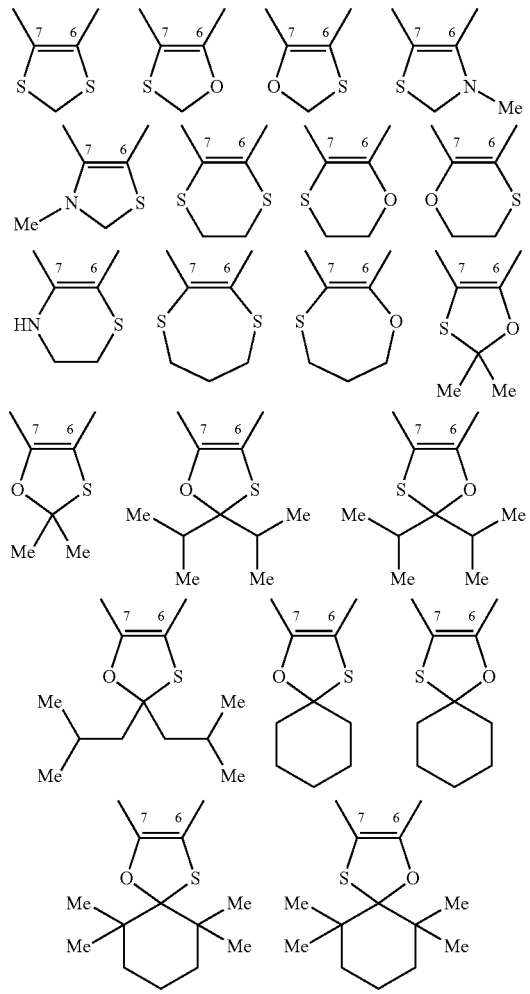

In the chemical formulas in this text, as a matter of course, Me signifies a methyl group.

<Preferred Chromene Compound>

Out of the chromene compounds of the present invention, a chromene compound represented by the following formula (2) is preferred as it develops a color of a neutral tint and has high color optical density, high fading speed and excellent durability of photochromic properties.

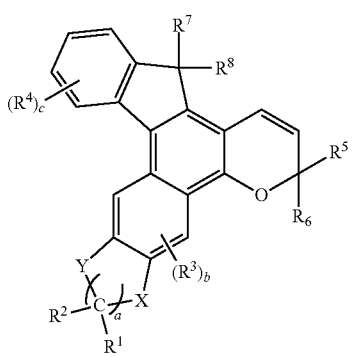

(2)

The substituents of the chromene compound represented by the above formula (2) will be explained hereinbelow.

<X, Y, R¹, R² and "a">

X, Y, R¹, R² and "a" are as defined in the formula (1) and explained above.

<R³ and R⁴>

R³ and R⁴ are each independently a hydroxyl group, alkyl group, haloalkyl group, cycloalkyl group, alkoxy group, amino group, heterocyclic group having a ring member nitrogen atom and bonded to a benzene ring (carbon atom) bonded thereto via the nitrogen atom, cyano group, nitro group, formyl group, hydroxycarbonyl group, alkylcarbonyl group, alkoxycarbonyl group, halogen atom, aralkyl group, aralkoxy group, aryloxy group, aryl group, alkylthio group, cycloalkylthio group, arylthio group or group having a siloxane bond.

The above alkyl group is preferably an alkyl group having 1 to 6 carbon atoms. Preferred examples of the alkyl group include methyl group, ethyl group, n-propyl group, isopropyl group, n-butyl group, sec-butyl group, tert-butyl group, pentyl group and hexyl group.

The above haloalkyl group is preferably an alkyl group having 1 to 6 carbon atoms and substituted by a fluorine atom, chlorine atom or bromine atom. Preferred examples of the haloalkyl group include trifluoromethyl group, tetrafluoroethyl group, chloromethyl group, 2-chloroethyl group and bromomethyl group.

The above cycloalkyl group is preferably a cycloalkyl group having 3 to 8 carbon atoms. Preferred examples of the cycloalkyl group include cyclopropyl group, cyclobutyl group, cyclopentyl group and cyclohexyl group.

The above alkoxy group is preferably an alkoxy group having 1 to 6 carbon atoms. Preferred examples of the alkoxy group include methoxy group, ethoxy group, n-propoxy group, isopropoxy group, n-butoxy group, sec-butoxy group and tert-butoxy group.

The above amino group is not limited to an amino group (—NH₂), and one or two hydrogen atoms of the amino group may be substituted. Examples of the substituent of the amino group include alkyl groups having 1 to 6 carbon atoms, haloalkyl groups having 1 to 6 carbon atoms, alkoxy groups having 1 to 6 carbon atoms, cycloalkyl groups having 3 to 7 carbon atoms, aryl groups having 6 to 14 carbon atoms and heteroaryl groups having 4 to 14 carbon atoms. Preferred examples of the amino group include amino group, methylamino group, dimethylamino group, ethylamino group, diethylamino group, phenylamino group and diphenylamino group.

Preferred examples of the above heterocyclic group having a ring member nitrogen atom and bonded to a benzene ring bonded thereto via the nitrogen atom include aliphatic heterocyclic groups such as morpholino group, piperidino group, pyrrolidinyl group, piperazino group and N-methylpiperazino group, and aromatic heterocyclic groups such as indolinyl group. Further, the heterocyclic group may have a substituent. A preferred example of the substituent is an alkyl group. Preferred examples of the heterocyclic group having a substituent include 2,6-dimethylmorpholino group, 2,6-dimethylpiperidino group and 2,2,6,6-tetramethylpiperidino group.

The above alkylcarbonyl group is preferably an alkylcarbonyl group having 2 to 7 carbon atoms. Preferred examples of the alkylcarbonyl group include acetyl group and ethylcarbonyl group.

The above alkoxycarbonyl group is preferably an alkoxycarbonyl group having 2 to 7 carbon atoms. Preferred examples of the alkoxycarbonyl group include methoxycarbonyl group and ethoxycarbonyl group.

Examples of the above halogen atom are fluorine atom, chlorine atom, bromine atom and iodine atom.

The above aralkyl group is preferably an aralkyl group having 7 to 11 carbon atoms. Preferred examples of the aralkyl group include benzyl group, phenylethyl group, phenylpropyl group, phenylbutyl group and naphthylmethyl group.

The above aralkoxy group is preferably an aralkoxy group having 7 to 11 carbon atoms. Preferred examples of the aralkoxy group include benzyloxy group and naphthylmethoxy group.

The above aryloxy group is preferably an aryloxy group having 6 to 12 carbon atoms. Preferred examples of the aryloxy group include phenyloxy group and naphthyloxy group.

The above aryl group is preferably an aryl group having 6 to 14 carbon atoms. Preferred examples of the aryl group include phenyl group, 1-naphthyl group and 2-naphthyl group.

1 to 7 hydrogen atoms, particularly preferably 1 to 4 hydrogen atoms of the benzene or naphthalene ring of each of the aralkyl group, the aralkoxy group, the aryloxy group and the aryl group may be substituted by the above hydroxyl group, alkyl group, haloalkyl group, cycloalkyl group, alkoxy group, amino group, heterocyclic group, cyano group, nitro group, formyl group, hydroxylcarbonyl group, alkylcarbonyl group, alkoxycarbonyl group or halogen atom.

The above alkylthio group is preferably an alkylthio group having 1 to 6 carbon atoms. Preferred examples of the alkylthio group include methylthio group, ethylthio group, n-propylthio group, isopropylthio group, n-butylthio group, sec-butylthio group and t-butylthio group.

The above cycloalkylthio group is preferably a cycloalkylthio group having 3 to 8 carbon atoms. Preferred examples of the cycloalkylthio group include cyclopropylthio group, cyclobutylthio group, cyclopentylthio group and cyclohexylthio group.

The above arylthio group is preferably an arylthio group having 6 to 10 carbon atoms. Preferred examples of the arylthio group include phenylthio group, 1-naphthylthio group and 2-naphthylthio group.

1 to 9 hydrogen atoms, particularly preferably 1 to 4 hydrogen atoms of each of the arylthio group and the heteroarylthio group may be substituted by an alkyl group having 1 to 6 carbon atoms, alkoxy group having 1 to 6 carbon atoms, cycloalkyl group having 3 to 8 carbon atoms or halogen atom.

The above group having a siloxane bond should have a Si—O bond and is preferably a group represented by the following formula (G).

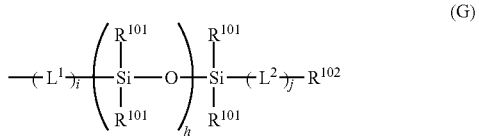

(wherein, $R^{101}$'s are each independently an alkyl group or aryl group, $R^{102}$ is a hydrogen atom, hydroxyl group, hydroxycarbonyl group, alkyl group, haloalkyl group, alkylcarbonyl group, alkoxycarbonyl group, acryloyl group, methacryloyl group or vinyl group, $L^1$ and $L^2$ are each independently a divalent group, "h" is an integer of 2 to 100, "i" is an integer of 1 to 10, and "j" is an integer of 1 to 10.)

In the above formula (G), the alkyl group, the aryl group, the hydroxycarbonyl group and the haloalkyl group are the same as those explained above.

In the above formula (G), $L^1$ and $L^2$ are each a divalent group selected from alkylene group having 1 to 20 carbon atoms, phenylene group (—O—), oxygen atom (—O—), sulfur atom (—S—) and carbonyl group (—C(=O)—).

"h" is an integer of 2 to 100 indicative of the number of siloxane units in the above formula (G).

"i" and "j" are each an integer of 1 to 10 indicative of the numbers of divalent groups $L^1$'s and $L^2$'s, respectively. When "i" or "j" is an integer of 2 or more, a plurality of $L^1$'s or a plurality of $L^2$'s may be the same or different.

"b" is an integer of 0 to 2 indicative of the number of $R^3$'s. When "b" is 2, two $R^3$'s may be the same or different. "c" is an integer of 0 to 4 indicative of the number of $R^4$'s. When "c" is an integer of 2 to 4, a plurality of $R^4$'s may be the same or different.

Out of the above groups, $R^3$ is preferably a sterically small substituent as high fading speed is obtained. Particularly preferred $R^3$ is a hydrogen atom ("b"=0).

Meanwhile, $R^4$ is preferably a hydrogen atom ("c"=0), haloalkyl group or cyano group as high fading speed is obtained. Preferred examples of $R^4$ include hydrogen atom, trifluoromethyl group and cyano group. To obtain higher fading speed, $R^4$ is preferably bonded to the 11-position carbon atom.

Even when a plurality of $R^3$'s and a plurality of $R^4$'s are existent, preferred $R^3$'s and $R^4$'s are the same as those explained above.

<$R^5$ and $R^6$>

$R^5$ and $R^6$ are each independently a group represented by the following formula (3), group represented by the following formula (4), aryl group, heteroaryl group or alkyl group.

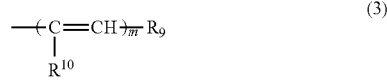

$R^9$ in the above formula (3) is an aryl group or heteroaryl group. The aryl group is the same as that explained for $R^3$ and $R^4$.

The above heteroaryl group is not particularly limited but preferably a heteroaryl group comprising an aromatic ring having 5 to 7 ring members and containing 1 to 2 oxygen atoms, nitrogen atoms or sulfur atoms or a condensed ring thereof with a benzene ring. The heteroaryl group is bonded to the benzene ring of the basic skeleton via a carbon atom.

Preferred examples of the heteroaryl group include thienyl group, furyl group, pyrrolinyl group, pyridyl group, benzothienyl group, benzofuranyl group and benzopyrrolinyl group.

1 to 7 hydrogen atoms, particularly preferably 1 to 4 hydrogen atoms of the heteroaryl group may be substituted by the above hydroxyl group, alkyl group, haloalkyl group, cycloalkyl group, alkoxy group, amino group, heterocyclic group having a nitrogen atom and bonded to a heteroaryl group via the nitrogen atom, cyano group, nitro group, formyl group, hydroxycarbonyl group, alkylcarbonyl group, alkoxycarbonyl group or halogen atom.

$R^{10}$ is a hydrogen atom; alkyl group or halogen atom. Preferred examples of the alkyl group include methyl group, ethyl group and propyl group. Examples of the halogen atom are fluorine atom, chlorine atom, bromine atom and iodine atom.

"m" is an integer of 1 to 3. "m" is preferably 1 from the viewpoint of the acquisition of raw materials.

Preferred examples of the group represented by the above formula (3) include phenyl-ethenyl group, (4-(N,N-dimethylamino)phenyl)-ethenyl group, (4-morpholinophenyl)-ethenyl group, (4-piperidinophenyl)-ethenyl group, (4-methoxyphenyl)-ethenyl group, (2-methoxyphenyl)-ethenyl group, phenyl-1-methylethenyl group, (4-methoxyphenyl)-1-methylethenyl group, phenyl-1-fluoroethenyl group, (4-(N,N,-dimethylamino)phenyl)-1-fluoroethenyl group, 2-thienyl-ethenyl group, 2-furyl-ethenyl group, 2-(N-methyl)pyrrolinyl-ethenyl group, 2-benzothienyl-ethenyl group, 2-benzofuranyl-ethenyl group and 2-(N-methyl)indolyl-ethenyl group.

In the above formula (4), $R^{11}$ is an aryl group or heteroaryl group. It is understood that these groups are the same as those explained for $R^9$. "n" is an integer of 1 to 3. From the viewpoint of the acquisition ease of raw materials, "n" is preferably 1.

Preferred examples of the group represented by the above formula (4) include phenyl-ethynyl group, (4-(N,N-dimethylamino)phenyl)-ethynyl group, (4-morpholinophenyl)-ethynyl group, (4-piperidinophenyl)-ethynyl group, (4-methoxyphenyl)-ethynyl group, (4-methylphenyl)-ethynyl group, (2-methoxyphenyl)-ethynyl group, 2-thienyl-ethynyl group, 2-furyl-ethynyl group, 2-(N-methyl)pyrrolinyl-ethynyl group, 2-benzothienyl-ethyl group, 2-benzofuranyl-ethynyl group and 2-(N-methyl)indolyl-ethynyl group, Examples of the aryl group or the alkyl group represented by $R^5$ and $R^6$ are the same as those explained for $R^3$ and $R^4$.

Examples of the heteroaryl group represented by $R^5$ and $R^6$ are the same as those explained for $R^9$.

$R^5$ and $R^6$ may form an aliphatic hydrocarbon ring together with the carbon atom bonded thereto. Preferred examples of the aliphatic hydrocarbon ring include adamantane ring, bicyclononane ring, norbornane ring and fluorene ring.

In order for the chromene compound of the above formula (2) to exhibit particularly excellent photochromic properties (double peak characteristic and fading speed), at least one, preferably both of $R^5$ and $R^6$ are aryl groups or heteroaryl groups. Further, at least one, preferably both of $R^5$ and $R^6$ are each any one of the following groups (i) to (iii):

(i) an aryl group or heteroaryl group having an alkyl group or alkoxy group as a substituent;

(ii) an aryl group or heteroaryl group having an amino group as a substituent;

(iii) an aryl group or heteroaryl group having a heterocyclic group which has a nitrogen atom as a ring member hetero atom and is bonded to an aryl group or heteroaryl group via the nitrogen atom as a substituent; and (iv) an aryl group or heteroaryl group having a group with a siloxane bond as a substituent.

The positions and the total number of substituents substituting the aryl group or heteroaryl group in (i) to (iv) are not particularly limited. In order to exhibit excellent photochromic properties, when the aryl group is a phenyl group, preferably, the substitution position is the 3-position or the 4-position, and the number of substituents is 1. A group having an alkyl group, alkoxy group, amino group, heterocyclic group having a ring member nitrogen atom and bonded to a benzene ring bonded thereto vi the nitrogen atom or aryl group substituting the 3-position or the 4-position of the phenyl group is particularly preferred.

Preferred examples of this aryl group include 4-methylphenyl group, 4-methoxyphenyl group, 3,4-dimethoxyphenyl group, 4-n-propoxyphenyl group, 4-(N,N-dimethylamino)phenyl group, 4-(N,N-diethylamino)phenyl group, 4-(N,N-diphenylamino)phenyl group, 4-morpholinophenyl group, 4-piperidinophenyl group, 3-(N,N-dimethylamino) phenyl group and 4-(2,6-dimethylpiperidino)phenyl group.

The positions and the total number of substituents substituting the heteroaryl group in (i) to (iv) are not particularly limited. The number of the substituents is preferably 1. Preferred examples of the heteroaryl group include 4-methoxythienyl group, 4-(N,N-dimethylamino)thienyl group, 4-methylfuryl group, 4-(N,N-diethylamino)furyl group, 4-(N,N-diphenylamino)thienyl group, 4-morpholinopyrrolinyl group, 6-piperidinobenzothienyl group and 6-(N,N-dimethylamino)benzofuranyl group.

($R^7$ and $R^8$)

$R^7$ and $R^8$ are each independently a hydrogen atom, hydroxyl group, alkyl group, haloalkyl group, cycloalkyl group, alkoxy group, alkoxyalkyl group, formyl group, hydroxycarbonyl group, alkylcarbonyl group, alkoxycarbonyl group, halogen atom, aralkyl group, aralkoxy group, aryloxy group or aryl group.

The alkyl group, the haloalkyl group, the cycloalkyl group, the alkoxy group, the alkycarbonyl group, the alkoxycarbonyl group, the halogen atom, the aralkyl group, the aralkoxy group, the aryloxy group and the aryl group are the same as those explained for $R^3$ and $R^4$.

The above alkoxyalkyl group is preferably an alkoxyalkyl group having 2 to 7 carbon atoms. Preferred examples thereof include methoxymethyl group, methoxyethyl group, methoxy-n-propyl group, methoxy-n-butyl group, ethoxyethyl group and n-propoxypropyl group.

$R^7$ and $R^8$ may form an aliphatic ring having 3 to 20 ring member carbon atoms, condensed polycyclic ring having an aromatic ring or aromatic hetero ring condensed to the above aliphatic ring, hetero ring having 3 to 20 ring member atoms, or condensed polycyclic ring having an aromatic ring or aromatic hetero ring condensed to the above hetero ring, together with the 13-position carbon atom bonded thereto.

Examples of the above aliphatic ring include cyclopentane ring, cyclohexane ring, cyclooctane ring, cycloheptane ring, norbornane ring, bicyclononane ring and adamantane ring.

Examples of the above condensed polycyclic ring having an aromatic ring or aromatic hetero ring condensed to the above aliphatic ring include phenanthrene ring.

Examples of the above hetero ring include thiophene ring, furan ring and pyridine ring.

Examples of the above condensed polycyclic ring having an aromatic ring or aromatic hetero ring condensed to the above hetero ring include phenylfuran ring and biphenylthiophene ring.

<Particularly Preferred $R^7$ and $R^8$>

In the present invention, preferred substituents $R^7$ and $R^8$ are each a hydroxyl group, alkyl group, alkoxy group or group which forms a ring together with the 13-position carbon atom bonded thereto. An example of the alkyl group is a methyl group and an example of the alkoxy group is a methoxy group. To reduce initial coloration by thermochromism and increase the fading speed while retaining high double peak characteristic, out of the above preferred substituents, $R^7$ and $R^8$ are preferably substituents which form a ring together with the 13-position carbon atom bonded thereto. They are more preferably substituents which form the above aliphatic ring or the above condensed polycyclic ring having an aromatic ring or aromatic hetero ring condensed to the above aliphatic ring as the fading speed in particular becomes high. They are particularly preferably substituents which form the above aliphatic ring as initial coloration by thermochromism is reduced.

The aliphatic ring formed by $R^7$ and $R^8$ is particularly preferably an unsubstituted aliphatic hydrocarbon ring or an aliphatic hydrocarbon ring having at least one substituent selected from the group consisting of alkyl group, haloalkyl group, cycloalkyl group, alkoxy group, amino group, aralkyl group, aryl group and halogen atom. The alkyl group, the haloalkyl group, the cycloalkyl group, the alkoxy group, the amino group, the aralkyl group, the aryl group and the halogen atom are the same as those explained for $R^3$ and $R^4$.

More preferred examples of the aliphatic hydrocarbon ring include monocyclic rings such as cyclohexane ring, cyclooctane ring and cycloheptane ring, bicyclo rings such as norbornane ring, bicyclo[3,2,1]octane ring, bicyclo[4,2,0]octane ring, bicyclo[3,3,0]octane ring, bicyclo[3,3,1]nonane ring, bicyclo[4,3,0]nonane ring and bicyclo[6,3,0]undecane ring, tricyclo rings such as adamantane ring, and rings obtained by substituting these rings by at least one lower alkyl group having 4 or less carbon atoms such as methyl group. Out of these, monocyclic rings or bicycle rings exhibit a particularly excellent effect as initial coloration by thermochromism is reduced while high double peak characteristic and high fading speed are retained.

In the present invention, most preferred typical examples of the monocyclic ring formed by bonding $R^7$ and $R^8$ include rings represented by the following formulas. In the following formulas, the carbon atom denoted by 13 is the 13-position carbon atom.

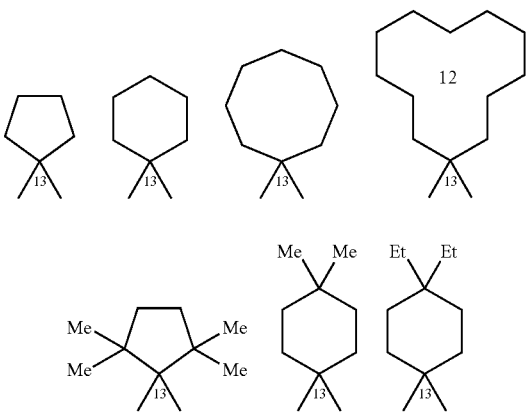

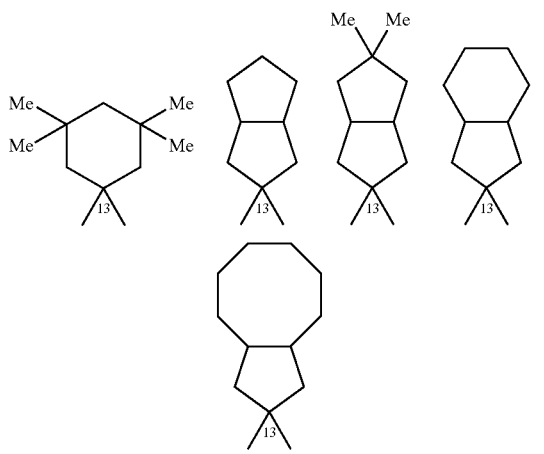
Out of the above monocyclic rings, a cyclooctane ring, 3,3,5,5-tetramethylcyclohexane ring, 4,4-diethylcyclohexane ring, 4,4-dimethylcyclohexane ring and bicyclo[4,3,0]nonane ring are most preferred.
<Particularly Preferred Chromene Compound>
Particularly preferred examples of the chromene compound in the present invention include the following compounds.
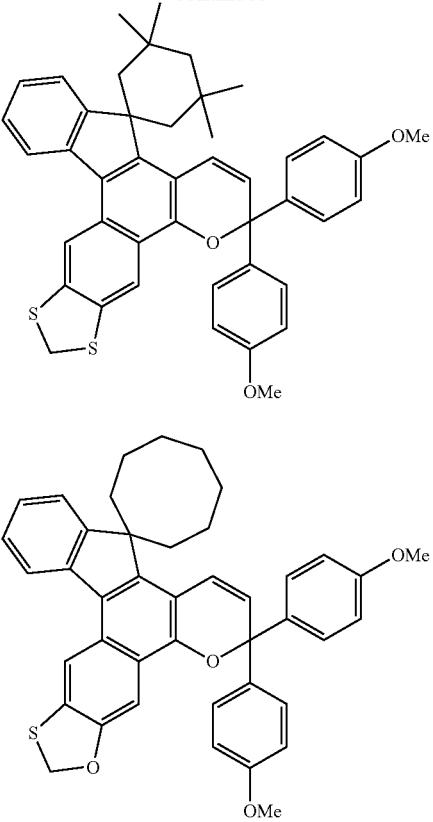
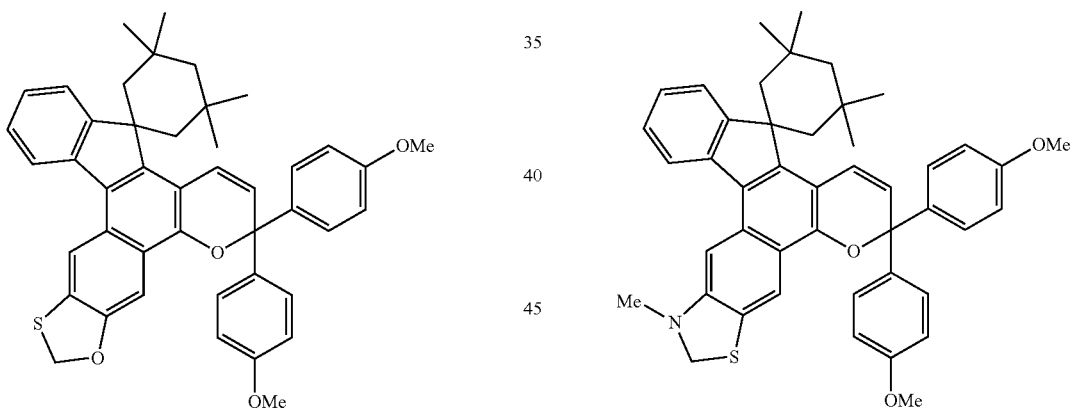
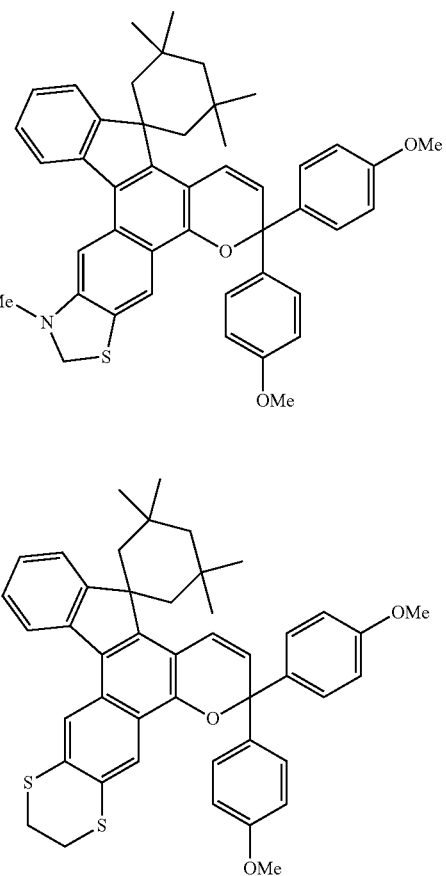

-continued

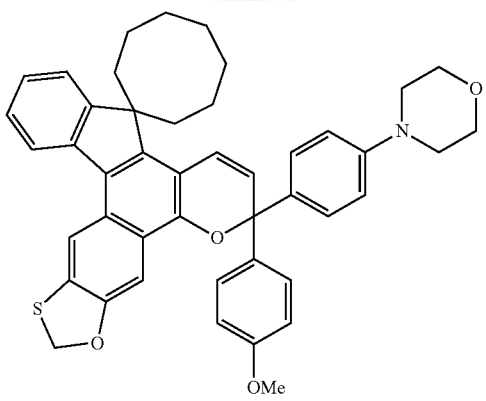

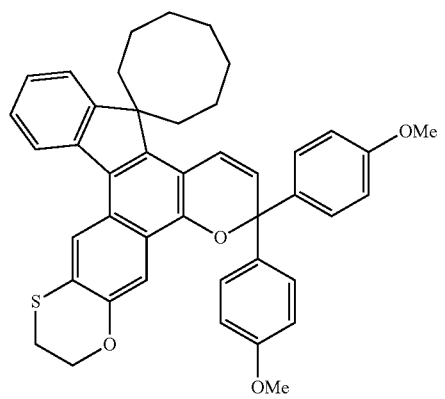

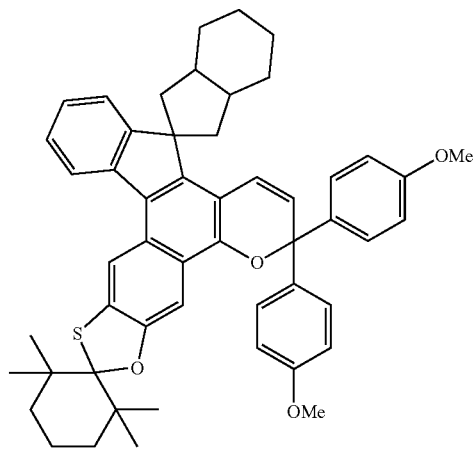

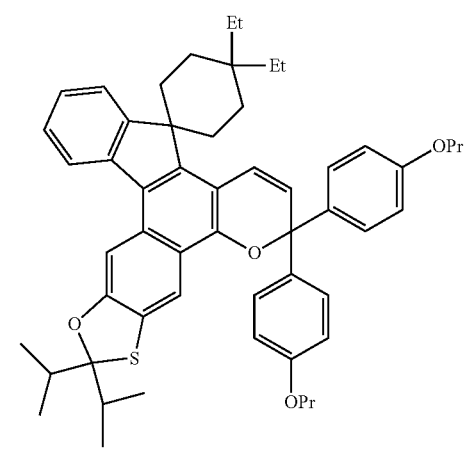

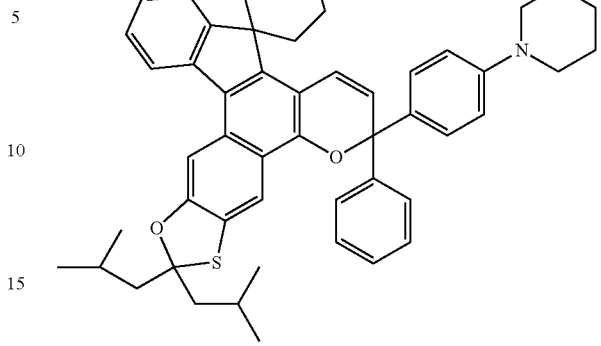

In the chemical formulas of this text including the above formulas, Me denotes a methyl group, Et denotes an ethyl group, and Pr denotes a propyl group.

(Identification of Chromene Compound)

The chromene compound of the present invention is generally existent as an achromatic, light yellow or light green solid or viscous liquid at normal temperature and normal pressure and can be confirmed by the following means (1) to (3).

(1) When the proton nuclear magnetic resonance spectrum ($^1$H-NMR) of the chromene compound is measured, peaks based on an aromatic proton and an alkene proton appear at δ of around 5.0 to 9.0 ppm and peaks based on the protons of an alkyl group and an alkylene group appear at δ of around 0.5 to 4.9 ppm. By comparing these spectral intensities relatively, the number of the protons of bonds can be known. In the above formula (1), when a hetero ring containing X and Y is a 5-membered ring (that is, a=1) and $R^1$ and/or $R^2$ are/is a hydrogen atom, the peak of the hydrogen atom shifts to a lower magnetic field than usual and appears at δ of around 5.0 to 6.0 ppm.

(2) The composition of a corresponding product can be determined by elemental analysis.

(3) When the $^{13}$C-nuclear magnetic resonance spectrum ($^{13}$C-NMR) of the chromene compound is measured, a peak based on the carbon of an aromatic hydrocarbon group appears at δ of around 110 to 160 ppm, peaks based on the carbons of an alkene and an alkyne appear at δ of around 80 to 140 ppm, and peaks based on the carbons of an alkyl group and an alkylene group appear at δ of around 20 to 80 ppm.

<Production of Chromene Compound>

The process for producing the chromene compound of the present invention is not particularly limited and may be any synthetic process. For example, the chromene compound represented by the above formula (2) can be advantageously produced by the following process.

That is, the chromene compound can be advantageously produced by reacting a naphthol compound represented by the following formula (5) with a propargyl alcohol compound represented by the following formula (6) in the presence of an acid catalyst.

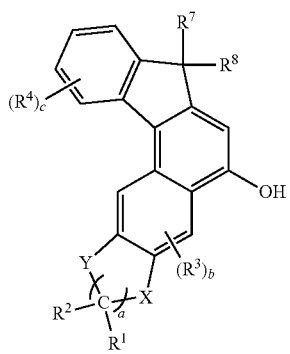

(5)

(In the above formula, X, Y, $R^1$, $R^2$, $R^3$, $R^4$, $R^7$, $R^8$, "a", "b" and "c" are as defined in the above formula (2).)

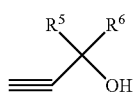

(6)

(In the above formula, $R^5$ and $R^6$ are as defined in the above formula (2).)

The reaction ratio of the naphthol compound to the propargyl alcohol compound is selected from a wide range, preferably a range from 1:10 to 10:1 (molar ratio). Sulfuric acid, benzenesulfonic acid, p-toluenesulfonic acid or acid alumina is used as the acid catalyst in an amount of 0.1 to 10 parts by weight based on 100 parts by weight of the total of the naphthol compound and the propargyl alcohol compound. The reaction temperature is preferably 0 to 200° C. An aprotic organic solvent such as N-methylpyrrolidone, dimethyl formamide, tetrahydrofuran, benzene or toluene is preferably used as the solvent. The method of purifying the product obtained through the above reaction is not particularly limited. For example, the obtained product may be purified by carrying out silica gel column purification and further recrystallization.

The naphthol compound represented by the above formula (5) is provided as a novel compound by the present invention. In the formula (5), X, Y, $R^1$, $R^2$, $R^3$, $R^4$, $R^7$, $R^8$, "a", "b" and "c" are as defined in the above formula (2). Therefore, it should be understood that the above explanation of the formula (2) is directly applied to these groups and parts.

In the present invention, preferred examples of the naphthol compound represented by the formula (5) include the following compounds.

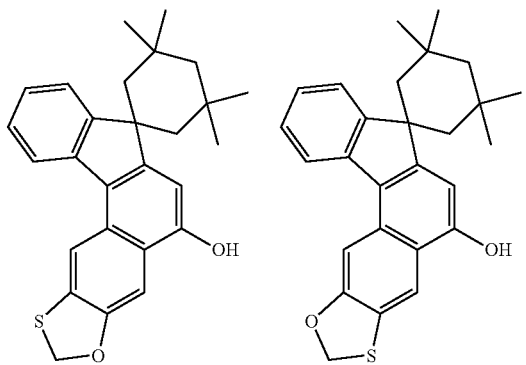

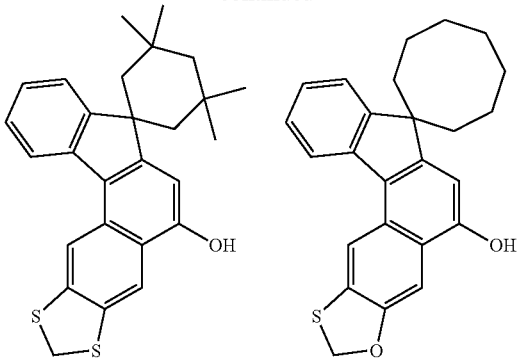

-continued

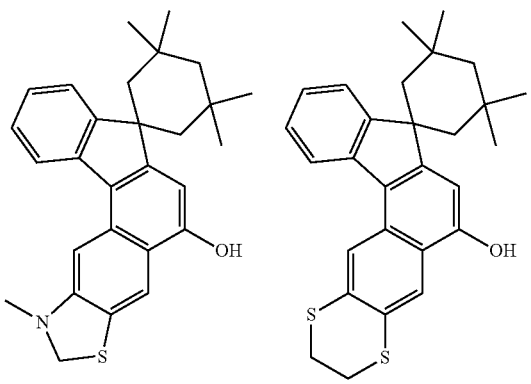

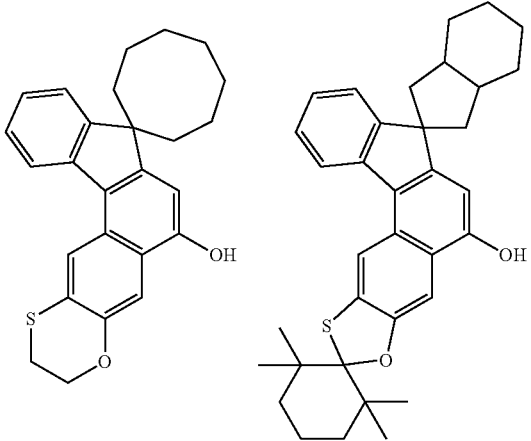

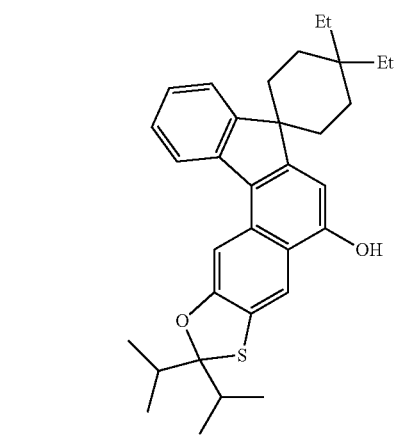

-continued

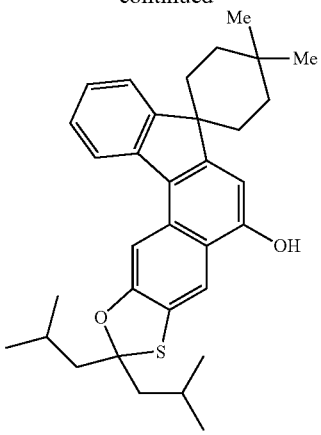

Ordinary naphthol compounds can be synthesized in accordance with reaction methods described in, for example, research papers such as Journal of Organic Chemistry 69(10) 3282-3293; 2004, Synthetic Communications 23(16)2241-2249 (1993) and WO01/60881.

<Method of Synthesizing Naphthol Compound>

Although the method of synthesizing the naphthol compound represented by the above formula (5) is not particularly limited, the naphthol compound can be synthesized as follows, for example.

To begin with, a benzene compound represented by the following formula (7) may be purchased as a commercial product or may be synthesized based on the following document.

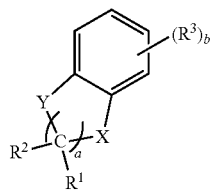
(7)

In the above formula (7), X, Y, $R^1$, $R^2$, $R^3$, "a" and "b" are as defined in the above formula (2).

For example, a benzene compound represented by the following formula (8) can be synthesized in accordance with a reaction method described in research papers such as Tetrahedron 59(24). 4383-4388 (2003).

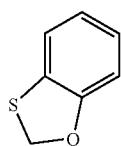
(8)

Thereafter, the compound (7) as a raw material is reacted with acid chloride to obtain a compound represented by the following formula (9).

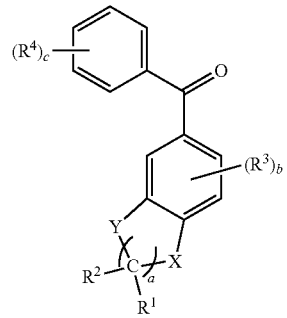
(9)

In the above formula (9), $R^4$ and "c" are as defined in the above formula (2).

Further, the above compound (9) is subjected to a Stobbe reaction and a cyclization reaction to obtain a compound represented by the following formula (10).

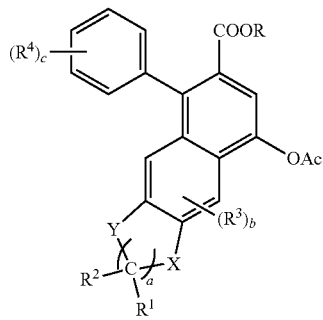
(10)

In the compound of the formula (10), R is a group derived from a diester compound used in the Stobbe reaction. Then, the compound (10) is hydrolyzed by using an alkali or acid to obtain a carboxylic acid represented by the following formula (11).

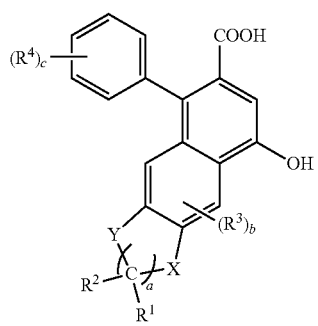
(11)

This carboxylic acid represented by the formula (11) is benzylated by using a base such as potassium carbonate and benzyl chloride and then hydrolyzed by using an alkali or acid to obtain a carboxylic acid which is represented by the following formula (12) and whose hydroxyl group is benzyl (Bn) protected.

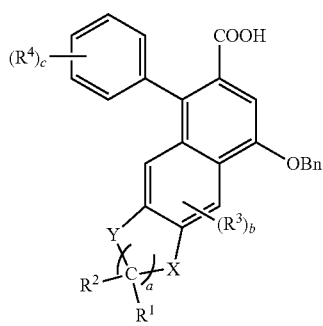

(12)

This benzyl-protected carboxylic acid represented by the above formula (12) is converted into an amine by a method such as Curtius rearrangement, Hofmann rearrangement or Lossen rearrangement, and a diazonium salt is prepared from the amine. This diazonium salt is converted into a bromide through a Sandmeyer reaction or the like, and the obtained bromide is reacted with magnesium or lithium to prepare an organic metal reagent. This organic metal reagent is reacted with a ketone represented by the following formula (13) at −10 to 70° C. in an organic solvent for 10 minutes to 4 hours to obtain a compound represented by the following formula (14).

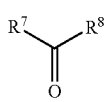

(13)

(In the above formula, $R^7$ and $R^8$ are as defined in the above formula (2).)

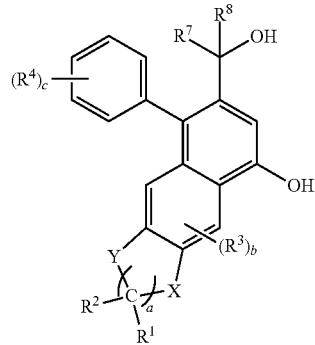

(14)

The naphthol compound of the above formula (5) of interest can be synthesized by reacting this compound (14) at 10 to 120° C. for 10 minutes to 2 hours under a neutral to acid condition to spironize the alcohol. In this reaction, the reaction ratio of the above organic metal reagent to the ketone represented by the above formula (13) is selected from a wide range, preferably a range from 1:10 to 10:1 (molar ratio). The reaction temperature is preferably −10 to 70° C. An aprotic organic solvent such as diethyl ether, tetrahydrofuran, benzene or toluene is preferably used as the solvent. The spironization of the alcohol under a neutral to acid condition is preferably carried out by using an acid catalyst such as acetic acid, hydrochloric acid, sulfuric acid, benzenesulfonic acid, p-toluenesulfonic acid or acid alumina. The acid catalyst is preferably used in an amount of 0.1 to 10 parts by weight based on 100 parts by weight of the alcohol. For this spironization, a solvent such as tetrahydrofuran, benzene or toluene is used.

(Propargyl Alcohol Compound)

The propargyl alcohol compound represented by the above formula (6) can be synthesized by various methods. For example, it can be easily synthesized by reacting a ketone compound with a metal acetylene compound such as lithium acetylide.

The chromene compound of the present invention is obtained by reacting the above naphthol compound with the propargyl alcohol compound. The obtained chromene compound dissolves well in a general-purpose organic solvent such as toluene, chloroform or tetrahydrofuran. When the chromene compound represented by the above formula (1) is dissolved in such a solvent, the obtained solution is almost achromatic and transparent and exhibits an excellent photochromic function that it develops a color swiftly upon exposure to sunlight or ultraviolet radiation and reversibly returns to its original achromatic state swiftly by blocking the light.

(Combination with Another Photochromic Compound>

Although the chromene compound of the present invention develops a color of a neutral tint by itself, it may be used in combination with another photochromic compound to obtain various colors required as a photochromic lens. The chromene compound of the present invention exhibits an excellent effect. Therefore, even when the chromene compound is mixed with another photochromic compound to carry out color control, the obtained photochromic composition exhibits an excellent effect. Therefore, any known compound may be used as the photochromic compound to be combined with. Examples of the photochromic compound include fulgide, fulgimide, spirooxazine and chromene. Out of these, a chromene compound is particularly preferred because it can keep a color uniformly at the time of color development and fading, can suppress a color drift at the time of color development due to the deterioration of photochromic properties and further can reduce initial coloration.

That is, by combining the chromene compound of the present invention with another chromene compound which has high color development sensitivity, high fading speed and little initial coloration like the above chromene compound, a photochromic composition which keeps a color uniformly at the time of color development and fading and provides high transparency can be obtained.

Preferred examples of the chromene compound to be combined with include chromene compounds' represented by the following formulas (15a) and (15b).

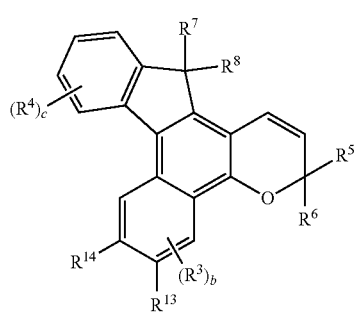

(15a)

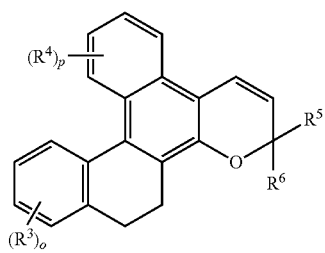
(15b)

In the above formula (15a), $R^3$, $R^4$, $R^5$, $R^6$, $R^7$ and $R^8$ are as defined in the above formula (2).

$R^{13}$ and $R^{14}$ are each independently a hydrogen atom, hydroxyl group, alkyl group, haloalkyl group, cycloalkyl group, alkoxy group, amino group, heterocyclic group having a ring member nitrogen atom and bonded to a benzene ring bonded thereto via the nitrogen atom, cyano group, nitro group, formyl group, hydroxycarbonyl group, alkylcarbonyl group, alkoxycarbonyl group, halogen atom, aralkyl group, aralkoxy group, aryloxy group, aryl group, alkylthio group, cycloalkylthio group or arylthio group.

The alkyl group, the haloalkyl group, the cycloalkyl group, the alkoxy group, the amino group, the heterocyclic group having a ring member nitrogen atom and bonded to a benzene ring bonded thereto via the nitrogen atom, the cyano group, the nitro group, the formyl group, the hydroxycarbonyl group, the alkylcarbonyl group, the alkoxycarbonyl group, the halogen atom, the aralkyl group, the aralkoxy group, the aryloxy group and the aryl group represented by $R^{13}$ and $R^{14}$ are the same as those explained for $R^1$ and $R^2$.

The above alkylthio group represented by $R^{13}$ and preferably an alkylthio group having 1 to 6 carbon atoms. Preferred examples of the alkylthio group include methylthio group, ethylthio group, n-propylthio group, isopropylthio group, n-butylthio group, sec-butylthio group and tert-butylthio group.

The above cycloalkylthio group is preferably a cycloalkylthio group having 3 to 8 carbon atoms. Preferred examples of the cycloalkylthio group include cyclopropylthio group, cyclobutylthio group, cyclopentylthio group and cyclohexylthio group.

The above arylthio group is preferably an arylthio group having 6 to 10 carbon atoms. Preferred examples of the arylthio group include phenylthio group, 1-naphthylthio group and 2-naphthylthio group.

1 to 9 hydrogen atoms, particularly preferably 1 to 4 hydrogen atoms of each of the above arylthio group and the above heteroarylthio group may be substituted by an alkyl group having 1 to 6 carbon atoms, alkoxy group having 1 to 6 carbon atoms, cycloalkyl group having 3 to 8 carbon atoms, or halogen atom.

$R^{13}$ is particularly preferably a hydrogen atom, hydroxyl group, alkyl group, haloalkyl group, cycloalkyl group, alkoxy group, amino group, heterocyclic group having a ring member nitrogen atom and bonded to a benzene ring bonded thereto via the nitrogen atom, cyano group, nitro group, formyl group, hydroxycarbonyl group, alkylcarbonyl group, alkoxycarbonyl group, halogen atom, aralkyl group, aralkoxy group, aryloxy group or aryl group. $R^{14}$ is preferably a hydrogen atom. Specific examples of these compounds include compounds described in a pamphlet of International Laid-Open WO2001/60811.

In the above formula (15b), $R^3$, $R^4$, $R^5$ and $R^6$ are as defined in the above formula (2), and "o" and "p" are each independently an integer of 0 to 4. Specific examples of the chromene compound of the above formula (15b) include compounds described in a pamphlet of International Laid-Open WO2009/136668.

Out of the chromene compounds represented by the above formulas (15a) and (15b), a chromene compound to be combined with in order to provide high transparency preferably has a transmittance by thermochromism of 75% or more and the absorption end of its ultraviolet absorption curve at 380 to 430 nm. Further, a chromene compound having a transmittance by thermochromism of 85% or more and the absorption end of its ultraviolet absorption curve at 380 to 420 nm is particularly preferred, and a chromene compound having a transmittance by thermochromism of 88% or more and the absorption end of its ultraviolet absorption curve at 380 to 410 nm is most preferred. The transmittance by thermochromism and the absorption end of the ultraviolet absorption curve are values measured by methods described in the following examples.

To obtain a photochromic composition comprising the chromene compound of the present invention and another chromene compound, the ratio of these chromene compounds may be suitably determined according to a desired color. To obtain a photochromic curable composition comprising this photochromic composition and polymerizable monomers, the amount of the chromene compound of the present invention or another chromene compound is preferably 0.001 to 10 parts by mass based on 100 parts by mass of the total of all the polymerizable monomers. Stated more specifically, in the case of a thin film such as a coating film (for example, a thin film having a thickness of about 100 μm), color control should be carried out by using 0.001 to 5.0 parts by mass of the chromene compound of the present invention and 0.001 to 5.0 parts by mass of another chromene compound based on 100 parts by mass of the coating film or the total of all the polymerizable monomers which provide the coating film. In the case of a thick cured material (for example, a cured material having a thickness of 1 mm or more), color control should be carried out by using 0.001 to 0.5 part by mass of the chromene compound of the present invention and 0.001 to 0.5 part by mass of another chromene compound based on 100 parts by mass of the thick cured material or the total of all the polymerizable monomers which provide the thick cured material.

(Stabilizer to be Combined with)

Although the chromene compound of the present invention has high durability as it is, its durability can be further enhanced by using the following ultraviolet absorbent, optical stabilizer or antioxidant. As the ultraviolet absorbent may be used known ultraviolet absorbents such as benzophenone-based compounds, benzotriazole-based compounds, cyanoacrylate-based compounds, triazine-based compounds and benzoate-based compounds. Cyanoacrylate-based compounds and benzophenone-based compounds are particularly preferred. When the above ultraviolet absorbent is added to a photochromic curable composition, it is used in an amount of 0.001 to 5 parts by mass based on 100 parts by mass of the total of all the polymerizable monomers so as to exhibit an effect. Known hindered amines may be used as the optical stabilizer, and known hindered phenols may be used as the antioxidant. When the above optical stabilizer and antioxidant are each added to the photochromic curable composition, they are each used in an amount of 0.01 to 10 parts by mass based on 100 parts by mass of the total of all the polymerizable monomers so as to exhibit an effect.

(Use of Chromene Compound)

The chromene compound of the present invention exhibits the same photochromic properties even in a polymer solid matrix. The polymer solid matrix is not particularly limited if the chromene compound of the present invention can be uniformly dispersed therein, and examples of the optically preferred polymer matrix include thermoplastic resins such as methyl polyacrylate, ethyl polyacrylate, methyl polymethacrylate, ethyl polymethacrylate, polystyrene, polyacrylonitrile, polyvinyl alcohol, polyacrylamide, poly(2-hydroxyethylmethacrylate), polydimethylsiloxane and polycarbonate.

A thermosetting resin obtained by polymerizing a radically polymerizable polyfunctional monomer may also be used as the above polymer matrix. Examples of the radically polymerizable polyfunctional monomer include polyacrylate and polymethacrylate compounds such as ethylene glycol diacrylate, diethylene glycol dimethacrylate, triethylene glycol dimethacrylate, tetraethylene glycol dimethacrylate, ethylene glycol bisglycidyl methacrylate, bisphenol A dimethacrylate, 2,2-bis(4-methacryloyloxyethoxyphenyl) propane and 2,2-bis(3,5-dibromo-4-methacryloyloxyethoxyphenyl) propane; polyallyl compounds such as diallyl phthalate, diallyl terephthalate, diallyl isophthalate, diallyl tartarate, diallyl epoxysuccinate, diallyl fumarate, diallyl chlorendate, diallyl hexaphthalate, diallyl carbonate, allyl diglycol carbonate and trimethylolpropane triallyl carbonate; polythioacrylate and polythiomethacrylate compounds such as 1,2-bis(methacryloylthio)ethane, bis(2-acryloylthioethyl) ether and 1,4-bis(methacryloylthiomethyl)benzene; acrylate and methacrylate compounds such as glycidyl acrylate, glycidyl methacrylate, β-methylglycidyl methacrylate, bisphehol A-monoglycidyl ether-methacrylate, 4-glycidyloxy methacrylate, 3-(glycidyl-2-oxyethoxy)-2-hydroxypropyl methacrylate, 3-(glycidyloxy-1-isopropyloxy)-2-hydroxypropyl acrylate and 3-glycidyloxy-2-hydroxypropyloxy)-2-hydroxypropyl acrylate; and divinyl benzene.

Copolymers obtained by copolymerizing the above radically polymerizable polyfunctional monomers with radically polymerizable monofunctional monomers may also be used as the above polymer matrix. The radically polymerizable monofunctional monomers include unsaturated carboxylic acids such as acrylic acid, methacrylic acid and maleic anhydride; acrylate and methacrylate compounds such as methyl acrylate, methyl methacrylate, benzyl methacrylate, phenyl methacrylate and 2-hydroxyethyl methacrylate; fumarate compounds such as diethyl fumarate and diphenyl fumarate; thioacrylate and thiomethacrylate compounds such as methyl thioacrylate, benzyl thioacrylate and benzyl thiomethacrylate; and vinyl compounds such as styrene, chlorostyrene, methyl styrene, vinyl naphthalene, α-methylstyrene dimer and bromostyrene.

As the method of dispersing the chromene compound of the present invention into the above polymer solid matrix, commonly used methods may be employed. The methods include one in which the above thermoplastic resin and the chromene compound are kneaded together while they are molten to disperse the chromene compound into the resin, one in which the chromene compound is dissolved in the above polymerizable monomers and then a polymerization catalyst is added to polymerize the polymerizable monomers by heat or light so as to disperse the chromene compound into the resin, and one in which the surfaces of the above thermoplastic resin and the above thermosetting resin are dyed with the chromene compound to disperse the chromene compound into the resins.

The chromene compound of the present invention can be widely used as a photochromic material for use in, for example, recording materials as substitutes for silver halide photosensitive materials, copy materials, printing photosensitive materials, recording materials for cathode ray tubes, photosensitive materials for lasers and photosensitive materials for holography. A photochromic material comprising the chromene compound of the present invention may also be used as a photochromic lens material, optical filter material, display material or material for actinometers and ornaments.

For instance, when the chromene compound of the present invention is used in a photochromic lens, its production process is not particularly limited as long as uniform light control performance is obtained. An example of the process is such that a polymer film containing the photochromic material of the present invention uniformly dispersed therein is sandwiched between lenses. Another example is such that the chromene compound of the present invention is dispersed into the above polymerizable monomers and the polymerizable monomers are polymerized by a predetermined technique. A further example is such that the chromene compound of the present invention is dissolved in, for example, silicone oil, the resulting solution is impregnated into the surface of a lens at 150 to 200° C. over 10 to 60 minutes, and the surface is further coated with a curable substance to obtain a photochromic lens. A still further example is such that the above polymer film is formed on the surface of a lens and the surface is coated with a curable substance to obtain a photochromic lens.

Moreover, a photochromic lens can also be manufactured by applying a coating agent composed of a photochromic curable composition comprising the chromene compound of the present invention to the surface of a lens substrate and curing the coating film. At this point, the lens substrate may be subjected to a surface treatment with an alkaline solution or a plasma treatment in advance, and a primer may be further applied so as to improve adhesion between the substrate and the coating film by carrying out or not carrying out the above surface treatment.

EXAMPLES

The following examples are provided for the purpose of further illustrating the present invention but are in no way to be taken as limiting.

Example 1

Synthesis of Chromene Compound 1.0 g (2.4 mmol) of the following naphthol compound (16) and 0.80 g (3.0 mmol) of the following propargyl alcohol compound (17) were dissolved in 70 ml of toluene, 0.022 g of p-toluenesulfonic acid was further added to the resulting solution, and the obtained mixture was stirred under reflux by heating for 1 hour.

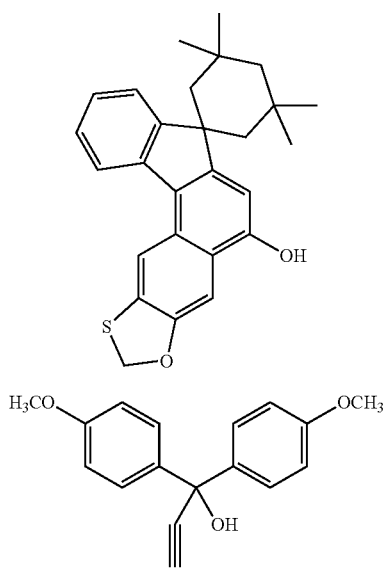

(16)

(17)

After a reaction, the solvent was removed, and the obtained product was purified on silica gel by chromatography to obtain 1.2 g of a white powdery product. The yield was 75%.

The elemental analysis values of this product were 79.16% of C, 6.17% of H and 4.90% of S which were almost equal to the calculated values of $C_{44}H_{42}O_4S$ (C: 79.25%, H: 6.35%, S: 4.81%).

When the proton nuclear magnetic resonance spectrum of the product was measured, it showed 18H peaks based on the methyl proton and methylene proton of a tetramethylcyclohexane ring at δ of around 1.0 to 3.0 ppm, 8H peaks based on the methylene proton of a hetero ring and the methyl proton of a methoxy group at δ of around 2.3 to 6.0 ppm and 16H peaks based on an aromatic proton and an alkene proton at δ of around 5.6 to 9.0 ppm. Further, when the C-nuclear magnetic resonance spectrum was measured, it showed a peak based on the carbon of an aromatic ring at δ of around 110 to 160 ppm, a peak based on the carbon of an alkene at δ of around 80 to 140 ppm and a peak based on the carbon of an alkyl at δ of around 20 to 60 ppm.

It was confirmed from the above results that the isolated product was a compound represented by the following formula (18).

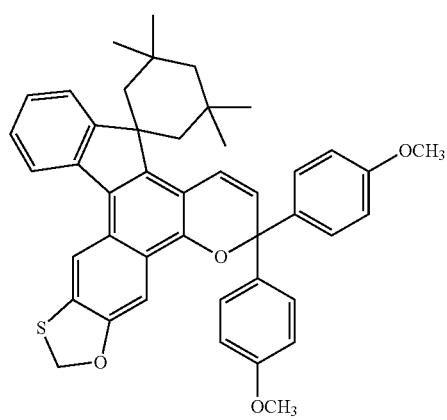

(18)

Examples 2 to 7

Synthesis of Chromene Compound

Chromene compounds shown in Tables 1 (Examples 2 to 4) and 2 (Examples 5 to 7) were synthesized in the same manner as in Example 1. When the structures of the obtained products were analyzed by using the same structure confirming means as in Example 1, it was confirmed that they were compounds represented by structural formulas shown in Tables 1 and 2. Table 3 shows the elemental analysis values, calculated values obtained from the structural formulas and characteristic $^1$H-NMR spectra of these compounds.

TABLE 1

| Example No. | Raw materials | |
|---|---|---|
| | Naphthol compound | Propargyl alcohol compound |
| 2 | | |

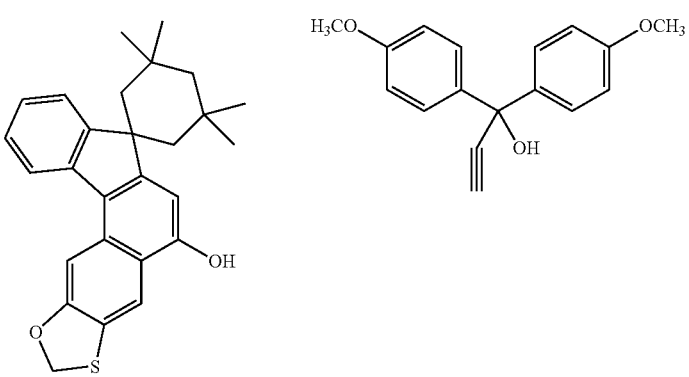

TABLE 1-continued

| Example No. | | |
|---|---|---|
| 3 | [structure: fluorene-spiro-tetramethylcyclohexane fused to naphthol with dithiole] | [structure: 1,1-bis(4-methoxyphenyl)prop-2-yn-1-ol] |
| 4 | [structure: fluorene-spiro-cyclooctane fused to naphthol with oxathiole] | [structure: 1,1-bis(4-methoxyphenyl)prop-2-yn-1-ol] |

| Example No. | Product | Yield (%) |
|---|---|---|
| 2 | [structure: naphthopyran product with spiro-tetramethylcyclohexane fluorene and bis(4-methoxyphenyl) substituents, with oxathiole ring] | 80 |
| 3 | [structure: naphthopyran product with spiro-tetramethylcyclohexane fluorene and bis(4-methoxyphenyl) substituents, with dithiole ring] | 78 |

TABLE 1-continued
| 4 | 80 |
|---|---|
| 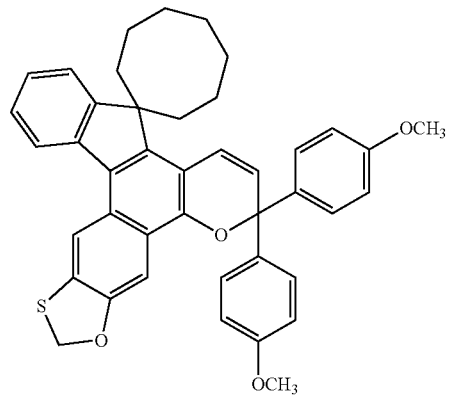 [SMILES: COc1ccc(C2(c3ccc(OC)cc3)C=Cc3c4c(c5cc6c(cc5c3O2)OCS6)-c2ccccc2C42CCCCCCC2)cc1] | |
TABLE 2
| Example No. | Raw materials | |
|---|---|---|
| | Naphthol compound | Propargyl alcohol compound |
| 5 | 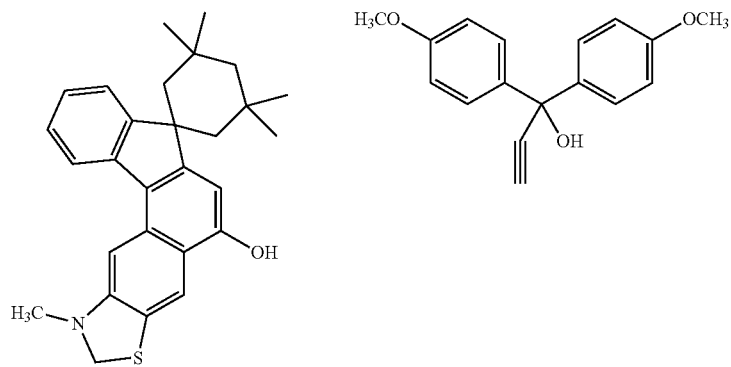 | |
| 6 | 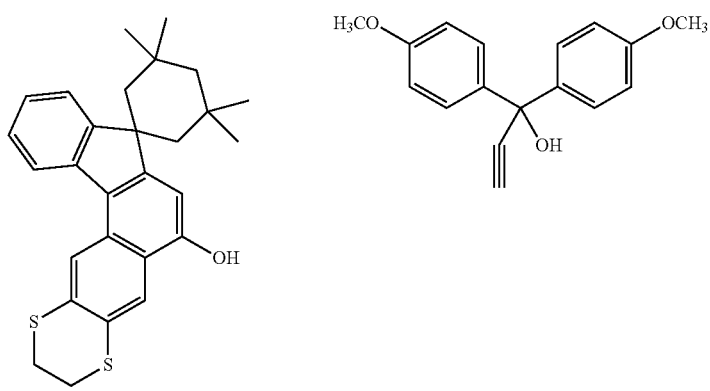 | |

TABLE 2-continued
| 7 | 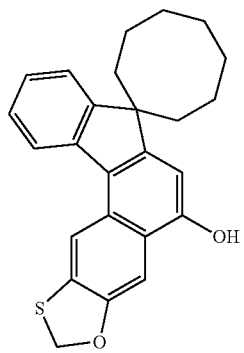 [SMILES: Oc1cc2c(c3cc4c(cc13)OCS4)-c1ccccc1C21CCCCCCC1] | 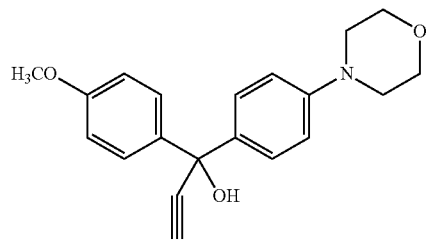 [SMILES: C#CC(O)(c1ccc(OC)cc1)c1ccc(N2CCOCC2)cc1] |
| Example No. | Product | Yield (%) |
|---|---|---|
| 5 | 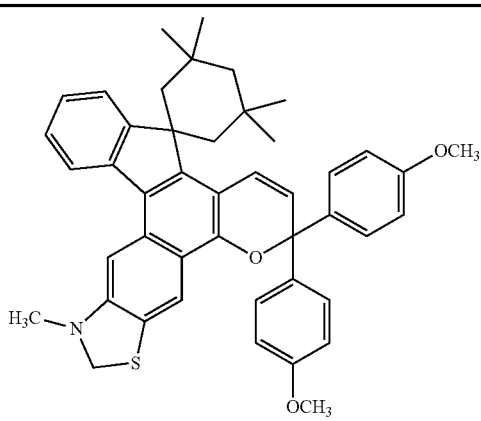 | 79 |
| 6 | 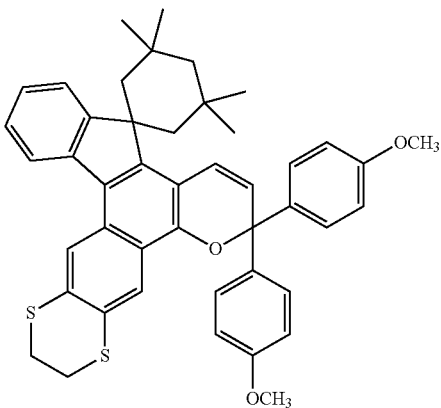 [SMILES: COc1ccc(C2(c3ccc(OC)cc3)C=Cc3c4c(c5cc6c(cc5c3O2)SCCS6)-c2ccccc2C42CC(C)(C)CC(C)(C)C2)cc1] | 78 |
| 7 | 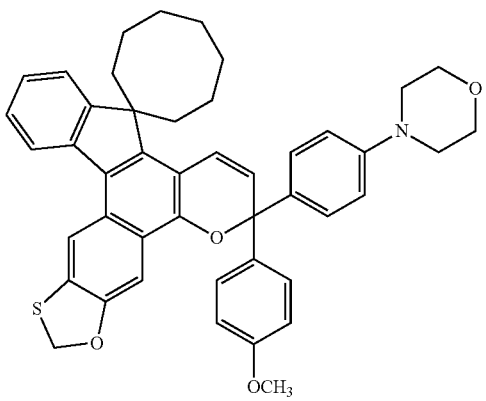 [SMILES: COc1ccc(C2(c3ccc(N4CCOCC4)cc3)C=Cc3c4c(c5cc6c(cc5c3O2)OCS6)-c2ccccc2C42CCCCCCC2)cc1] | 83 |

TABLE 3

| Example No. | Experimental values | | | | Calculated values | | | | $^1$H-NMR (ppm) |
|---|---|---|---|---|---|---|---|---|---|
| | C | H | N | S | C | H | N | S | |
| 2 | 79.40 | 6.26 | | 4.77 | 79.25 | 6.35 | | 4.81 | δ5.0–9.0 18H<br>δ0.5–4.9 24H |
| 3 | 77.19 | 6.48 | | 9.18 | 77.38 | 6.20 | | 9.39 | δ5.0–9.0 16H<br>δ0.5–4.9 26H |
| 4 | 78.80 | 5.80 | | 4.94 | 78.97 | 6.00 | | 5.02 | δ5.0–9.0 18H<br>δ0.5–4.9 20H |
| 5 | 79.60 | 6.71 | 2.17 | 4.85 | 79.49 | 6.67 | 2.06 | 4.72 | δ5.0–9.0 16H<br>δ0.5–4.9 29H |
| 6 | 77.38 | 6.50 | | 9.37 | 77.55 | 6.36 | | 9.20 | δ5.0–9.0 16H<br>δ0.5–4.9 28H |
| 7 | 7.86 | 6.30 | 2.13 | 4.62 | 77.89 | 6.25 | 2.02 | 4.62 | δ5.0–9.0 18H<br>δ0.5–4.9 25H |

Examples 8 to 14

Evaluation of Physical Properties of Photochromic Plastic Lenses Manufactured by Coating Method The chromene compound No. 1 obtained in the above Example 1 was mixed with a photopolymerization initiator and polymerizable monomers, the resulting mixture was applied to the surface of a lens substrate, and ultraviolet light was applied to polymerize the coating film on the surface of the lens substrate.

As for the photochromic curable composition, a mixture of 50 parts by mass of 2,2-bis(4-methacryloyloxypentaethoxyphenyl) propane, 10 parts by mass of polyethylene glycol diacrylate (average molecular weight of 532), 10 parts by mass of trimethylolpropane trimethacrylate, 10 parts by mass of polyester oligomer hexaacrylate (EB-1830 of Daicel UCB Co., Ltd.) and 10 parts by mass of glycidyl methacrylate as radically polymerizable monomers was used. After 1 part by mass of the chromene compound No. 1 obtained in Example 1 was added to and fully mixed with 90 parts by mass of the mixture of these radically polymerizable monomers, 0.3 part by mass of CGI1800 {a mixture of 1-hydroxycyclohexylphenyl ketone and bis(2,6-dimethoxybenzoyl)-2,4,4-trimethylpentylphosphine oxide (weight ratio of 3:1)} as a photopolymerization initiator, 5 parts by mass of bis(1,2,2,6,6-pentamethyl-4-piperidyl)sebacate and 3 parts by mass of ethylenebis(oxyethylene)bis[3-(5-tert-butyl-4-hydroxy-m-tolyl)propionate] as a stabilizer, 7 parts by mass of γ-methacryloyloxypropyl trimethoxysilane as a silane coupling agent and 3 parts by mass of N-methyldiethanolamine were added to and fully mixed with the above mixture to obtain a photochromic curable composition.

Subsequently, about 2 g of the photochromic curable composition obtained by the above method was applied to the surface of a lens substrate (CR39: allyl resin plastic lens; refractive index of 1.50) by using the 1H-DX2 spin coater of MIKASA Co., Ltd. This coated lens was irradiated with light from a metal halide lamp having an output of 120 mW/cm$^2$ in a nitrogen gas atmosphere for 3 minutes to cure the photochromic curable composition so as to manufacture an optical article (photochromic plastic lens) which was covered with a polymer film containing the chromene compound dispersed therein (thickness of polymer film: 40 μm).

The following photochromic properties of the obtained photochromic plastic lens were evaluated. The evaluation results obtained by using the chromene compound of Example 1 are shown in Table 4.

[1] Maximum absorption wavelength ($\lambda_{max}$): This is the maximum absorption wavelength after color development obtained by means of the spectrophotometer (MCPD3000 instantaneous multi-channel photodetector) of Otsuka Electronics Co., Ltd. and used as an index of color at the time of color development.

[2] Color optical density ($A_0$): This is the difference between absorbance {ε(120)} after 120 seconds of exposure at the above maximum absorption wavelength and absorbance ε(0) under no exposure and used as an index of color optical density. It can be said that as this value becomes larger, photochromic properties become better.

[3] Double peak characteristic ($A_Y/A_B$): This is the ratio of color optical density ($A_Y$: value of $\lambda_{max}$) at a yellow range (having a maximum absorption wavelength at 430 to 530 nm) and color optical density ($A_B$: value of $\lambda_{max}$) at a blue range (having a maximum absorption wavelength at 550 to 650 nm) and used as an index of double peak characteristic.

[4] Fading half period [τ1/2 (sec.)]: This is a time required for the reduction of the absorbance at the above maximum absorption wavelength of a sample to ½ of {ε(120)−ε(0)} when exposure is stopped after 120 seconds of exposure and used as an index of fading speed. As this time becomes shorter, the fading speed becomes higher.

[5] Absorption end {$\lambda_0$}: After the photochromic plastic lens obtained under the above conditions is used as a sample and kept in the dark for one day, the ultraviolet light transmittance (T %) at 300 to 800 nm of the sample is measured with an ultraviolet visible spectrophotometer (UV-2550 of Shimadzu Corporation) at room temperature. A tangent line is drawn on the obtained ultraviolet light absorption curve to ensure that the transmittance (T %) of the ultraviolet light absorption curve passes a point of 50% so as to obtain an absorption wavelength at which the transmittance (T %) of the tangent line becomes 0 as the absorption end (absorption end of the ultraviolet light spectrum) and used as an index of initial coloration. For example, in an optical article such as a spectacle lens, as this value becomes smaller, initial coloration becomes weaker and transparency under no exposure becomes higher.

[6] Thermochromism {$T_0$}: The photochromic plastic lens obtained under the above conditions is used as a sample and the transmittance (T %) at 300 to 800 nm of the sample is measured with an ultraviolet visible spectrophotometer (UV-2550 of Shimadzu Corporation) at room temperature. This is a transmittance at a wavelength at which the transmittance at 430 to 650 nm becomes minimal and used as an index of initial coloration. As this value becomes larger, initial coloration becomes weaker and transparency under no exposure becomes higher.

[7] Residual rate ($A_{50}/A_0 \times 100$): A deterioration promotion test is made on the obtained photochromic plastic lens by using the X25 xenon weather meter of Suga Test Instruments Co., Ltd. for 50 hours. Thereafter, the above color optical density is evaluated before and after the test by measuring the color optical density ($A_0$) before the test and the color optical density ($A_{50}$) after the test in order to obtain the ratio ($A_{50}/A_0$) of these values as residual rate which is used as an index of color development durability. As the residual rate becomes higher, color development durability becomes higher.

(Evaluation of Heat Resistance)

The heat resistance of the photochromic plastic lens is evaluated by conducting a heating test in the dark at 110° C. using a fan oven for 12 hours to measure a color drift.

[8] color drift: The change rate of the above-described double peak characteristic ($A_Y/A_B$) is defined as $\{1-(A_Y/A_B$ after heating test)/($A_Y/A_B$ before heating test)$\}$ and used as an index of a drift of a developed color. It can be said that the change rate of double peak characteristic is lower, heat resistance becomes higher with a smaller color drift by heating.

The evaluation results of the heat resistance of each of photochromic plastic lenses manufactured by using the chromene compounds of the present invention are shown in Table 4.

Photochromic plastic lenses were obtained and their characteristic properties were evaluated in the same manner as above except that the compounds obtained in Examples 2 to 7 (No. 2 to 7) were used as the chromene compound. The results are shown in Table 4. In Table 4, compounds Nos. 1 to 7 are the chromene compounds obtained in Example Nos. 1 to 7, respectively. For example, the chromene compound obtained in Example 1 is represented as compound No. 1.

TABLE 4

| Example No. | Compound No. | λmax (nm) | Color optical density $A_0$ | Double peak characteristic $A_Y/A_B$ | Fading half period $\tau^{1/2}$ (sec) | Initial coloration (absorption end) (nm) |
|---|---|---|---|---|---|---|
| 8 | 1 | 460 | 0.53 | 1.51 | 39 | 413 |
|   |   | 573 | 0.35 |      | 39 |     |
| 9 | 2 | 472 | 0.57 | 1.48 | 47 | 400 |
|   |   | 579 | 0.39 |      | 47 |     |
| 10 | 3 | 466 | 0.60 | 1.44 | 48 | 404 |
|    |   | 576 | 0.42 |      | 48 |     |
| 11 | 4 | 460 | 0.80 | 1.51 | 87 | 413 |
|    |   | 573 | 0.53 |      | 87 |     |
| 12 | 5 | 481 | 0.86 | 1.80 | 76 | 414 |
|    |   | 582 | 0.48 |      | 76 |     |
| 13 | 6 | 460 | 0.51 | 1.50 | 45 | 413 |
|    |   | 573 | 0.34 |      | 45 |     |
| 14 | 7 | 480 | 0.64 | 1.13 | 58 | 412 |
|    |   | 588 | 0.57 |      | 58 |     |

| Example No. | Initial coloration (thermochromism) (%) | Residual rate ($A_{50}/A_0$) × 100(%) | Double peak characteristic after heating $A_{Y'}/A_{B'}$ | Color drift $1 - (A_Y/A_B)/(A_{Y'}/A_{B'})$ |
|---|---|---|---|---|
| 8 | 89 | 87 | 1.18 | 0.22 |
|   | 90 | 87 |      |      |
| 9 | 86 | 86 | 1.14 | 0.23 |
|   | 86 | 86 |      |      |
| 10 | 89 | 84 | 1.12 | 0.22 |
|    | 90 | 84 |      |      |
| 11 | 86 | 86 | 1.19 | 0.21 |
|    | 87 | 86 |      |      |
| 12 | 85 | 83 | 1.52 | 0.16 |
|    | 87 | 83 |      |      |
| 13 | 88 | 86 | 1.18 | 0.21 |
|    | 89 | 86 |      |      |
| 14 | 85 | 83 | 0.91 | 0.19 |
|    | 85 | 83 |      |      |

Comparative Examples 1 to 4

Evaluation of Physical Properties of Photochromic Plastic Lenses Manufactured by Coating Method For comparison, photochromic plastic lenses were obtained and their characteristic properties were evaluated in the same manner as in Example 8 except that compounds represented by the following formulas (A), (B), (C) and (D) were used. The results are shown in Table 5.

TABLE 5

| Comparative Example No. | Compound No. | λmax (nm) | Color optical density $A_0$ | Double peak characteristic $A_Y/A_B$ | Fading half period $\tau1/2$ (sec) | Initial coloration (absorption end) (nm) | Initial coloration (thermo-chromism) (%) | Residual rate $(A_{50}/A_0) \times 100$ (%) |
|---|---|---|---|---|---|---|---|---|
| 1 | (A) | 457 | 0.69 | 1.56 | 195 | 397 | 67 | 76 |
|   |     | 574 | 0.45 |      | 196 |     | 75 | 77 |
| 2 | (B) | 455 | 0.30 | 0.94 | 83  | 410 | 77 | 35 |
|   |     | 576 | 0.32 |      | 83  |     | 78 | 35 |
| 3 | (C) | 458 | 0.44 | 1.20 | 68  | 422 | 84 | 85 |
|   |     | 568 | 0.37 |      | 68  |     | 86 | 84 |
| 4 | (D) | 464 | 0.51 | 1.50 | 50  | 411 | 89 | 82 |
|   |     | 573 | 0.34 |      | 50  |     | 90 | 82 |

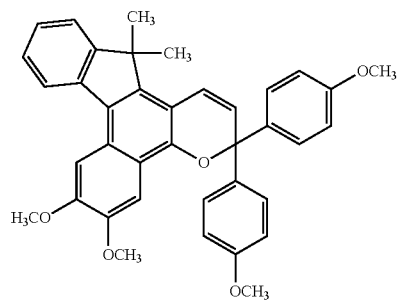

(A)

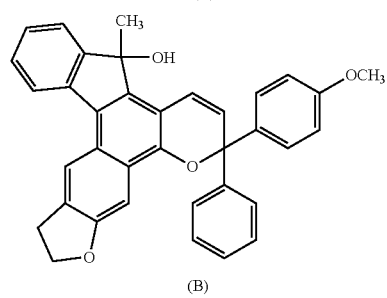

(B)

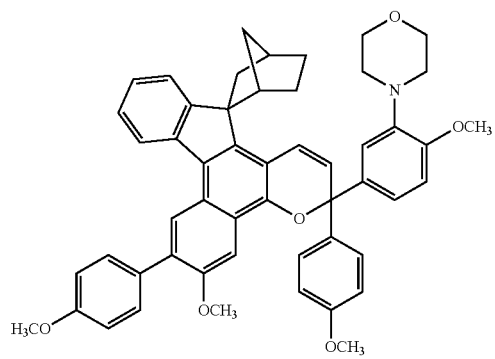

(C)

TABLE 5-continued

| Comparative Example No. | Compound No. | λmax (nm) | Color optical density $A_0$ | Double peak characteristic $A_Y/A_B$ | Fading half period τ1/2 (sec) | Initial coloration (absorption end) (nm) | Initial coloration (thermochromism) (%) | Residual rate $(A_{50}/A_0)\times 100$ (%) |
|---|---|---|---|---|---|---|---|---|

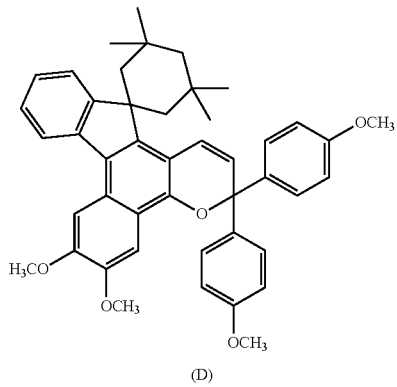

(D)

It is understood that the photochromic plastic lenses of Examples 8 to 14 in which the chromene compounds of the present invention were used have excellent properties such as color optical density, fading speed and durability while retaining high double peak characteristic as compared with the photochromic plastic lenses of Comparative Example 1 (chromene compound represented by the above formula (A)), Comparative Example 2 (chromene compound represented by the above formula (B)) and Comparative Example 3 (chromene compound represented by the above formula (C)).

As for initial coloration, the photochromic plastic lenses of Comparative Examples 1 and 2 have strong initial coloration by thermochromism. Since the absorption end of the photochromic plastic lens of Comparative Example 3 goes beyond 420 nm into the visible range, its initial coloration is marked. In contrast to this, in Examples of the present invention, as thermochromism is little and the absorption end is existent at a short wavelength range, initial coloration is little.

Further, it is understood that the above photochromic plastic lenses are superior to the photochromic plastic lens of Comparative Example 4 (chromene compound represented by the above formula (D)) in color optical density and fading speed.

Examples 15 to 21

Synthesis of Chromene Compounds

Chromene compounds shown in Tables 6 and 7 were synthesized in the same manner as in Example 1. When the structures of the obtained chromene compounds were analyzed in the same manner as in Example 1, it was confirmed that they were compounds represented by the structural formulas shown in Tables 6 and 7. Table 8 shows the elemental analysis values and $^1$H-NMR spectral values of the chromene compounds obtained in these Examples.

TABLE 6

| Ex. No. | Raw materials | |
|---|---|---|
| | Naphthol compound | Propargyl alcohol compound |
| 15 | | |

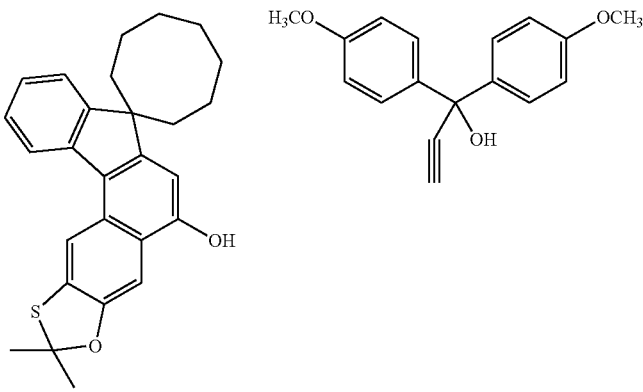

TABLE 6-continued
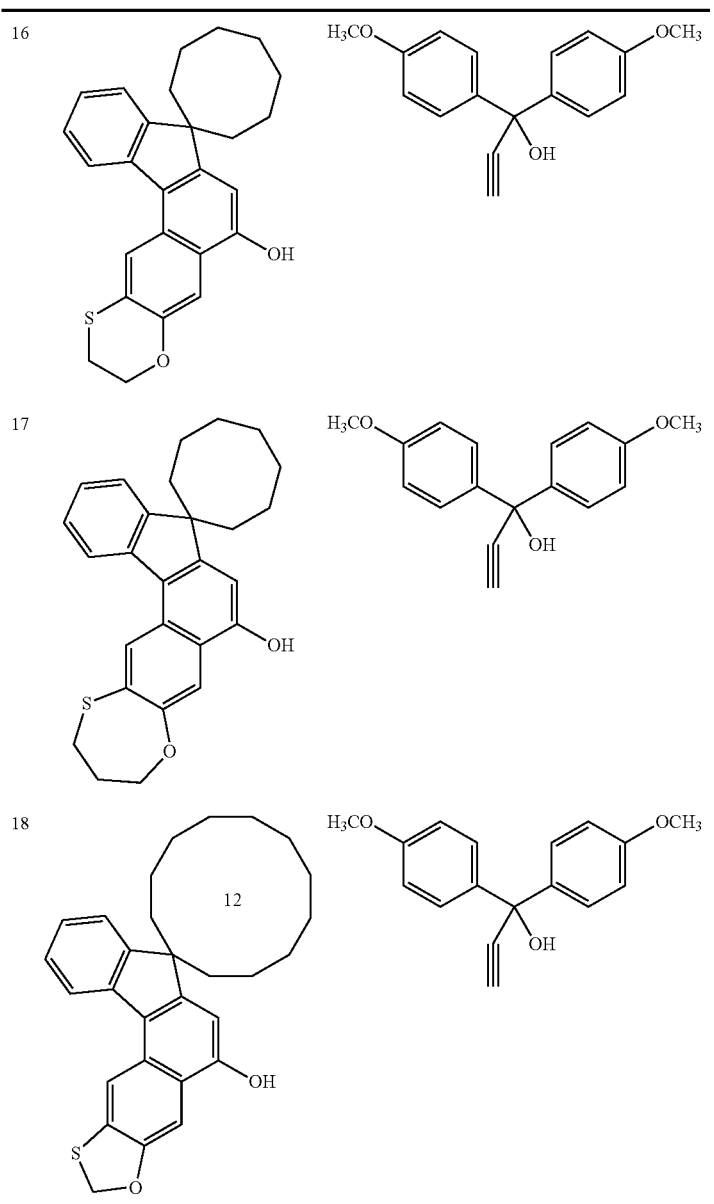
| Ex. No. | Product | Yield (%) |
|---|---|---|
| 15 | | 79 |
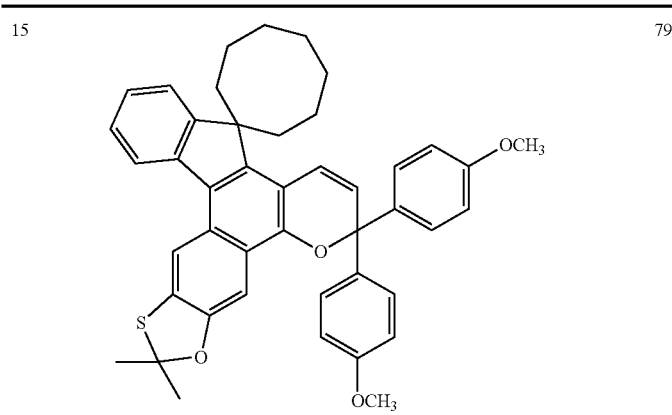

TABLE 6-continued
| 16 | 82 |
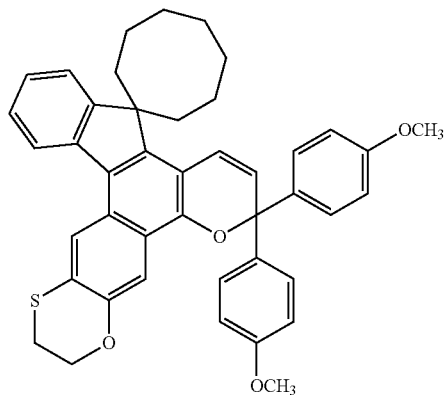 [SMILES: COc1ccc(C2(c3ccc(OC)cc3)C=Cc3c4c(c5cc6c(cc5c3O2)OCCS6)-c2ccccc2C42CCCCCCC2)cc1]
| 17 | 74 |
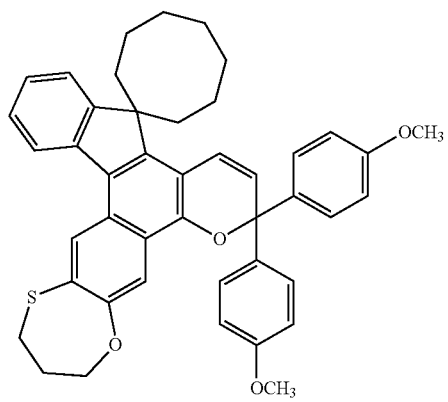 [SMILES: COc1ccc(C2(c3ccc(OC)cc3)C=Cc3c4c(c5cc6c(cc5c3O2)OCCCS6)-c2ccccc2C42CCCCCCC2)cc1]
| 18 | 76 |
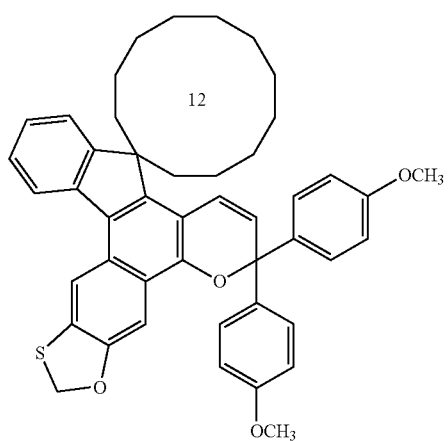 [SMILES: COc1ccc(C2(c3ccc(OC)cc3)C=Cc3c4c(c5cc6c(cc5c3O2)OCS6)-c2ccccc2C42CCCCCCCCCCC2)cc1]
Ex.: Example

TABLE 7

| Ex. No. | Raw materials | | Product | Yield (%) |
|---|---|---|---|---|
| | Naphthol compound | Propargyl alcohol compound | | |
| 19 | | | | 81 |
| 20 | | | | 80 |
| 21 | | | | 83 |

Ex: Example

TABLE 8

| Example No. | Experimental values | | | | Calculated values | | | | $^1$H-NMR (ppm) |
|---|---|---|---|---|---|---|---|---|---|
| | C | H | N | S | C | H | N | S | |
| 15 | 79.41 | 6.24 | | 4.91 | 79.25 | 6.35 | | 4.81 | δ5.0-9.0 16H<br>δ0.5-4.9 26H |
| 16 | 79.24 | 6.24 | | 4.98 | 79.11 | 6.18 | | 4.91 | δ5.0-9.0 16H<br>δ0.5-4.9 24H |
| 17 | 79.12 | 6.34 | | 4.76 | 79.25 | 6.35 | | 4.81 | δ5.0-9.0 16H<br>δ0.5-4.9 26H |
| 18 | 79.58 | 6.73 | | 4.58 | 79.50 | 6.67 | | 4.61 | δ5.0-9.0 18H<br>δ0.5-4.9 28H |
| 19 | 79.03 | 5.97 | | 5.11 | 78.97 | 6.00 | | 5.02 | δ5.0-9.0 18H<br>δ0.5-4.9 20H |

TABLE 8-continued

| Example No. | Experimental values | | | | Calculated values | | | | $^1$H-NMR (ppm) |
|---|---|---|---|---|---|---|---|---|---|
| | C | H | N | S | C | H | N | S | |
| 20 | 78.02 | 6.63 | 1.89 | 4.37 | 78.19 | 6.56 | 1.94 | 4.44 | δ5.0-9.0 18H<br>δ0.5-4.9 29H |
| 21 | 78.26 | 6.50 | 2.03 | 4.69 | 78.04 | 6.41 | 1.98 | 4.53 | δ5.0-9.0 18H<br>δ0.5-4.9 27H |

Examples 22 to 28

Evaluation of Physical Properties of Photochromic Plastic Lenses Manufactured by Coating Method Photochromic plastic lenses were obtained and their characteristic properties were evaluated in the same manner as in Example 8 except that compounds obtained in Examples 15 to 21 were used as the chromene compound. The results are shown in Table 9. In Table 9, compounds Nos. 15 to 21 are chromene compounds obtained in Examples 15 to 21, respectively. For example, the chromene compound obtained in Example 15 is represented as compound No. 15.

Example 29

Production of Naphthol Compound 38.3 g (277.4 mmol) of the benzene compound represented by the above formula (8) was added dropwise to a dichloromethane solution (400 ml) containing 38.8 g (291.2 mmol) of aluminum chloride and 40.9 g (291.2 mmol) of benzoyl chloride cooled to 0° C. After addition, the resulting mixture was stirred for 2 hours. After a reaction, the reaction product was washed with water, the solvent was removed, and the obtained product was purified by column chromatography to obtain a benzophenone derivative represented by the following formula (19) as 41.0 g (169.2 mmol, yield of 61%) of a white solid.

TABLE 9

| Example No. | Compound No. | λmax (nm) | Color optical density $A_0$ | Double peak characteristic $A_Y/A_B$ | Fading half period $\tau^{1/2}$ (sec) | Initial coloration (absorption end) (nm) |
|---|---|---|---|---|---|---|
| 22 | 15 | 459 | 0.81 | 1.50 | 90 | 413 |
| | | 572 | 0.54 | | 91 | |
| 23 | 16 | 459 | 0.80 | 1.51 | 92 | 413 |
| | | 573 | 0.53 | | 93 | |
| 24 | 17 | 459 | 0.78 | 1.47 | 94 | 413 |
| | | 573 | 0.53 | | 94 | |
| 25 | 18 | 460 | 0.94 | 1.54 | 128 | 414 |
| | | 573 | 0.61 | | 126 | |
| 26 | 19 | 457 | 0.89 | 1.48 | 80 | 414 |
| | | 568 | 0.60 | | 81 | |
| 27 | 20 | 479 | 0.64 | 1.14 | 61 | 412 |
| | | 584 | 0.56 | | 60 | |
| 28 | 21 | 480 | 0.64 | 1.12 | 65 | 414 |
| | | 582 | 0.57 | | 65 | |

| Example No. | Initial coloration (thermochromism) (%) | Residual rate $(A_{50}/A_0) \times 100$ (%) | Double peak characteristic after heating $A_Y'/A_B'$ | Color drift $1 - (A_Y/A_B)/(A_Y'/A_B')$ |
|---|---|---|---|---|
| 22 | 86 | 85 | 1.32 | 0.12 |
| | 87 | 86 | | |
| 23 | 86 | 86 | 1.19 | 0.21 |
| | 87 | 86 | | |
| 24 | 86 | 84 | 1.15 | 0.22 |
| | 87 | 84 | | |
| 25 | 85 | 83 | 1.21 | 0.21 |
| | 85 | 83 | | |
| 26 | 85 | 86 | 1.19 | 0.20 |
| | 85 | 86 | | |
| 27 | 85 | 83 | 1.02 | 0.11 |
| | 85 | 83 | | |
| 28 | 85 | 82 | 0.91 | 0.19 |
| | 85 | 82 | | |

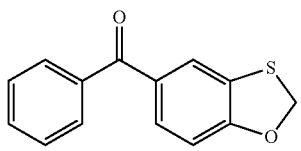

(19)

The benzophenone derivative of the above formula (19) and 33.9 g (194.6 mmol) of diethyl succinate were dissolved in 200 ml of tetrahydrofuran and heated to 55° C. A tetrahydrofuran solution (400 ml) containing 21.9 g (194.6 mmol) of potassium-t-butoxide was added dropwise to this solution and stirred for 1 hour. After a reaction, 200 ml of toluene was added, the resulting reaction solution was washed with concentrated hydrochloric acid and then with water, and the solvent was removed to obtain a compound represented by the following formula (20) as 39.5 g (106.6 mmol, yield of 63%) of brown oil.

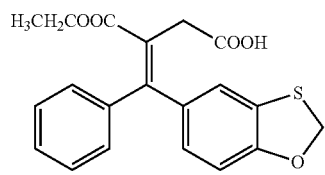

(20)

The above compound of the formula (20), 8.7 g (106.6 mmol) of sodium acetate and 54.4 g (533.0 mmol) of acetic anhydride were dissolved in 150 ml of toluene and refluxed for 3 hours. After a reaction, the reaction solution was washed with water, the solvent was removed, and the obtained product was purified by recrystallization with ethyl acetate and acetonitrile so as to obtain a compound represented by the following formula (21) as 9.2 g (23.4 mmol, yield of 22%) of an orange solid.

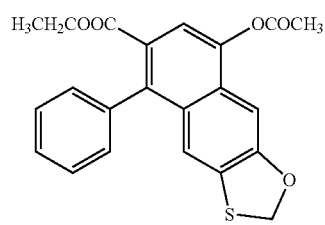

(21)

The above compound of the formula (21) was dispersed into 40 ml of methanol. 56 ml of an aqueous solution containing 5.6 g (140.4 mmol) of sodium hydroxide was added to this solution and refluxed for 3 hours. After a reaction, the reaction solution was washed with concentrated hydrochloric acid and then with water, the solvent was removed, and the obtained product was purified by reslurrying with toluene to obtain a carboxylic acid derivative represented by the following formula (22) as 7.4 g (22.7 mmol, yield of 97%) of a yellow solid.

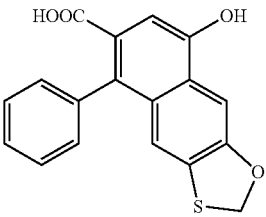

(22)

The above compound of the formula (22) and 6.2 g (49.3 mmol) of benzyl chloride were dissolved in 74 ml of N,N-dimethylformamide. 12.5 g (90.8 mmol) of potassium carbonate was added to this solution, and the resulting mixture was heated to 60° C. and stirred for 4 hours. After a reaction, 100 ml of toluene was added, the resulting reaction solution was washed with water, and the solvent was removed to obtain a compound represented by the following formula (23) as 11.3 g (22.5 mmol, yield of 99%) of a yellow solid.

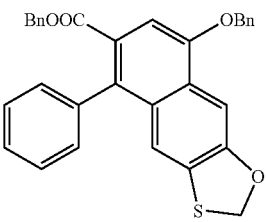

(23)

The above compound of the formula (23) was dispersed into 350 ml of isopropyl alcohol. 405 ml of an aqueous solution containing 40.5 g (1012.5 mmol) of sodium hydroxide was added to this solution and refluxed for 3 hours. After a reaction, 300 ml of toluene and 200 ml of tetrahydrofuran were added, the resulting reaction solution was washed with concentrated hydrochloric acid and then with water, the solvent was removed, and the obtained product was purified by reslurrying with toluene and hexane to obtain a carboxylic acid derivative represented by the following formula (24) as 9.0 g (21.6 mmol, yield of 96%) of a yellow solid.

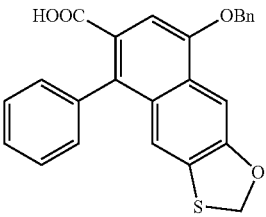

(24)

The above compound of the formula (24) was dispersed into 120 ml of toluene. 13.1 g (129.6 mmol) of triethylamine and 7.7 g (28.1 mmol) of diphenylphosphorylazide were added to this solution and stirred at room temperature for 4 hours. 5.0 g (108.0 mmol) of ethanol was added to this solution to carry out a reaction at 70° C. for 2 hours. 150 ml of ethanol was added to this solution, and then 11.2 g (280.8 mmol) of potassium hydroxide was added and refluxed for 6 hours. After a reaction, ethanol was distilled off at normal pressure, tetrahydrofuran was added, the reaction solution was washed with water, and the solvent was removed to obtain a compound represented by the following formula (25) as 7.7 g (19.9 mmol, yield of 92%) of a yellow solid.

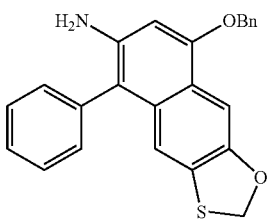

(25)

The above compound of the formula (25) was dispersed into 150 ml of acetonitrile, and 60.0 g (98.5 mmol) of a 6% hydrochloric acid aqueous solution was added and cooled to 0 to 5° C. 6.2 g (29.9 mmol) of a 33% sodium nitrite aqueous solution was added to this solution and stirred for 30 minutes. 16.5 g (99.5 mmol) of a 50% potassium iodide aqueous solution was added to this solution and stirred at room temperature for 3 hours. After a reaction, toluene was added, the reaction solution was washed with water, the solvent was removed, and the obtained product was purified by column chromatography to obtain a compound represented by the following formula (26) as 6.9 g (13.9 mmol, yield of 70%) of a yellow solid.

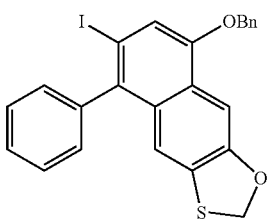

(26)

The above compound of the formula (26) was dispersed into 270 ml of toluene and cooled to −15° C. 17.4 ml (27.8 mmol) of n-butyl lithium (1.6 M hexane solution) was added dropwise to this solution and stirred for 30 minutes. 10.0 g of a toluene solution containing 5.0 g (32.0 mmol) of 3,3,5,5-tetramethylcyclohexanone was added dropwise to this solution and stirred at −15° C. for 2 hours. After a reaction, toluene and tetrahydrofuran were added, the reaction solution was washed with water, the solvent was removed, and the obtained product was purified by reslurrying with toluene to obtain a compound represented by the following formula (27) as 7.5 g (9.7 mmol, yield of 70%) of a yellow solid.

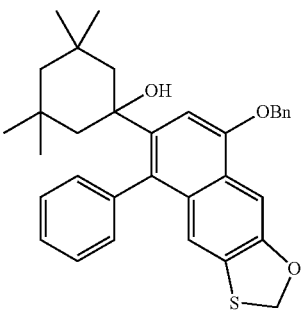

(27)

The above compound of the formula (27) and 122.9 mg (0.5 mmol) of (±)-10-camphorsulfonic acid were dissolved in 225 ml of toluene and refluxed for 30 minutes. After the obtained solution was left to be cooled to room temperature, this solution was added to 100 ml of a toluene solution containing 9.2 g (48.5 mmol) of p-toluenesulfonic acid monohydrate heated at 90° C. and refluxed for 4 hours. After a reaction, the reaction solution was washed with water, the solvent was removed, and the obtained product was purified by column chromatography to obtain a naphthol compound represented by the following formula (16) as 1.7 g (4.5 mmol, yield of 46%) of a yellow solid.

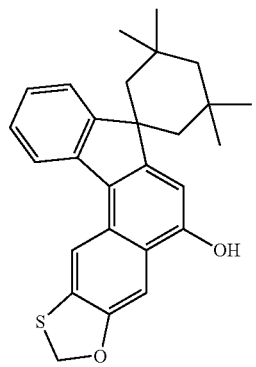

(16)

The elemental analysis values of this product were 77.51% of C, 6.81% of H and 7.64% of S which were almost equal to the calculated values of $C_{27}H_{28}O_2S$ (C: 77.85%, H: 6.77%, S: 7.70%).

When the proton nuclear magnetic resonance spectrum of the product was measured, it showed 18H peaks based on the methyl, proton and methylene proton of a tetramethylcyclohexane ring at δ of around 1.0 to 3.0 ppm, a 2H peak based on the methylene proton of a hetero ring at δ of around 5.0 to 6.0 ppm and 8H peaks based on an aromatic proton and the proton of a hydroxyl group at δ of around 5.0 to 9.0 ppm. Further, when the $^{13}C$-nuclear magnetic resonance spectrum was measured, it showed a peak based on the carbon of an aromatic ring at δ of around 110 to 160 ppm and a peak based on the carbon of an alkyl group at δ of around 20 to 80 ppm.

It was confirmed from these results that the isolated product was a compound represented by the above formula (16). This compound is the naphthol compound used in the above Example 1.

Examples 30 to 42

Synthesis of Naphthol Compounds

Naphthol compounds used in Examples (Examples 2 to 21) were synthesized in the same manner as in Example 29. When the structures of the obtained products were analyzed by using the same structure confirming means as in Example 29, it was confirmed that they were the compounds used in Examples shown in Tables 1, 2, 6 and 7. Table 10 shows the elemental analysis values, calculated values obtained from the structural formulas and characteristic $^1H$-NMR spectra of these compounds.

TABLE 10

| Example No. | *Example Nos. of the chromene compounds | Experimental values | | | | Calculated values | | | | ¹H-NMR (ppm) |
|---|---|---|---|---|---|---|---|---|---|---|
| | | C | H | N | S | C | H | N | S | |
| 30 | 2 | 77.92 | 6.87 | | 7.82 | 77.85 | 6.77 | | 7.70 | δ5.0-9.0 10H<br>δ0.5-4.5 18H |
| 31 | 3 | 74.82 | 6.62 | | 14.93 | 74.96 | 6.52 | | 14.82 | δ5.0-9.0 8H<br>δ0.5-4.5 20H |
| 32 | 4 | 77.14 | 6.33 | | 8.18 | 77.28 | 6.23 | | 8.25 | δ5.0-9.0 10H<br>δ0.5-4.5 14H |
| 33 | 5 | 78.42 | 7.19 | 3.32 | 7.32 | 78.28 | 7.27 | 3.26 | 7.46 | δ5.0-9.0 8H<br>δ0.5-4.5 23H |
| 34 | 6 | 75.18 | 6.82 | | 14.52 | 75.29 | 6.77 | | 14.36 | δ5.0-9.0 8H<br>δ0.5-4.5 22H |
| 35 | 7 | 77.14 | 6.33 | | 8.18 | 77.28 | 6.23 | | 8.25 | δ5.0-9.0 10H<br>δ0.5-4.5 18H |
| 36 | 15 | 77.65 | 6.81 | | 7.62 | 77.85 | 6.77 | | 7.70 | δ5.0-9.0 8H<br>δ0.5-4.5 20H |
| 37 | 16 | 77.69 | 6.48 | | 8.06 | 77.58 | 6.51 | | 7.97 | δ5.0-9.0 8H<br>δ0.5-4.5 18H |
| 38 | 17 | 77.98 | 6.59 | | 7.72 | 77.85 | 6.77 | | 7.70 | δ5.0-9.0 8H<br>δ0.5-4.5 20H |
| 39 | 18 | 78.29 | 7.36 | | 7.32 | 78.34 | 7.25 | | 7.21 | δ5.0-9.0 10H<br>δ0.5-4.5 22H |
| 40 | 19 | 77.17 | 6.41 | | 8.34 | 77.28 | 6.23 | | 8.25 | δ5.0-9.0 10H<br>δ0.5-4.5 14H |
| 41 | 20 | 77.65 | 6.81 | | 7.62 | 77.85 | 6.77 | | 7.70 | δ5.0-9.0 8H<br>δ0.5-4.5 20H |
| 42 | 21 | 77.69 | 6.48 | | 8.06 | 77.58 | 6.51 | | 7.97 | δ5.0-9.0 8H<br>δ0.5-4.5 18H |

*Example Nos. of the chromene compounds are Example Nos. of the chromene compounds obtained by using the naphthol compounds of Examples.

Examples 43 to 51

Synthesis of Naphthol Compounds

Naphthol compounds were synthesized in the same manner as in Example 29. When the structures of the obtained products were analyzed by using the same structure confirming means as in Example 29, it was confirmed that they were the compounds represented by the structural formulas shown in Table 11. Table 12 shows the elemental analysis values, calculated values obtained from the structural formulas and characteristic ¹H-NMR spectra of these compounds.

TABLE 11

Example 43

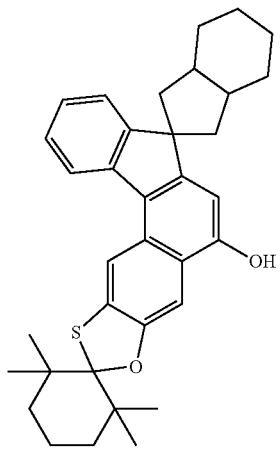 [SMILES: CC1(C)CCCC(C)(C)C12Oc1cc3c(O)cc4c(c3cc1S2)-c1ccccc1C41CC2CCCCC2C1]

TABLE 11-continued

Example 44

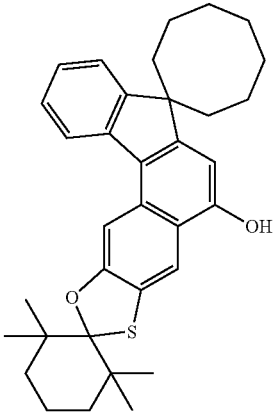 [SMILES: CC1(C)CCCC(C)(C)C12Oc1cc3c4c(cc(O)c3cc1S2)C1(CCCCCCC1)c1ccccc1-4]

Example 45

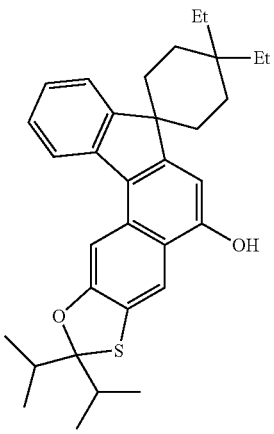

TABLE 11-continued
Example 46
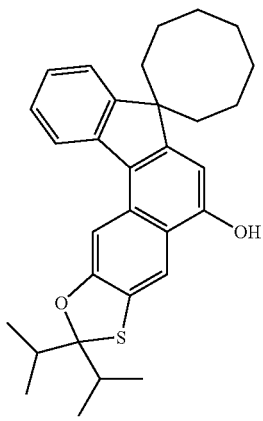 [SMILES: CC(C)C1(C(C)C)Oc2cc3c4c(cc(O)c3cc2S1)C1(CCCCCCC1)c1ccccc1-4]
Example 47
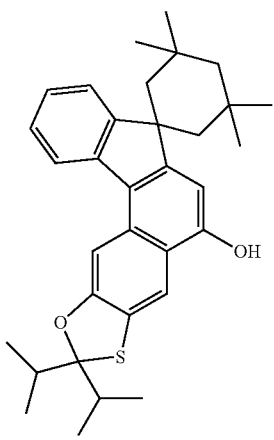 [SMILES: CC(C)C1(C(C)C)Oc2cc3c4c(cc(O)c3cc2S1)C1(CC(C)(C)CC(C)(C)C1)c1ccccc1-4]
Example 48
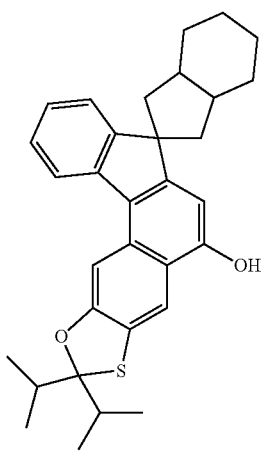 [SMILES: CC(C)C1(C(C)C)Oc2cc3c4c(cc(O)c3cc2S1)C1(CC2CCCCC2C1)c1ccccc1-4]
TABLE 11-continued
Example 49
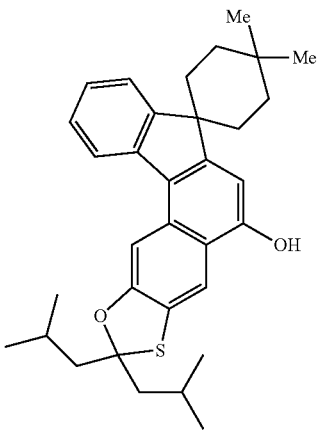 [SMILES: CC(C)CC1(CC(C)C)Oc2cc3c4c(cc(O)c3cc2S1)C1(CCC(C)(C)CC1)c1ccccc1-4]
Example 50
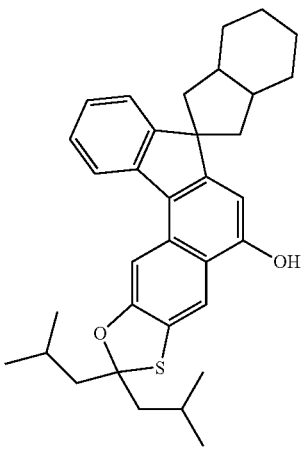 [SMILES: CC(C)CC1(CC(C)C)Oc2cc3c4c(cc(O)c3cc2S1)C1(CC2CCCCC2C1)c1ccccc1-4]
Example 51
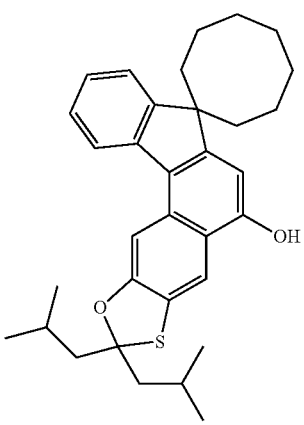 [SMILES: CC(C)CC1(CC(C)C)Oc2cc3c4c(cc(O)c3cc2S1)C1(CCCCCCC1)c1ccccc1-4]

TABLE 12

| Example No. | Experimental values | | | | Calculated values | | | | $^1$H-NMR (ppm) |
|---|---|---|---|---|---|---|---|---|---|
| | C | H | N | S | C | H | N | S | |
| 43 | 80.18 | 7.78 | | 6.22 | 80.11 | 7.68 | | 6.11 | δ5.0-9.0 8H<br>δ0.5-4.9 32H |
| 44 | 79.79 | 7.91 | | 6.14 | 79.64 | 7.86 | | 6.25 | δ5.0-9.0 8H<br>δ0.5-4.9 32H |
| 45 | 79.28 | 8.11 | | 6.33 | 79.15 | 8.05 | | 6.40 | δ5.0-9.0 8H<br>δ0.5-4.9 32H |
| 46 | 78.64 | 7.60 | | 6.94 | 78.77 | 7.68 | | 6.78 | δ5.0-9.0 8H<br>δ0.5-4.9 26H |
| 47 | 79.35 | 7.98 | | 5.30 | 79.15 | 8.05 | | 6.40 | δ5.0-9.0 8H<br>δ0.5-4.9 32H |
| 48 | 79.44 | 7.58 | | 6.47 | 79.30 | 7.49 | | 6.62 | δ5.0-9.0 8H<br>δ0.5-4.9 26H |
| 49 | 79.23 | 8.10 | | 6.58 | 79.15 | 8.05 | | 6.40 | δ5.0-9.0 8H<br>δ0.5-4.9 32H |
| 50 | 79.76 | 7.96 | | 6.06 | 79.64 | 7.86 | | 6.25 | δ5.0-9.0 8H<br>δ0.5-4.9 32H |
| 51 | 79.04 | 8.09 | | 6.45 | 79.15 | 8.05 | | 6.40 | δ5.0-9.0 8H<br>δ0.5-4.9 32H |

Examples 52 to 63

Synthesis of Chromene Compounds

Chromene compounds shown in Tables 13 to 15 were synthesized by using the naphthol compounds obtained in Examples 43 to 51. When the structures of the obtained products were analyzed by using the same structure confirming means as in Example 1, it was confirmed that they were compounds represented by the structural formulas shown in Tables 13 to 15. Table 16 shows the elemental analysis values, calculated values obtained from the structural formulas and characteristic $^1$H-NMR spectra of these compounds.

TABLE 13

| Ex. No. | Raw materials | | Product | Yield (%) |
|---|---|---|---|---|
| | Naphthol compound | Propargyl alcohol compound | | |

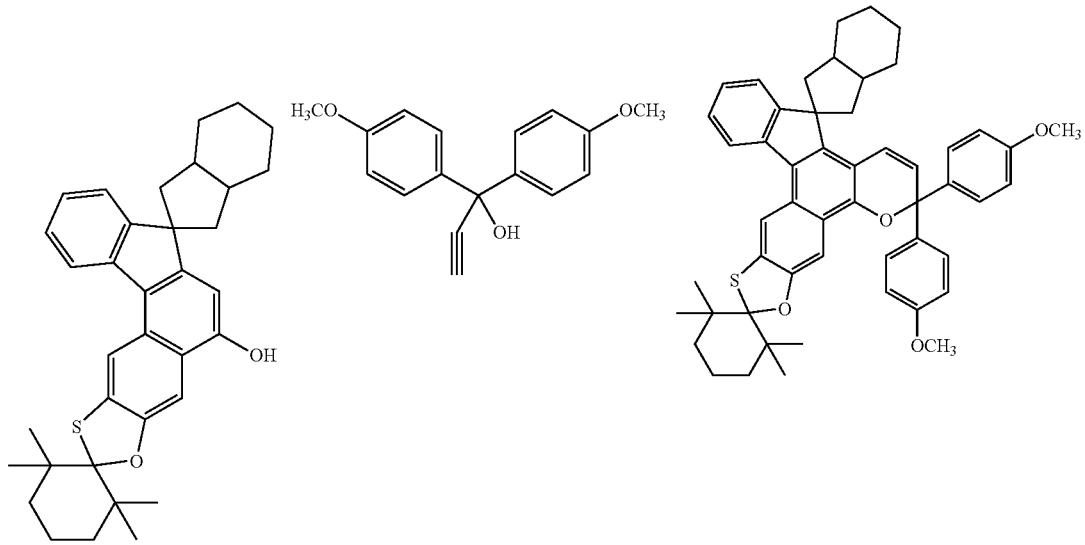

52      72

TABLE 13-continued

| | Raw materials | | | |
|---|---|---|---|---|
| Ex. No. | Naphthol compound | Propargyl alcohol compound | Product | Yield (%) |
| 53 | (structure) | (structure) | (structure) | 77 |
| 54 | (structure) | (structure) | (structure) | 74 |
| 55 | (structure) | (structure) | (structure) | 73 |

Ex.: Example

TABLE 14

| Ex. No. | Raw materials | | Product | Yield (%) |
|---|---|---|---|---|
| | Naphthol compound | Propargyl alcohol compound | | |
| 56 | | | | 69 |
| 57 | | | | 80 |
| 58 | | | | 73 |

TABLE 14-continued

| | Raw materials | | | |
|---|---|---|---|---|
| Ex. No. | Naphthol compound | Propargyl alcohol compound | Product | Yield (%) |
| 59 | | | | 70 |

Ex.: Example

TABLE 15

| | Raw materials | | | |
|---|---|---|---|---|
| Ex. No | Naphthol compound | Propargyl alcohol compound | Product | Yield (%) |
| 60 | | | | 59 |
| 61 | | | | 81 |

TABLE 15-continued

| Ex. No | Naphthol compound | Propargyl alcohol compound | Product | Yield (%) |
|---|---|---|---|---|
| 62 | (structure) | (structure) | (structure) | 77 |
| 63 | (structure) | (structure) | (structure) | 68 |

Ex.: Example

TABLE 16

| Example No. | Experimental values | | | | Calculated values | | | | $^1$H-NMR (ppm) |
|---|---|---|---|---|---|---|---|---|---|
| | C | H | N | S | C | H | N | S | |
| 52 | 80.34 | 7.19 | | 4.25 | 80.58 | 7.02 | | 4.14 | δ5.0-9.0 16H<br>δ0.5-4.9 38H |
| 53 | 80.26 | 7.37 | | 4.18 | 80.28 | 7.13 | | 4.20 | δ5.0-9.0 16H<br>δ0.5-4.9 38H |
| 54 | 80.57 | 7.65 | | 3.82 | 80.36 | 7.74 | | 3.97 | δ5.0-9.0 16H<br>δ0.5-4.9 46H |
| 55 | 79.91 | 7.36 | | 4.07 | 79.96 | 7.25 | | 4.27 | δ5.0-9.0 16H<br>δ0.5-4.9 38H |
| 56 | 78.83 | 7.26 | 1.94 | 4.34 | 78.73 | 7.13 | 1.80 | 4.12 | δ5.0-9.0 16H<br>δ0.5-4.9 39H |
| 57 | 79.79 | 7.16 | | 4.49 | 79.96 | 7.25 | | 4.27 | δ5.0-9.0 16H<br>δ0.5-4.9 38H |
| 58 | 79.87 | 6.89 | | 4.41 | 80.07 | 6.86 | | 4.36 | δ5.0-9.0 16H<br>δ0.5-4.9 34H |
| 59 | 80.54 | 7.11 | 1.84 | 4.03 | 80.69 | 7.10 | 1.81 | 4.14 | δ5.0-9.0 16H<br>δ0.5-4.9 39H |
| 60 | 82.36 | 7.43 | 1.92 | 4.41 | 82.39 | 7.31 | 1.85 | 4.23 | δ5.0-9.0 17H<br>δ0.5-4.9 38H |
| 61 | 81.65 | 7.66 | | 4.21 | 81.70 | 7.41 | | 4.36 | δ5.0-9.0 16H<br>δ0.5-4.9 38H |
| 62 | 80.41 | 7.03 | | 4.16 | 80.28 | 7.13 | | 4.20 | δ5.0-9.0 16H<br>δ0.5-4.9 38H |
| 63 | 79.06 | 7.20 | 1.65 | 4.17 | 78.97 | 7.38 | 1.74 | 3.98 | δ5.0-9.0 16H<br>δ0.5-4.9 40H |

Examples 64 to 75

Evaluation of Physical Properties of Photochromic Plastic Lenses Manufactured by Coating Method Photochromic plastic lenses were manufactured and their characteristic properties were evaluated in the same manner as in Example 8 except that the compounds obtained in Examples 52 to 63 were used as the chromene compound. The results are shown in Table 17. In Table 17, compounds Nos. 52 to 63 are the chromene compounds obtained in Examples 52 to 63, respectively. For example, the chromene compound obtained in Example 52 is represented as compound No. 52.

TABLE 17

| Example No. | Compound No. | λmax (nm) | Color optical density $A_0$ | Double peak characteristic $A_Y/A_B$ | Fading half period $\tau^{1/2}$ (sec) | Initial coloration (absorption end) (nm) | Initial coloration (thermochromism) (%) | Residual rate $(A_{50}/A_0) \times 100$ (%) | Double peak characteristic after heating $A_Y'/A_B'$ | Color drift $1 - (A_Y/A_B)/(A_Y'/A_B')$ |
|---|---|---|---|---|---|---|---|---|---|---|
| 64 | 52 | 462 | 0.83 | 1.70 | 93 | 414 | 85 | 88 | 1.69 | 0.01 |
|    |    | 575 | 0.49 |      | 93  |     | 87 | 88 |      |      |
| 65 | 53 | 464 | 0.91 | 1.63 | 120 | 400 | 84 | 87 | 1.63 | 0.00 |
|    |    | 573 | 0.56 |      | 120 |     | 85 | 87 |      |      |
| 66 | 54 | 468 | 0.73 | 1.48 | 78  | 400 | 87 | 86 | 1.47 | 0.01 |
|    |    | 570 | 0.49 |      | 79  |     | 87 | 86 |      |      |
| 67 | 55 | 468 | 0.74 | 1.48 | 78  | 401 | 87 | 86 | 1.47 | 0.01 |
|    |    | 570 | 0.49 |      | 78  |     | 87 | 86 |      |      |
| 68 | 56 | 482 | 0.45 | 1.16 | 61  | 400 | 88 | 88 | 1.15 | 0.01 |
|    |    | 586 | 0.39 |      | 61  |     | 88 | 88 |      |      |
| 69 | 57 | 462 | 0.52 | 1.49 | 39  | 400 | 89 | 85 | 1.46 | 0.02 |
|    |    | 570 | 0.35 |      | 38  |     | 90 | 85 |      |      |
| 70 | 58 | 463 | 0.81 | 1.56 | 93  | 399 | 84 | 87 | 1.55 | 0.01 |
|    |    | 574 | 0.52 |      | 94  |     | 85 | 87 |      |      |
| 71 | 59 | 480 | 0.66 | 1.09 | 72  | 400 | 86 | 88 | 1.07 | 0.02 |
|    |    | 580 | 0.61 |      | 72  |     | 86 | 88 |      |      |
| 72 | 60 | 490 | 0.61 | 0.96 | 48  | 400 | 87 | 89 | 0.95 | 0.01 |
|    |    | 590 | 0.64 |      | 49  |     | 87 | 89 |      |      |
| 73 | 61 | 452 | 0.89 | 1.23 | 110 | 401 | 84 | 81 | 1.19 | 0.03 |
|    |    | 563 | 0.72 |      | 112 |     | 85 | 81 |      |      |
| 74 | 62 | 464 | 0.80 | 1.54 | 88  | 400 | 85 | 86 | 1.48 | 0.04 |
|    |    | 570 | 0.52 |      | 88  |     | 86 | 86 |      |      |
| 75 | 63 | 483 | 0.69 | 1.52 | 67  | 401 | 86 | 87 | 1.46 | 0.04 |
|    |    | 588 | 0.45 |      | 67  |     | 87 | 87 |      |      |

Example 76

Evaluation Results of Heat Resistance

The evaluation results of the heat resistances of the compounds of the above Examples and Comparative Examples were collected. In the chromene compound represented by the formula (1), the differences in heat resistance due to the differences in $R^1$ and $R^2$ are shown in Table 18. As for the evaluation of heat resistance, a color drift [8] described in Example 8 and also yellowness [9] were evaluated. For comparison, the result of the heat resistance of the lens obtained in Comparative Example 4 is also shown in Table 18.

[9] yellowness: The YI value after a heating test and the YI value before the heating test were measured by using the color difference meter (SM-4) of Suga Test Instruments Co., Ltd. to evaluate the difference between them as an index of yellowness. The YI value is a yellow index and as this value becomes larger, yellowness becomes higher. The yellowness is a change in YI value. It can be said that as this value becomes smaller, the coloration of a sample by heating becomes less which means that heat resistance becomes higher. The heating test was carried out in the dark at 110° C. for 12 hours by using a blast oven like the color drift [8].

Table 18 also shows the surface area of a sulfur atom. As described above, heat resistance is connected with the bulkiness of each of the substituents $R^1$ and $R^2$. As the substituent becomes more bulky, the surface area of a sulfur atom which can be confirmed from a position where an oxygen atom is bonded to the sulfur atom becomes smaller. The surface area of a sulfur atom calculated by using the ChemPropStd of ChemBio3D (version 11.0) of Cambridge Software Co., Ltd. is shown in Table 18. The surface area is a relative value based on 100 when both $R^1$ and $R^2$ are hydrogen atoms.

In Table 18, compound No. corresponds to a chromene compound obtained in Example No. For example, the chromene compound obtained in Example 1 is represented as compound No. 1.

As obvious from these results, when a compound having bulky substituents as $R^1$ and $R^2$ is used, yellowness and a color drift were suppressed. As for a color drift in particular, when substituents having a relative value of the surface area of the sulfur atom of 80 or less are used, their effect of improving heat resistance is obtained and when substituents having a relative value of the surface area of the sulfur atom of 60 or less are used, their effect is marked.

Examples 77 to 94

Synthesis of Naphthol Compounds

Naphthol compounds were synthesized in the same manner as in Example 29. When the structures of the obtained products were analyzed by using the same structure confirming means as in Example 29, it was confirmed that they were compounds represented by the structural formulas shown in Tables 19 and 20. Table 21 shows the elemental analysis values, calculated values obtained from the structural formulas and characteristic $^1$H-NMR spectra of these compounds.

TABLE 19

Example 77

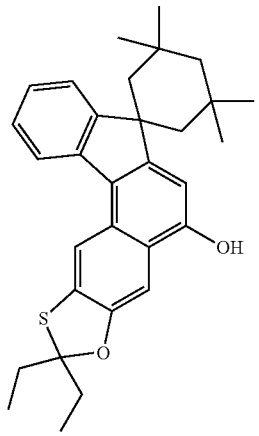 [SMILES: CCC1(CC)Oc2cc3c(O)cc4c(c3cc2S1)-c1ccccc1C41CC(C)(C)CC(C)(C)C1]

TABLE 18

| Compound No. | $R^1$ and $R^2$ | Surface area of sulfur atom (relative value) | Lens | Yellowness | Color drift |
| --- | --- | --- | --- | --- | --- |
| 1 | Hydrogen atom | 100 | Example 8 | 2.5 | 0.22 |
| 2 | Hydrogen atom | 100 | Example 9 | 1.4 | 0.23 |
| 15 | Methyl group | 78 | Example 22 | 2.7 | 0.12 |
| 52 | 2,2,6,6-tetramethyl-cyclohexane | 40 | Example 64 | 1.3 | 0.01 |
| 53 | 2,2,6,6-tetramethyl-cyclohexane | 40 | Example 65 | 0.6 | 0.00 |
| 57 | Isopropyl group | 42 | Example 69 | 0.8 | 0.02 |
| 62 | Isobuthyl group | 53 | Example 74 | 1.1 | 0.04 |
| (D) | — | | Comparative Example 4 | 2.2 | 0.25 |

TABLE 19-continued
Example 78
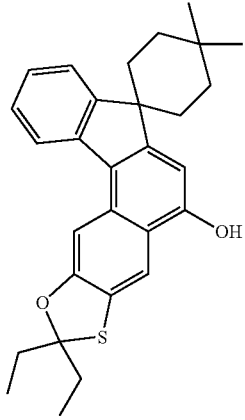 [SMILES: CCC1(CC)Oc2cc3c4c(cc(O)c3cc2S1)C1(CCC(C)(C)CC1)c1ccccc1-4]
Example 79
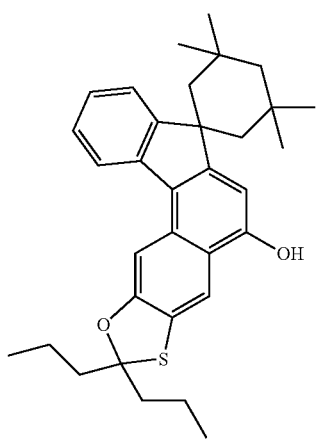 [SMILES: CCCC1(CCC)Oc2cc3c4c(cc(O)c3cc2S1)C1(CC(C)(C)CC(C)(C)C1)c1ccccc1-4]
Example 80
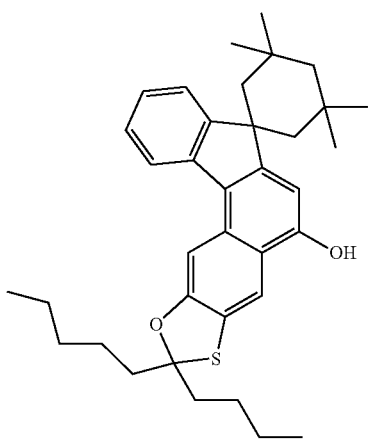 [SMILES: CCCCCC1(CCCC)Oc2cc3c4c(cc(O)c3cc2S1)C1(CC(C)(C)CC(C)(C)C1)c1ccccc1-4]
TABLE 19-continued
Example 81
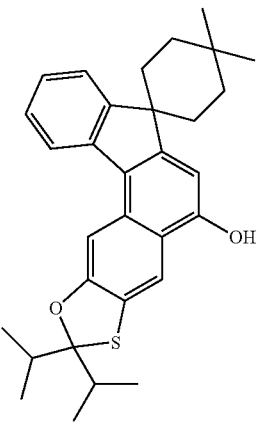 [SMILES: CC(C)C1(C(C)C)Oc2cc3c4c(cc(O)c3cc2S1)C1(CCC(C)(C)CC1)c1ccccc1-4]
Example 82
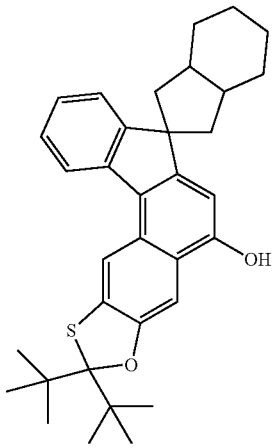 [SMILES: CC(C)(C)C1(C(C)(C)C)Oc2cc3c(O)cc4c(c3cc2S1)-c1ccccc1C41CC2CCCCC2C1]
Example 83
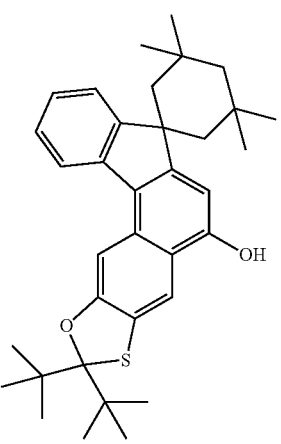 [SMILES: CC1(C)CC(C)(C)CC2(C1)c1ccccc1-c1c2cc(O)c2cc3c(cc12)OC(C(C)(C)C)(C(C)(C)C)S3]

TABLE 19-continued
Example 84
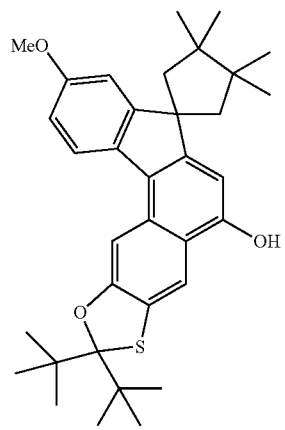 [SMILES: COc1ccc2c(c1)C1(CC(C)(C)C(C)(C)C1)c1cc(O)c3cc4c(cc3c1-2)OC(C(C)(C)C)(C(C)(C)C)S4]
Example 85
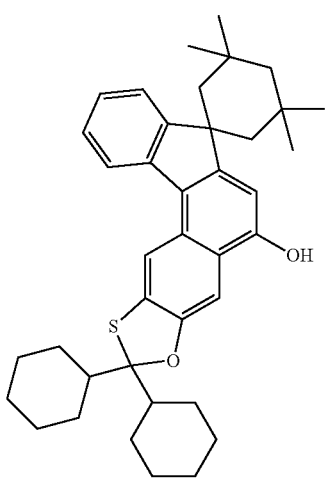 [SMILES: CC1(C)CC(C)(C)CC2(C1)c1ccccc1-c1c2cc(O)c2cc3c(cc12)SC(C1CCCCC1)(C1CCCCC1)O3]
TABLE 20
Example 86
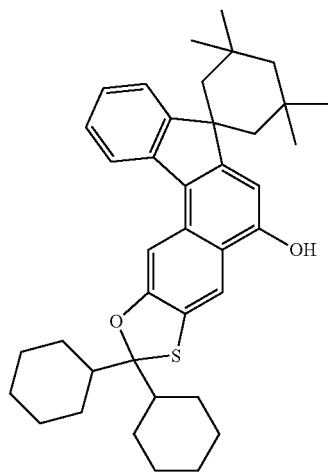 [SMILES: CC1(C)CC(C)(C)CC2(C1)c1ccccc1-c1c2cc(O)c2cc3c(cc12)OC(C1CCCCC1)(C1CCCCC1)S3]
TABLE 20-continued
Example 87
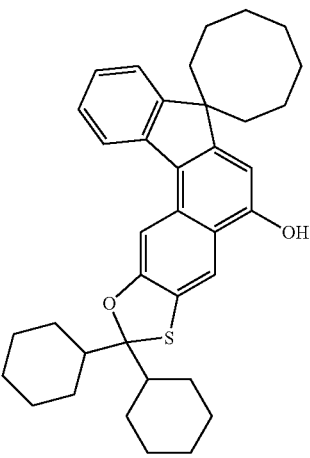 [SMILES: Oc1cc2c(c3cc4c(cc13)SC(C1CCCCC1)(C1CCCCC1)O4)-c1ccccc1C21CCCCCCC1]
Example 88
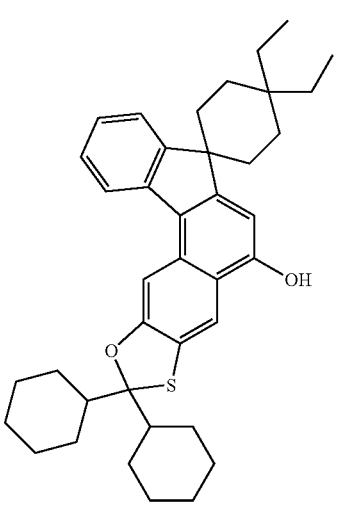 [SMILES: CCC1(CC)CCC2(CC1)c1ccccc1-c1c2cc(O)c2cc3c(cc12)OC(C1CCCCC1)(C1CCCCC1)S3]
Example 89
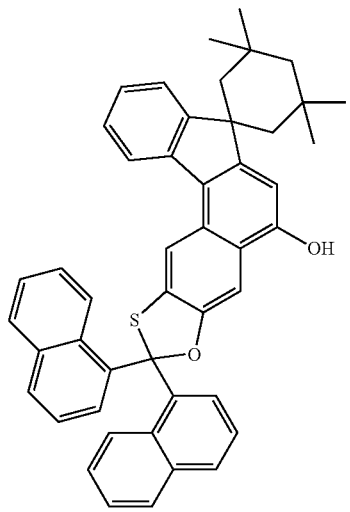 [SMILES: CC1(C)CC(C)(C)CC2(C1)c1ccccc1-c1c2cc(O)c2cc3c(cc12)SC(c1cccc2ccccc12)(c1cccc2ccccc12)O3]

TABLE 20-continued
Example 90
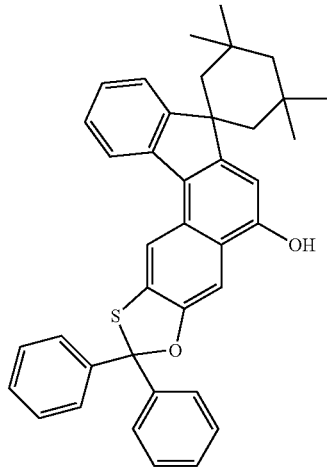 [SMILES: CC1(C)CC(C)(C)CC2(C1)c1ccccc1-c1c2cc(O)c2cc3c(cc12)SC(c1ccccc1)(c1ccccc1)O3]
Example 91
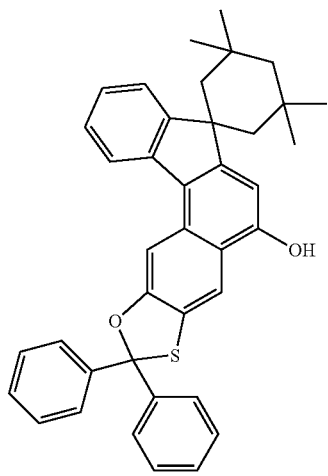 [SMILES: CC1(C)CC(C)(C)CC2(C1)c1ccccc1-c1c2cc(O)c2cc3c(cc12)OC(c1ccccc1)(c1ccccc1)S3]
Example 92
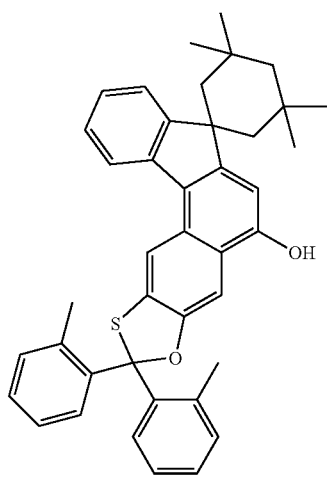 [SMILES: Cc1ccccc1C1(c2ccccc2C)Oc2cc3c(O)cc4c(c3cc2S1)-c1ccccc1C41CC(C)(C)CC(C)(C)C1]
TABLE 20-continued
Example 93
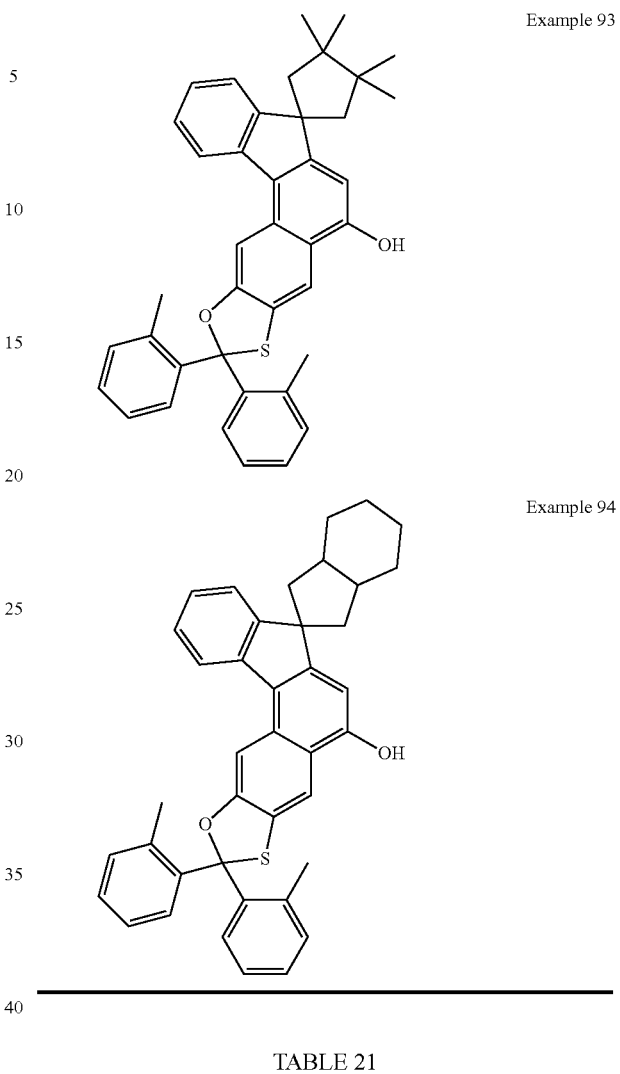
Example 94
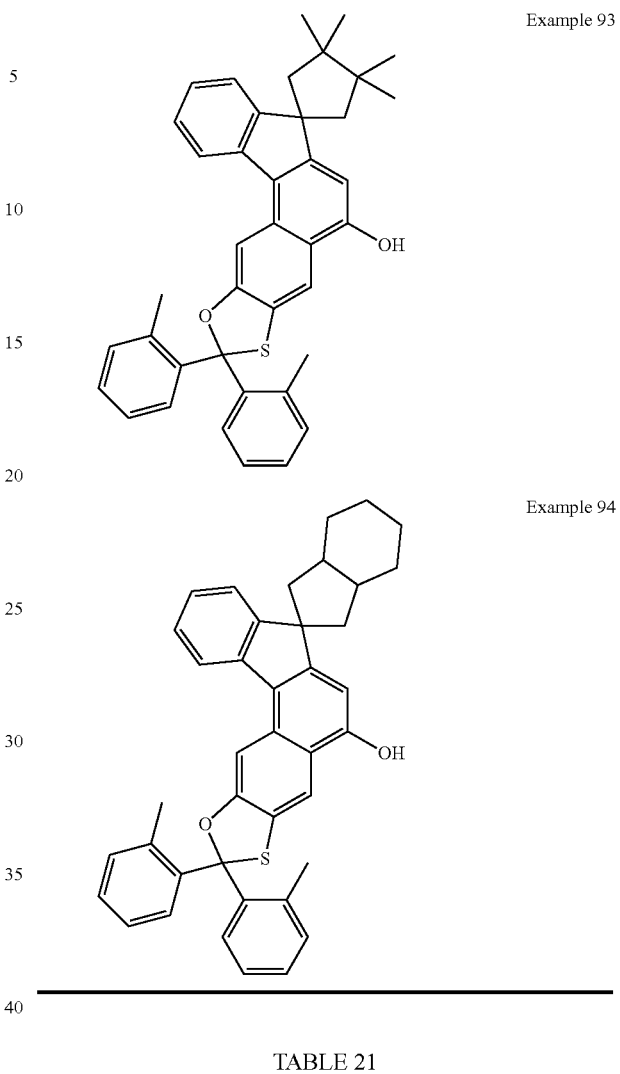
TABLE 21
| Example No. | Experimental values | | | Calculated values | | | $^1$H-NMR (ppm) |
|---|---|---|---|---|---|---|---|
| | C | H | S | C | H | S | |
| 77 | 78.89 | 7.54 | 6.75 | 78.77 | 7.68 | 6.78 | δ5.0-9.0 8H<br>δ0.5-4.9 28H |
| 78 | 78.52 | 7.16 | 6.97 | 78.34 | 7.25 | 7.21 | δ5.0-9.0 8H<br>δ0.5-4.9 24H |
| 79 | 78.95 | 8.18 | 6.38 | 79.15 | 8.05 | 6.40 | δ5.0-9.0 8H<br>δ0.5-4.9 32H |
| 80 | 79.53 | 8.57 | 6.04 | 79.66 | 8.54 | 5.91 | δ5.0-9.0 8H<br>δ0.5-4.9 38H |
| 81 | 78.60 | 7.81 | 6.65 | 78.77 | 7.68 | 6.78 | δ5.0-9.0 8H<br>δ0.5-4.9 28H |
| 82 | 79.74 | 7.71 | 6.18 | 79.64 | 7.86 | 6.25 | δ5.0-9.0 8H<br>δ0.5-4.9 32H |
| 83 | 79.43 | 8.50 | 6.02 | 79.50 | 8.39 | 6.06 | δ5.0-9.0 8H<br>δ0.5-4.9 36H |
| 84 | 77.08 | 8.27 | 5.99 | 77.16 | 8.14 | 5.89 | δ5.0-9.0 7H<br>δ0.5-4.9 37H |
| 85 | 80.61 | 8.34 | 5.73 | 80.64 | 8.33 | 5.52 | δ5.0-9.0 8H<br>δ0.5-4.9 40H |
| 86 | 80.57 | 8.28 | 5.64 | 80.64 | 8.33 | 5.52 | δ5.0-9.0 8H<br>δ0.5-4.9 40H |
| 87 | 80.32 | 7.89 | 5.78 | 80.39 | 8.02 | 5.79 | δ5.0-9.0 8H<br>δ0.5-4.9 36H |
| 88 | 80.89 | 8.18 | 5.31 | 80.64 | 8.33 | 5.52 | δ5.0-9.0 8H<br>δ0.5-4.9 40H |

TABLE 21-continued

| Example No. | Experimental values | | | Calculated values | | | ¹H-NMR (ppm) |
|---|---|---|---|---|---|---|---|
| | C | H | S | C | H | S | |
| 89 | 84.56 | 5.99 | 4.69 | 84.39 | 6.03 | 4.79 | δ5.0-9.0 22H<br>δ0.5-4.9 18H |
| 90 | 82.15 | 6.52 | 5.78 | 82.36 | 6.38 | 5.64 | δ5.0-9.0 18H<br>δ0.5-4.9 18H |
| 91 | 82.42 | 6.26 | 5.60 | 82.36 | 6.38 | 5.64 | δ5.0-9.0 18H<br>δ0.5-4.9 18H |
| 92 | 82.75 | 6.71 | 5.27 | 82.51 | 6.76 | 5.37 | δ5.0-9.0 16H<br>δ0.5-4.9 24H |
| 93 | 82.31 | 6.40 | 5.62 | 82.44 | 6.57 | 5.50 | δ5.0-9.0 16H<br>δ0.5-4.9 22H |
| 94 | 82.86 | 6.01 | 5.62 | 82.72 | 6.25 | 5.52 | δ5.0-9.0 16H<br>δ0.5-4.9 20H |

Examples 95 to 118

Synthesis of Chromene Compounds

Chromene compounds shown in Tables 22 to 27 were synthesized in the same manner as in Example 1 except that the naphthol compounds obtained in Examples 77 to 95 were used. When the structures of the obtained products were analyzed by using the same structure confirming means as in Example 1, it was confirmed that they were compounds represented by the structural formulas shown in Tables 22 to 27. Table 28 shows the elemental analysis values, calculated values obtained from the structural formulas and characteristic ¹H-NMR spectra of these compounds.

TABLE 22

| Ex. No. | Raw materials | | Product | Yield (%) |
|---|---|---|---|---|
| | Naphthol compound | Propargyl alcohol compound | | |
| 95 | | | | 69 |

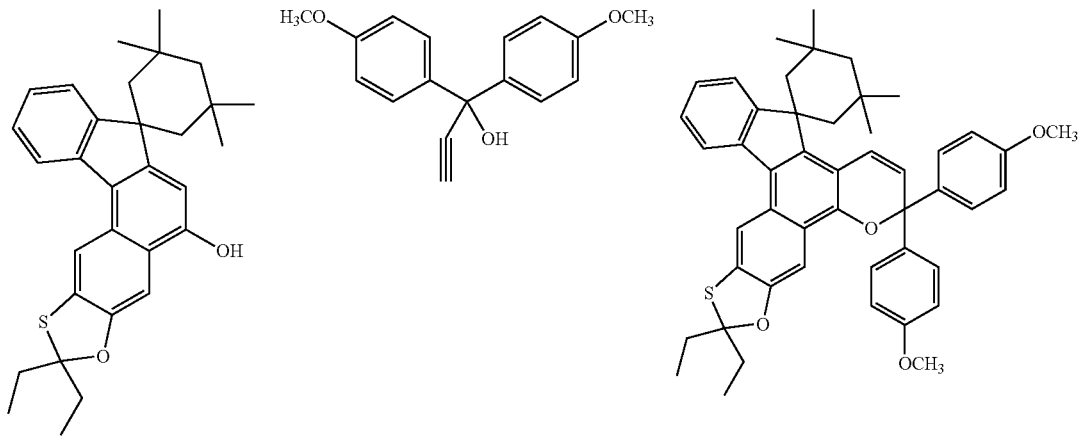

| 96 | | | | 72 |

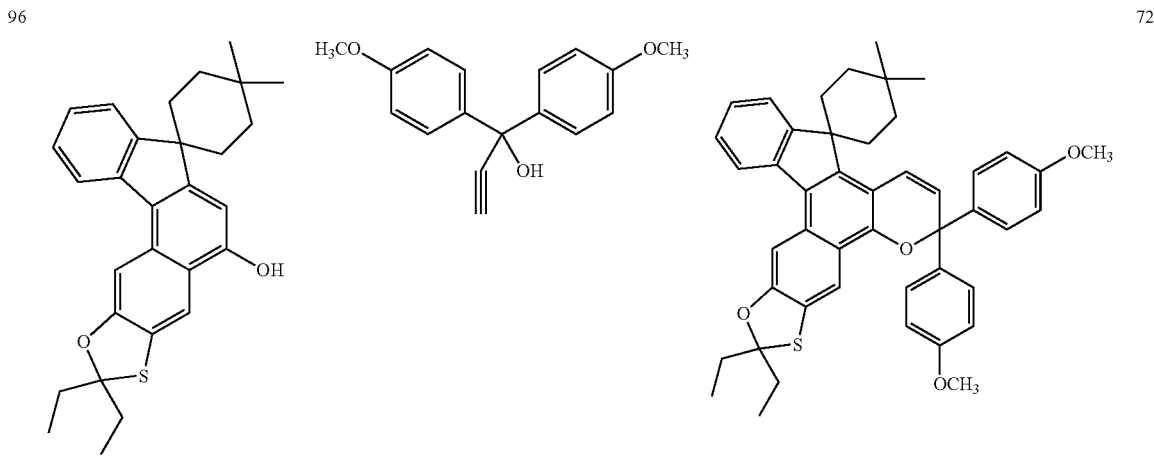

TABLE 22-continued

| | Raw materials | | | |
|---|---|---|---|---|
| Ex. No. | Naphthol compound | Propargyl alcohol compound | Product | Yield (%) |
| 97 | (structure) | (structure) | (structure) | 57 |
| 98 | (structure) | (structure) | (structure) | 80 |

Ex.: Example

TABLE 23

| | Raw materials | | | |
|---|---|---|---|---|
| Ex. No. | Naphthol compound | Propargyl alcohol compound | Product | Yield (%) |
| 99 | (structure) | (structure) | (structure) | 74 |

TABLE 23-continued

| | Raw materials | | | |
|---|---|---|---|---|
| Ex. No. | Naphthol compound | Propargyl alcohol compound | Product | Yield (%) |
| 100 | | | | 72 |
| 101 | | | | 70 |
| 102 | | | | 67 |

Ex.: Example

TABLE 24

| Ex. No. | Raw materials Naphthol compound | Propargyl alcohol compound | Product | Yield (%) |
|---|---|---|---|---|
| 103 | | | | 68 |
| 104 | | | | 79 |
| 105 | | | | 71 |
| 106 | | | | 74 |

Ex.: Example

TABLE 25

| Ex. No. | Raw materials | | Product | Yield (%) |
| --- | --- | --- | --- | --- |
| | Naphthol compound | Propargyl alcohol compound | | |
| 107 | | | | 62 |
| 108 | | | | 80 |
| 109 | | | | 63 |
| 110 | | | | 79 |

Ex.: Example

TABLE 26

| Ex. No. | Naphthol compound | Propargyl alcohol compound | Product | Yield (%) |
|---|---|---|---|---|
| 111 | | | | 80 |
| 112 | | | | 49 |
| 113 | | | | 51 |
| 114 | | | | 47 |

Ex.: Example

TABLE 27

| Ex. No. | Raw materials - Naphthol compound | Raw materials - Propargyl alcohol compound | Product | Yield (%) |
|---|---|---|---|---|
| 115 | (structure) | (structure) | (structure) | 68 |
| 116 | (structure) | (structure) | (structure) | 70 |
| 117 | (structure) | (structure) | (structure) | 70 |
| 118 | (structure) | (structure) | (structure) | 66 |

Ex.: Example

TABLE 28

| | Experimental values | | | | Calculated values | | | | |
|---|---|---|---|---|---|---|---|---|---|
| Ex. No. | C | H | N | S | C | H | N | S | $^1$H-NMR (ppm) |
| 95 | 79.59 | 6.90 | | 4.41 | 79.74 | 6.97 | | 4.44 | δ5.0-9.0 16H<br>δ0.5-4.9 32H |
| 96 | 79.27 | 6.58 | | 4.78 | 79.50 | 6.67 | | 4.61 | δ5.0-9.0 16H<br>δ0.5-4.9 30H |

TABLE 28-continued

| Ex. No. | Experimental values | | | | Calculated values | | | | $^1$H-NMR (ppm) |
|---|---|---|---|---|---|---|---|---|---|
| | C | H | N | S | C | H | N | S | |
| 97 | 78.54 | 6.82 | 1.98 | 4.08 | 78.47 | 6.85 | 1.87 | 4.28 | δ5.0-9.0 16H<br>δ0.5-4.9 35H |
| 98 | 80.11 | 7.20 | | 4.19 | 80.07 | 7.38 | | 4.19 | δ5.0-9.0 16H<br>δ0.5-4.9 40H |
| 99 | 80.21 | 7.13 | | 4.14 | 80.28 | 7.13 | | 4.20 | δ5.0-9.0 16H<br>δ0.5-4.9 38H |
| 100 | 80.32 | 7.43 | | 4.08 | 80.17 | 7.50 | | 4.12 | δ5.0-9.0 16H<br>δ0.5-4.9 42H |
| 101 | 78.40 | 7.39 | | 4.14 | 78.55 | 7.35 | | 4.03 | δ5.0-9.0 15H<br>δ0.5-4.9 43H |
| 102 | 80.70 | 7.68 | | 3.96 | 80.92 | 7.52 | | 3.86 | δ5.0-9.0 16H<br>δ0.5-4.9 46H |
| 103 | 80.19 | 7.13 | | 4.20 | 80.28 | 7.13 | | 4.20 | δ5.0-9.0 16H<br>δ0.5-4.9 38H |
| 104 | 80.22 | 7.61 | | 4.08 | 80.17 | 7.50 | | 4.12 | δ5.0-9.0 16H<br>δ0.5-4.9 42H |
| 105 | 78.65 | 7.42 | | 4.03 | 78.55 | 7.35 | | 4.03 | δ5.0-9.0 15H<br>δ0.5-4.9 43H |
| 106 | 80.76 | 7.66 | | 3.94 | 80.92 | 7.52 | | 3.86 | δ5.0-9.0 16H<br>δ0.5-4.9 46H |
| 107 | 80.01 | 7.58 | 1.51 | 3.71 | 79.96 | 7.62 | 1.58 | 3.62 | δ5.0-9.0 16H<br>δ0.5-4.9 51H |
| 108 | 80.92 | 7.66 | | 3.82 | 80.92 | 7.52 | | 3.86 | δ5.0-9.0 16H<br>δ0.5-4.9 46H |
| 109 | 80.14 | 7.55 | 1.48 | 3.54 | 79.96 | 7.62 | 1.58 | 3.62 | δ5.0-9.0 16H<br>δ0.5-4.9 51H |
| 110 | 81.02 | 7.69 | | 3.73 | 81.08 | 7.74 | | 3.73 | δ5.0-9.0 16H<br>δ0.5-4.9 50H |
| 111 | 80.77 | 7.57 | | 3.85 | 80.92 | 7.52 | | 3.86 | δ5.0-9.0 16H<br>δ0.5-4.9 46H |
| 112 | 83.68 | 5.82 | | 3.39 | 83.63 | 5.92 | | 3.49 | δ5.0-9.0 30H<br>δ0.5-4.9 20H |
| 113 | 82.16 | 6.26 | | 3.91 | 82.12 | 6.15 | | 3.91 | δ5.0-9.0 26H<br>δ0.5-4.9 24H |
| 114 | 82.34 | 6.23 | | 3.68 | 82.12 | 6.15 | | 3.91 | δ5.0-9.0 26H<br>δ0.5-4.9 24H |
| 115 | 82.23 | 6.28 | | 3.79 | 82.23 | 6.43 | | 3.79 | δ5.0-9.0 24H<br>δ0.5-4.9 30H |
| 116 | 82.37 | 6.06 | | 3.85 | 82.18 | 6.29 | | 3.85 | δ5.0-9.0 24H<br>δ0.5-4.9 28H |
| 117 | 82.33 | 6.15 | | 3.98 | 82.38 | 6.06 | | 3.86 | δ5.0-9.0 24H<br>δ0.5-4.9 26H |
| 118 | 81.36 | 6.40 | 1.55 | 3.50 | 81.32 | 6.26 | 1.58 | 3.62 | δ5.0-9.0 24H<br>δ0.5-4.9 31H |

Ex.: Example

Examples 119 to 142

Evaluation of Physical Properties of Photochromic Plastic Lenses Manufactured by Coating Method Photochromic plastic lenses were manufactured and their characteristic properties were evaluated in the same manner as in Example 8 except that the compounds obtained in Examples 95 to 118 were used as the chromene compound. The results are shown in Table 29. In Table 29, compounds Nos. 95 to 118 are chromene compounds obtained in Examples 95 to 118, respectively. For example, the chromene compound obtained in Example 95 is represented as compound No. 95.

TABLE 29

| Ex. No. | Compound No. | λmax (nm) | Color optical density $A_0$ | Double peak characteristic $A_Y/A_B$ | Fading half period $\tau^{1/2}$ (sec) | Initial coloration (absorption end) (nm) |
|---|---|---|---|---|---|---|
| 119 | 95 | 466<br>569 | 0.54<br>0.38 | 1.42 | 45<br>45 | 412 |
| 120 | 96 | 467<br>570 | 0.77<br>0.56 | 1.38 | 90<br>91 | 400 |
| 121 | 97 | 481<br>582 | 0.58<br>0.57 | 1.02 | 77<br>77 | 400 |
| 122 | 98 | 462<br>570 | 0.56<br>0.39 | 1.44 | 44<br>44 | 400 |
| 123 | 99 | 462<br>571 | 0.57<br>0.40 | 1.43 | 46<br>46 | 401 |
| 124 | 100 | 466<br>576 | 0.76<br>0.50 | 1.52 | 85<br>84 | 400 |
| 125 | 101 | 484<br>585 | 0.58<br>0.48 | 1.21 | 70<br>70 | 400 |
| 126 | 102 | 461<br>568 | 0.72<br>0.49 | 1.47 | 81<br>81 | 413 |
| 127 | 103 | 458<br>571 | 0.83<br>0.49 | 1.69 | 98<br>98 | 411 |
| 128 | 104 | 460<br>571 | 0.61<br>0.38 | 1.61 | 46<br>46 | 399 |
| 129 | 105 | 478<br>575 | 0.65<br>0.38 | 1.71 | 62<br>61 | 408 |
| 130 | 106 | 460<br>571 | 0.53<br>0.34 | 1.56 | 41<br>41 | 412 |
| 131 | 107 | 479<br>584 | 0.51<br>0.43 | 1.19 | 38<br>38 | 411 |
| 132 | 108 | 459<br>570 | 0.54<br>0.35 | 1.54 | 44<br>44 | 399 |

TABLE 29-continued

| | | | | | | |
|---|---|---|---|---|---|---|
| 133 | 109 | 479 | 0.50 | 1.19 | 40 | 400 |
| | | 585 | 0.42 | | 40 | |
| 134 | 110 | 464 | 0.89 | 1.59 | 118 | 400 |
| | | 572 | 0.56 | | 117 | |
| 135 | 111 | 465 | 0.77 | 1.51 | 89 | 400 |
| | | 572 | 0.51 | | 89 | |
| 136 | 112 | 470 | 0.66 | 1.57 | 58 | 415 |
| | | 579 | 0.42 | | 58 | |
| 137 | 113 | 462 | 0.62 | 1.55 | 51 | 413 |
| | | 578 | 0.40 | | 51 | |
| 138 | 114 | 462 | 0.66 | 1.50 | 56 | 400 |
| | | 574 | 0.44 | | 56 | |
| 139 | 115 | 464 | 0.61 | 1.69 | 50 | 412 |
| | | 575 | 0.36 | | 50 | |
| 140 | 116 | 466 | 0.60 | 1.67 | 48 | 399 |
| | | 568 | 0.36 | | 48 | |
| 141 | 117 | 459 | 0.85 | 1.70 | 90 | 399 |
| | | 576 | 0.50 | | 90 | |
| 142 | 118 | 482 | 0.64 | 1.28 | 81 | 400 |
| | | 587 | 0.50 | | 81 | |

| Example No. | Initial coloration (thermochromism) (%) | Residual rate $(A_{50}/A_0) \times 100$ (%) | Double peak characteristic after heating $A_{Y'}/A_{B'}$ | Color drift $1 - (A_{Y}/A_{B})/(A_{Y'}/A_{B'})$ |
|---|---|---|---|---|
| 119 | 88 / 88 | 85 / 85 | 1.25 | 0.12 |
| 120 | 84 / 85 | 85 / 85 | 1.21 | 0.12 |
| 121 | 86 / 86 | 87 / 87 | 0.89 | 0.13 |
| 122 | 89 / 89 | 84 / 85 | 1.26 | 0.12 |
| 123 | 89 / 89 | 84 / 84 | 1.24 | 0.13 |
| 124 | 86 / 87 | 86 / 86 | 1.49 | 0.02 |
| 125 | 87 / 87 | 86 / 86 | 1.19 | 0.02 |
| 126 | 86 / 86 | 87 / 87 | 1.45 | 0.01 |
| 127 | 84 / 85 | 84 / 84 | 1.69 | 0.00 |
| 128 | 89 / 89 | 88 / 88 | 1.61 | 0.00 |
| 129 | 86 / 87 | 81 / 81 | 1.7 | 0.01 |
| 130 | 90 / 90 | 87 / 87 | 1.54 | 0.01 |
| 131 | 90 / 90 | 86 / 86 | 1.16 | 0.02 |
| 132 | 89 / 89 | 86 / 86 | 1.53 | 0.01 |
| 133 | 88 / 88 | 87 / 87 | 1.18 | 0.01 |
| 134 | 84 / 85 | 85 / 85 | 1.57 | 0.01 |
| 135 | 87 / 87 | 86 / 86 | 1.48 | 0.02 |
| 136 | 88 / 88 | 85 / 85 | 1.54 | 0.02 |
| 137 | 88 / 89 | 85 / 86 | 1.42 | 0.08 |
| 138 | 88 / 88 | 87 / 87 | 1.36 | 0.09 |
| 139 | 89 / 90 | 84 / 84 | 1.67 | 0.01 |
| 140 | 88 / 88 | 83 / 83 | 1.64 | 0.02 |
| 141 | 85 / 86 | 83 / 84 | 1.68 | 0.01 |
| 142 | 87 / 87 | 86 / 86 | 1.26 | 0.02 |

Ex.: Example

Examples 143 to 157

Evaluation of Heat Resistances of In-Mass Lenses

Photochromic cured products were manufactured by the in-mass technology to evaluate their heat resistances. That is, 0.04 part by mass of the chromene compound of the present invention, 13 parts by mass of tetraethylene glycol dimethacrylate, 48 parts by mass of 2,2-bis[4-(methacryloxyethoxy)phenyl]propane, 2 parts by mass of polyethylene glycol monoallyl ether, 20 parts by mass of trimethylolpropane trimethacrylate, 9 parts by mass of glycidyl methacrylate and 1 part by mass of t-butylperoxy-2-ethyl hexanate were fully mixed together to prepare a photochromic curable composition. Then, the obtained composition was cast into a mold composed of a glass sheet and a gasket made of an ethylene-vinyl acetate copolymer to carry out cast polymerization. Polymerization was carried out by using an air furnace, gradually raising the temperature from 30° C. to 90° C. over 18 hours and maintaining the temperature at 90° C. for 2 hours. After the end of polymerization, the obtained polymer was removed from the cast glass mold. A heating test was conducted on the obtained polymer (thickness of 2 mm) as a sample at 110° C. for 12 hours. Photochromic properties before and after the heating test were measured to evaluate a drift of a developed color so as to evaluate heat resistance. The results are shown in Table 30. Compounds Nos. in Table 30 are chromene compounds synthesized in Examples 1 to 117, respectively. For example, the chromene compound obtained in Example 1 is represented as compound No. 1.

TABLE 30

| Example No. | Compound No. | $R^1$ and $R^2$ | Surface area of sulfur atom (relative value) | Double peak characteristic before heating | Double peak characteristic after heating | Color drift |
|---|---|---|---|---|---|---|
| 143 | 1 | Hydrogen atom | 100 | 1.50 | 1.17 | 0.22 |
| 144 | 2 | Hydrogen atom | 100 | 1.47 | 1.11 | 0.24 |
| 145 | 15 | Methyl group | 78 | 1.50 | 1.29 | 0.14 |
| 146 | 52 | 2,2,6,6-tetramethylcyclohexane | 40 | 1.70 | 1.68 | 0.01 |
| 147 | 53 | 2,2,6,6-tetramethylcyclohexane | 40 | 1.62 | 1.61 | 0.01 |
| 148 | 57 | Isopropyl group | 42 | 1.49 | 1.48 | 0.01 |
| 149 | 62 | Isobuthyl group | 53 | 1.53 | 1.45 | 0.05 |
| 150 | 95 | Ethyl group | 73 | 1.41 | 1.23 | 0.13 |
| 151 | 98 | n-propyl group | 72 | 1.44 | 1.25 | 0.13 |
| 152 | 99 | n-buthyl group | 70 | 1.44 | 1.25 | 0.13 |
| 153 | 104 | Tert-buthyl group | 40 | 1.60 | 1.59 | 0.01 |
| 154 | 108 | Cyclohexyl group | 43 | 1.54 | 1.52 | 0.01 |

TABLE 30-continued

| Example No. | Compound No. | R¹ and R² | Surface area of sulfur atom (relative value) | Double peak characteristic before heating | Double peak characteristic after heating | Color drift |
|---|---|---|---|---|---|---|
| 155 | 112 | 2-naphthyl group | 42 | 1.58 | 1.55 | 0.02 |
| 156 | 114 | Phenyl group | 69 | 1.49 | 1.34 | 0.10 |
| 157 | 117 | 2-methylphenyl group | 41 | 1.68 | 1.64 | 0.02 |

Like the results of Example 76, it is understood that when a compound having bulky substituents as $R^1$ and $R^2$ was used even in an in-mass lens, a color drift was small and heat resistance was high.

Example 158

Synthesis of Naphthol Compound

A siloxane compound (MCR-C12 of Gelest Inc.) represented by the following formula (28) was tosylated by using tosyl chloride and then reacted with lithium bromide to obtain a bromo compound represented by the following formula (29).

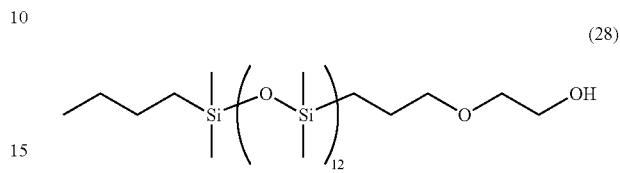

(28)

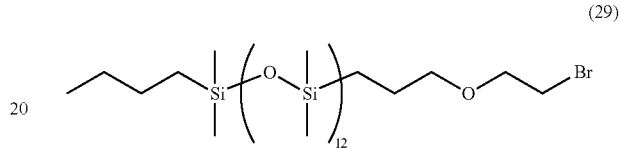

(29)

The bromo compound was reacted with a hydroxybenzophenone derivative to obtain a benzophenone derivative represented by the following formula (30).

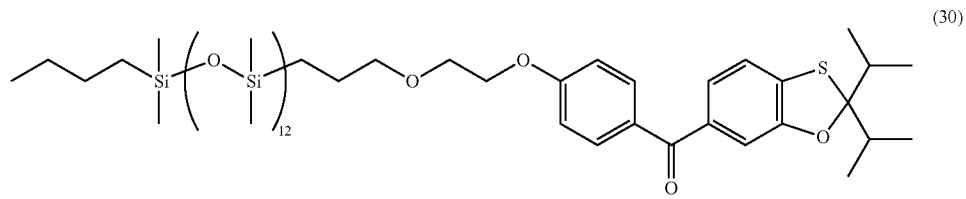

(30)

A naphthol compound represented by the following formula (31) was synthesized from this benzophenone derivative in the same manner as in Example 29.

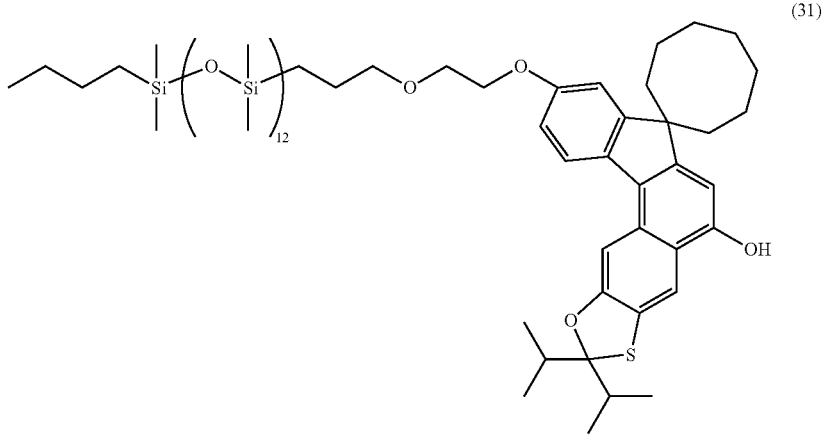

(31)

The elemental analysis values of this product were 51.56% of C, 8.38% of H and 2.10% of S which were almost equal to the calculated values of $C_{64}H_{126}O_{15}SSi_{12}$ (C: 51.08%, H: 8.44%, S: 2.13%).

When the proton nuclear magnetic resonance spectrum of the product was measured, it showed an about 80H peak based on the methyl (Si—CH$_3$) of polydimethylsiloxane at δ of around 0 to 0.5 ppm, about 50H peaks based on a methyl proton and a methylene proton at δ of around 0.5 to 5.0 ppm and 7H peaks based on an aromatic proton and the proton of a hydroxyl group at δ of around 5.0 to 9.0 ppm. It was confirmed that this product was a compound represented by the above formula (31).

Examples 159 to 162

Synthesis of Chromene Compounds

Chromene compounds shown in Tables 31 and 32 were synthesized in the same manner as in Example 1 except that the naphthol compounds obtained in Examples 45, 46 and 158 were used. When the structures of the obtained products were analyzed by using the same structure confirming means as in Example 1, it was confirmed that they were compounds represented by the structural formulas shown in Tables 31 and 32. Table 33 shows the elemental analysis values of these compounds.

The benzophenone derivative which is the precursor of propargyl alcohol used in Example 160 was obtained through a Williamoson reaction between the bromo compound represented by the above formula (29) and 4-hydroxy-4'-methoxybenzophenone under a basic condition.

The benzophenone derivative which is the precursor of propargyl alcohol used in Example 161 was obtained by hydrosilylating a mixture of a polydimethylsiloxane compound represented by the following formula (32), allyl methacrylate and 4-methoxy-4'-vinylbenzophenone in the presence of chloroplatinic acid as a catalyst.

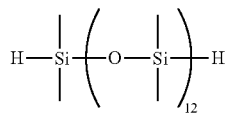
(32)

The benzophenone derivative which is the precursor of propargyl alcohol used in Example 162 was obtained by hydrosilylating a mixture of the polydimethylsiloxane compound represented by the above formula (32), divinylbenzene and 4-methoxy-4'-vinylbenzophenone in the presence of chloroplatinic acid as a catalyst.

TABLE 31

| Example No. | Raw materials Product | | Yield (%) |
|---|---|---|---|
| 159 | Naphthol compound | Propargyl alcohol compound | 53 |

Product

TABLE 31-continued

| Example No. | Raw materials Product | Yield (%) |
|---|---|---|
| 160 | Naphthol compound    Propargyl alcohol compound | 49 |
| | Product | |

TABLE 32

| Example No. | Raw materials Product | Yield (%) |
|---|---|---|
| 161 | Naphthol compound    Propargyl alcohol compound | 62 |

TABLE 32-continued

| Example No. | Raw materials Product | Yield (%) |
|---|---|---|

Product

[chemical structure]

| 162 | Naphthol compound    Propargyl alcohol compound | 64 |

[chemical structures of naphthol compound and propargyl alcohol compound]

Product

[chemical structure of product]

TABLE 33

| Example No. | Experimental values | | | Calculated values | | |
|---|---|---|---|---|---|---|
| | C | H | S | C | H | S |
| 159 | 53.86 | 8.03 | 1.71 | 53.77 | 7.90 | 1.79 |
| 160 | 54.12 | 8.01 | 1.65 | 54.00 | 7.92 | 1.82 |
| 161 | 55.57 | 8.17 | 1.82 | 55.34 | 7.96 | 1.76 |
| 162 | 58.17 | 7.78 | 1.90 | 57.98 | 7.97 | 1.95 |

Examples 163 to 166

Evaluation of Physical Properties of Photochromic Plastic Lenses Manufactured by Coating Method Photochromic plastic lenses were manufactured and their characteristic properties were evaluated in the same manner as in Example 8 except that the compounds obtained in Examples 159 to 162 were used as the chromene compound. The results are shown in Table 34. In Table 34, compounds Nos. 159 to 162 are the chromene compounds obtained in Examples 159 to 162, respectively. For example, the chromene compound obtained in Example 159 is represented as compound No. 159.

TABLE 34

| Example No. | Compound No. | λmax (nm) | Color optical density $A_0$ | Double peak characteristic $A_Y/A_B$ | Fading half period $\tau^{1/2}$ (sec) | Initial coloration (absorption end) (nm) |
|---|---|---|---|---|---|---|
| 163 | 159 | 470 | 0.88 | 1.66 | 52 | 400 |
| | | 572 | 0.53 | | 52 | |
| 164 | 160 | 465 | 0.91 | 1.65 | 45 | 403 |
| | | 566 | 0.55 | | 45 | |
| 165 | 161 | 466 | 0.79 | 1.61 | 47 | 400 |
| | | 565 | 0.49 | | 47 | |
| 166 | 162 | 465 | 0.76 | 1.62 | 49 | 401 |
| | | 565 | 0.47 | | 49 | |

| Example No. | Initial coloration (thermochromism) (%) | Residual rate $(A_{50}/A_0) \times 100(\%)$ | Double peak characteristic after heating $A_Y'/A_B'$ | Color drift $1 - (A_Y/A_B)/(A_Y'/A_B')$ |
|---|---|---|---|---|
| 163 | 83 | 83 | 1.64 | 0.01 |
| | 86 | 83 | | |
| 164 | 83 | 84 | 1.65 | 0.00 |
| | 88 | 84 | | |
| 165 | 85 | 80 | 1.60 | 0.01 |
| | 88 | 80 | | |
| 166 | 85 | 80 | 1.62 | 0.00 |
| | 89 | 80 | | |

EFFECT OF THE INVENTION

The chromene compound of the present invention develops a color of a neutral tint and has little initial coloration, high color development sensitivity, high color optical density and high fading speed even when it is dispersed into a solution or a polymer solid matrix as well as excellent durability.

Therefore, when a photochromic lens is manufactured by using the chromene compound of the present invention, it develops a deep color of a neutral tint swiftly when it moves outside and fades to return to its original color swiftly when it returns inside from outside and further has high durability so that it can be used for a long time.

The invention claimed is:

1. A chromene compound having a central skeleton represented by the following formula (1):

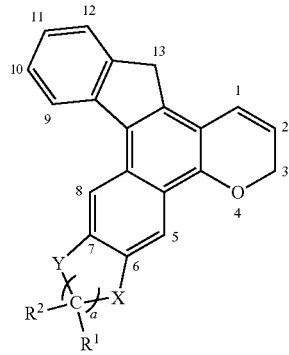

(1)

wherein either one or both of X and Y are sulfur atoms, and when one of them is a sulfur atom, the other is an oxygen atom or group represented by the following formula,

$R^{12}$ is a hydrogen atom, hydroxyl group, alkyl group, haloalkyl group, cycloalkyl group, alkoxy group, halogen atom, aralkyl group, aralkoxy group, aryloxy group or aryl group, $R^1$ and $R^2$ are each independently a hydrogen atom, hydroxyl group, alkyl group, haloalkyl group, cycloalkyl group, alkoxy group, amino group, heterocyclic group having a ring member nitrogen atom and bonded to a carbon atom bonded thereto via the nitrogen atom, cyano group, nitro group, formyl group, hydroxycarbonyl group, alkylcarbonyl group, alkoxycarbonyl group, halogen atom, aralkyl group, aralkoxy group, aryloxy group or aryl group, $R^1$ and $R^2$ may form an aliphatic ring having 3 to 20 ring member carbon atoms together with a carbon atom bonded thereto, and "a" is an integer of 1 to 3.

2. The chromene compound according to claim 1 which is represented by the following formula (2):

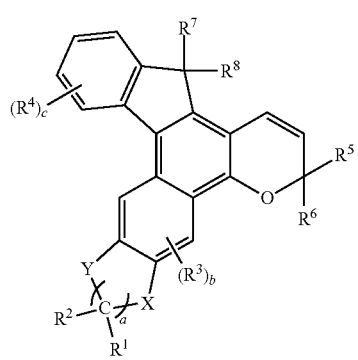

(2)

wherein X, Y, $R^1$, $R^2$ and "a" are as defined in the above formula (1), $R^3$ and $R^4$ are each independently a hydroxyl group, alkyl group, haloalkyl group, cycloalkyl group, alkoxy group, amino group, heterocyclic group having a ring member nitrogen atom and bonded to a benzene ring bonded thereto via the nitrogen atom, cyano group, nitro group, formyl group, hydroxycarbonyl group, alkylcarbonyl group, alkoxycarbonyl group, halogen atom, aralkyl group, aralkoxy group, aryloxy group, aryl group, alkylthio group, cycloalkylthio group, arylthio group or group having a siloxane bond, $R^5$ and $R^6$ are each independently a group represented by the following formula (3):

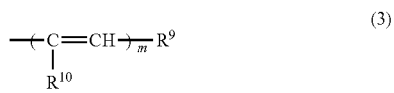

(3)

$R^9$ is an aryl group or heteroaryl group, $R^{10}$ is a hydrogen atom, alkyl group or halogen atom, and "m" is an integer of 1 to 3,
group represented by the following formula (4):

(4)

$R^{11}$ is an aryl group or heteroaryl group, and "n" is an integer of 1 to 3, aryl group, heteroaryl group or alkyl group, $R^5$ and $R^6$ may form an aliphatic hydrocarbon ring together with a carbon atom bonded thereto, $R^7$ and $R^8$ are each independently a hydrogen atom, hydroxyl group, alkyl group, haloalkyl group, cycloalkyl group, alkoxy group, alkoxyalkyl group, formyl group, hydroxycarbonyl group, alkylcarbonyl group, alkoxycarbonyl group, halogen atom, aralkyl group, aralkoxy group, aryloxy group or aryl group, $R^7$ and $R^8$ may form an aliphatic ring having 3 to 20 ring member carbon atoms, condensed polycyclic ring having an aromatic ring or aromatic hetero ring condensed to the aliphatic ring, hetero ring having 3 to 20 ring member atoms, or condensed polycyclic ring having an aromatic ring or aromatic hetero ring condensed to the hetero ring, together with the 13-position carbon atom bonded thereto, "b" is an integer of 0 to 2, "c" is an integer of 0 to 4, when "b" is 2, two $R^3$'s may be the same or different, and when "c" is 2 to 4, a plurality of $R^4$'s may be the same or different.

3. The chromene compound according to claim 2, wherein at least one of $R^5$ and $R^6$ in the above formula (2) is any one of the following groups (i) to (iv):
 (i) an aryl group or heteroaryl group having an alkyl group or alkoxy group as a substituent;
 (ii) an aryl group or heteroaryl group having an amino group as a substituent;
 (iii) an aryl group or heteroaryl group having a heterocyclic group which has a nitrogen atom as a ring member hetero atom and is bonded to an aryl group or heteroaryl group via the nitrogen atom as a substituent; and
 (iv) an aryl group or heteroaryl group having a group with a siloxane bond as a substituent.

4. A photochromic curable composition comprising the chromene compound of claim 3 and a polymerizable monomer.

5. A photochromic optical article having a polymer molded product containing the chromene compound of claim 3 dispersed therein as a constituent member.

6. An optical article having an optical substrate all or part of at least one surface of which is covered with a polymer film containing the chromene compound of claim 3 dispersed therein as a constituent member.

7. The chromene compound according to claim 2, wherein, in the above formula (2), $R^7$ and $R^8$ form an aliphatic hydrocarbon ring together with the 13-position carbon atom bonded thereto, and the aliphatic hydrocarbon ring has 4 to 20 ring member carbon atoms and may have at least one substituent selected from the group consisting of alkyl group, haloalkyl group, cycloalkyl group, alkoxy group, amino group, aralkyl group, aryl group and halogen atom.

8. A photochromic curable composition comprising the chromene compound of claim 7 and a polymerizable monomer.

9. A photochromic optical article having a polymer molded product containing the chromene compound of claim 7 dispersed therein as a constituent member.

10. An optical article having an optical substrate all or part of at least one surface of which is covered with a polymer film containing the chromene compound of claim 7 dispersed therein as a constituent member.

11. A photochromic curable composition comprising the chromene compound of claim 2 and a polymerizable monomer.

12. A photochromic optical article having a polymer molded product containing the chromene compound of claim 2 dispersed therein as a constituent member.

13. An optical article having an optical substrate all or part of at least one surface of which is covered with a polymer film containing the chromene compound of claim 2 dispersed therein as a constituent member.

14. A photochromic curable composition comprising the chromene compound of claim 1 and a polymerizable monomer.

15. A photochromic optical article having a polymer molded product containing the chromene compound of claim 1 dispersed therein as a constituent member.

16. An optical article having an optical substrate all or part of at least one surface of which is covered with a polymer film containing the chromene compound of claim 1 dispersed therein as a constituent member.

* * * * *